US008642840B2

(12) United States Patent
Good et al.

(10) Patent No.: US 8,642,840 B2
(45) Date of Patent: *Feb. 4, 2014

(54) NITROGEN-EFFICIENT MONOCOT PLANTS

(71) Applicant: Arcadia Biosciences, Inc., Davis, CA (US)

(72) Inventors: Allen G. Good, Edmonton (CA); Jean C. Kridl, Davis, CA (US); Mary DePauw, Edmonton (CA); Ashok K. Shrawat, Edmonton (CA); George Theodoris, Vallejo, CA (US)

(73) Assignee: Arcadia Biosciences, Inc., Davis, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/622,311

(22) Filed: Sep. 18, 2012

(65) Prior Publication Data
US 2013/0097738 A1    Apr. 18, 2013

Related U.S. Application Data

(62) Division of application No. 11/644,321, filed on Dec. 21, 2006, now Pat. No. 8,288,611.

(60) Provisional application No. 60/753,818, filed on Dec. 23, 2005.

(51) Int. Cl.
*C12N 15/00* (2006.01)
*A01H 1/00* (2006.01)
*C07H 21/04* (2006.01)
*C07K 14/415* (2006.01)
*C12N 15/52* (2006.01)
*C12N 15/63* (2006.01)

(52) U.S. Cl.
USPC ........ 800/295; 800/278; 800/320; 800/320.2; 435/468; 435/183; 435/419; 435/320.1; 530/370; 536/24.1; 536/23.2; 536/23.6

(58) Field of Classification Search
USPC .............. 435/6.1, 69.1, 468, 183, 419, 320.1; 536/23.2, 23.6, 24.1; 800/278, 295, 800/320, 320.2; 530/370
See application file for complete search history.

(56) References Cited

U.S. PATENT DOCUMENTS

| | | | |
|---|---|---|---|
| 5,256,558 A | 10/1993 | Coruzzi et al. |
| 5,750,399 A | 5/1998 | Dixon et al. |
| 5,955,651 A | 9/1999 | Coruzzi et al. |
| 6,080,913 A | 6/2000 | Tarczynski et al. |
| 6,084,153 A | 7/2000 | Good et al. |
| 7,365,185 B2 | 4/2008 | Boukharov et al. |
| 7,390,937 B2 | 6/2008 | Good et al. |
| 7,560,626 B2 | 7/2009 | Good et al. |
| 7,786,343 B2 | 8/2010 | Good et al. |
| 7,982,093 B2 | 7/2011 | Good et al. |
| 2004/0116682 A1 | 6/2004 | Cheikh et al. |
| 2004/0187176 A1 | 9/2004 | Boyes et al. |

FOREIGN PATENT DOCUMENTS

| | | |
|---|---|---|
| EP | 0303780 A2 | 2/1989 |
| WO | 90/13633 A1 | 11/1990 |
| WO | 91/04325 A1 | 4/1991 |
| WO | 92/20807 A1 | 11/1992 |
| WO | 93/07279 A1 | 4/1993 |
| WO | 95/09911 A1 | 4/1995 |
| WO | 97/30163 A1 | 8/1997 |
| WO | 01/55433 A2 | 8/2001 |
| WO | 03/000898 A1 | 1/2003 |
| WO | 2007/075925 A2 | 7/2007 |
| WO | 2007076115 A2 | 7/2007 |

OTHER PUBLICATIONS

Stroeher et al., "Molecular Cloning and Expression of a Turgor-Responsive Gene in *Brassica napus*", Plant Molecular Biology, vol. 27, Feb. 1995, pp. 541-551.

Suzuki et al., "Deletion Analysis and Localization of SbPRP1, a Soybean Cell Wall Protein Gene, in Roots of Transgenic Tobacco and Cowpea", Plant Molecular Biology, vol. 21, 1993, pp. 109-119.

Temple et al., "Modulation of Glutamine Synthetase Gene Expression in Tobacco by the Introduction of an Alfalfa Glutamine Synthetase Gene in Sense and Antisense Orientation: Molecular and Biochemical Analysis", Molecular and General Genetics, vol. 236, 1993, pp. 315-325.

Tsai et al., "Dark-Induced and Organ-Specific Expression of Two Asparagine Synthetase Genes in *Pisum sativum*", The EMBO Journal, vol. 9, No. 2, 1990, pp. 323-332.

Turner et al., "Drought Resistance and Adaption to Water Deficits in Crop Plants" In Stress Physiology in Crop Plants, John Wiley & Sons: New York, 1979, pp. 343-372.

Tzchori et al., "Lysine and Threonine Metabolism are Subject to Complex Patterns of Regulation in *Arabidopsis*", Plant Molecular Biology, vol. 32, No. 4, Nov. 1996, pp. 727-734.

Udvardi et al., "Isolation and Analysis of a cDNA Clone that Encodes an Alfalfa (*Medicago sativa*) Aspartate Aminotransferase", Molecular and General Genetics, vol. 231, 1991, pp. 97-105.

Vauler et al., "Communication: Anaerobic Metabolism in the N-Limited Green Alga *Selenastrum* Minutum, III. Alanine is the Product of Anaerobic Ammonium Assimilation", Plant Physiology, vol. 95, 1991, pp. 655-658.

Voetberg et al., "Growth of the Maize Primary Root at Low Water Potentials, III. Role of Increased Proline Deposition in Osmotic Adjustment", Plant Physiology, vol. 96, 1991, pp. 1125-1130.

(Continued)

Primary Examiner — Phuong Bui
(74) Attorney, Agent, or Firm — Morrison & Foerster LLP

(57) ABSTRACT

Methods of increasing nitrogen utilization efficiency in monocot plants through genetic modification to increase the levels of alanine aminotransferase expression and plants produced there from are described. In particular, methods for increasing the biomass and yield of transgenic monocot plants grown under nitrogen limiting conditions compared to non-transgenic plants are described. In this way, monocot plants may be produced that maintain a desired yield while reducing the need for high levels of nitrogen application.

16 Claims, 17 Drawing Sheets

(56) References Cited

OTHER PUBLICATIONS

Wakasa et al., "High-Level Tryptophan Accumulation in Seeds of Transgenic Rice and its Limited Effects on Agronomic Traits and Seed Metabolite Profile", Journal of Experimental Botany, vol. 57, No. 12, 2006, pp. 1-10.
Watson et al., "Recombination at the Molecular Level", Chapter 11 in Molecular Biology of the Gene. Gillen, J. R. eds., Fourth Edition, The Benjamin/Cummings Publishing Company, Inc.:Menlo Park, CA, 1987, pp. 313-338.
Zehnacker et al., "Purification and Properties of Tobacco Ferredoxin-Dependent Glutamate Synthase, and Isolation of Corresponding cDNA Clones", Planta, vol. 187, 1992, pp. 266-274.
Extended European Search Report received for European Patent Application No. 06847950.0, mailed on Aug. 10, 2009, 6 pages.
Extended European Search Report received for European Patent Application No. 06848873.3, mailed on Jul. 30, 2009, 7 Pages.
International Search Report and Written Opinion received for PCT Patent Application No. PCT/US2006/048857, mailed on Oct. 4, 2007, 5 pages.
International Search Report and Written Opinion received for PCT Patent Application No. PCT/US2006/049241, mailed on Mar. 20, 2008, 11 pages.
Back et al., "Isolation of the Spinach Nitrate Reductase Gene Promoter which Confers Nitrate Inducibility on GUS Gene Expression in Transgenic Tobacco", Plant Molecular Biology, vol. 17, 1991, pp. 9-18.
Benfey et al., "The Cauliflower Mosaic Virus 35S Promoter: Combinatorial Regulation of Transcription in Plants", Science, vol. 250, Nov. 16, 1990, pp. 959-966.
Bohnert et al., "Adaptations to Environmental Stresses", The Plant Cell, vol. 7, Jul. 1995, pp. 1099-1111.
Cheng et al., "A New Locus (NIA 1) in *Arabidopsis thaliana* Encoding Nitrate Reductase", The EMBO Journal, vol. 7, No. 11, 1988, pp. 3309-3314.
Cheng et al., "Differential Expression of the Two *Arabidopsis* Nitrate Reductase Genes", Plant Physiology, vol. 96, 1991, pp. 275-279.
Coruzzi et al., "Primary N-Assimilation Into Amino Acids in *Arabidopsis*", The *Arabidopsis* Book, American Society of Plant Biologists, Sep. 30, 2003, pp. 1-17.
Crawford et al., "Nitrate: Nutrient and Signal for Plant Growth", The Plant Cell, vol. 7, Jul. 1995, pp. 859-868.
Eckes et al., "Overproduction of Alfalfa Glutamine Synthetase in Transgenic Tobacco Plants", Molecular and General Genetics, vol. 217, 1989, pp. 263-268.
Edwards et al., "Cell-Specific Expression in Transgenic Plants Reveals Nonoverlapping Roles for Chloroplast and Cytosolic Glutamine Synthetase", Proceedings of the National Academy of Science, vol. 87, May 1990, pp. 3459-3463.
Good et al., "Anaerobic Induction of Alanine Aminotransferase in Barley Root Tissue", Plant Physiology, vol. 90, 1989, pp. 1305-1309.
Good et al., "Can Less Yield More? Is Reducing Nutrient Input Into the Environment Compatible With Maintaining Crop Production?", Trends in Plant Science, vol. 9, Dec. 1, 2004, pp. 597-605.
Good et al., "Effects of Drought Stress on the Water Relations in *Brassica* Species", Canadian Journal of Plant Science, Vo. 73, 1993, pp. 525-529.
Good et al., "Engineering Nirtogen Use Efficiency With Alanine Aminotransferase", Canadian Journal of Botany / Journal Canadien De Botanique, vol. 85, No. 3, Mar. 1, 2007, pp. 252-262.
Good et al., "Purification and Characterization of an Anaerobically Induced Alanine Aminotransferase from Barley Roots", Plant Physiology, vol. 99, 1992, pp. 1520-1525.
Good et al., "The Effects of Drought Stress on Free Amino Acid Accumulation and Protein Synthesis in *Brassica napus*", Physiologia Plantarum, vol. 90, 1994, pp. 9-14.
Goodwin et al., "Nitrogen Fixation, Amino Acid Biosynthesis and Proteins", Chapter 9 in Introduction to Plant Biochemistry. 2nd Edition, Pergamon Press Ltd: New York, 1983, pp. 328-361.
Guerrero et al., "Tissue-Specific Expression of a Plant Turgor-Responsive Gene with Amino Acid Sequence Homology to Transport-Facilitating Proteins", Plant Molecular Biology, vol. 21, 1993, pp. 929-935.
Guerrero et al., "Turgor-Responsive Gene Transcription and RNA Levels Increase Rapidly when Pea Shoots are Wilted. Sequence and Expression of Three Inducible Genes", Plant Molecular Biology, vol. 15, 1990, pp. 11-26.
Hageman et al., "The Use of Physiological Traits for Corn Improvement", Chapter 7 in Corn and Corn Improvement., Sprague & Dudley, American Society of Agronomy: Madison, WI, 1988, pp. 431-461.
Hanson et al., "Metabolic Responses of Mesophytes to Plant Water Deficits", Annual Review of Plant Physiology, vol. 33, 1982, pp. 163-203.
Hemon et al., "Targeting of Glutamine Synthetase to the Mitochondria of Transgenic Tobacco", Plant Molecular Biology, vol. 15, 1990, pp. 895-904.
Hirel et al., "Forcing Expression of a Soybean Root Glutamine Synthetase Gene in Tobacco Leaves Induces a Native Gene Encoding Cytosolic Enzyme", Plant Molecular Biology, vol. 20,1992, pp. 207-218.
Iturriaga et al., "Expression of Desiccation-Related Proteins from the Resurrection Plant *Craterostigma plantagineum* in Transgenic Tobacco", Plant Molecular Biology, vol. 20, 1992, pp. 555-558.
Iwamoto et al., "Strong expression of the rice catalase gene CatB promoter in protoplasts and roots of both a monocot and dicots", Plant Physiology and Biochemistry, vol. 42, No. 3, Mar. 2004, pp. 241-249.
Jones et al., "Developmental Expression of a Turgor-Responsive gene that Encodes an Intrinsic Membrane Protein", Plant Molecular Biology, vol. 28, No. 6, 1995, pp. 983-996.
Jones et al., "Osmostic Adjustment in Leaves of *Sorghum* in Response to Water Deficits", Plant Physiology, vol. 61, 1978, pp. 122-126.
Kaye et al., "Characterization of a Gene for Spinach CAP160 and Expression of Two Spinach Cold-Acclimation Proteins in Tobacco", Plant Physiology, vol. 116, 1998, pp. 1367-1377.
Kikuchi et al., "Molecular Characterization of a Gene for Alanine Aminotransferase from Rice (*Oryza sativa*)", Plant Molecular Biology, vol. 39, 1999, pp. 149-159.
Kim et al., "Constitutive Overexpression of Cystathionine Gamma-Synthase in *Arabidopsis* Leads to Accumulation of Soluble Methionine and S-Methylmethionine", Plant Physiology, vol. 128, Jan. 2002, pp. 95-107.
Kim et al., "A 20 Nucleotide Upstream Element is Essential for the Nopaline Synthase (NOS) Promoter Activity", Plant Molecular Biology, vol. 24, pp. 105-117, 1994.
Koyama et al., "Promoter of *Arabidopsis thaliana* Phosphate Transporter Gene Drives Root-specific Expression of Transgene in Rice", Journal of Bioscience and Bioengineering, vol. 99, No. 1, 2005, pp. 38-42.
Koziel et al., "Optimizing Expression of Transgenes with an Emphasis on Post-Transcriptional Events", Plant Molecular Biology, vol. 32, 1996, pp. 393-405.
Lam et al., "Use of *Arabidopsis* Mutants and Genes to Study Amide Amino Acid Biosynthesis", The Plant Cell, vol. 7, Jul. 1995, pp. 887-898.
Liaw et al., "Feedback Inhibition of Fully Unadenylylated Glutamine Synthetase from *Salmonella typhimurium* by Glycine, Alanine, and Serine", Proceedings of the National Academy of Sciences of the United States of America, vol. 90, Jun. 1993, pp. 4996-5000.
Montgomery et al., "Identification of an Ethylene-Responsive Region in the Promoter of a Fruit Ripening Gene", Proceedings of the National Academy of Science, vol. 90, Jul. 1993, pp. 5939-5943.
Morgan et al., "Osmoregulation and Water Stress in Higher Plants", Annual Review of Plant Physiology, vol. 35, 1984, pp. 299-319.
Muench et al., "Cloning and Expression on a Hypoxic and Nitrogen Inducible Maize Alanine Aminotransferase Gene", Physiologia Plantarum, vol. 103, Aug. 1998, pp. 503-512.
Muench et al., "Hypoxically Inducible Barely Alanine Aminotransferase: cDNA Cloning and Expression Analysis", Plant Molecular Biology, vol. 24,1994, pp. 417-427.

(56) References Cited

OTHER PUBLICATIONS

New England Biolabs (UK) Ltd. "Phospho-mTOR (Ser2448) Blocking Peptide #1230" retrieved from Internet on Jun. 26, 2007, 2 pages, available at: <http://www.neb.uk.com/productcatalogue/productinfo.aspx?id=Cell20Signaling20TechnologY/1230~UK~GUEST@1~@2XX@2#references>.

Nomura et al., "The Promoter for C-4-type Mitochondrial Aspartate Aminotransferase Does not Direct Bundle Sheath-specific Expression in Transgenic Rice Plants", Plant Cell Physiology, vol. 46, No. 5, May 2005, pp. 743-753.

O'Neal et al., "Pea Leaf Glutamine Synthetase", Plant Physiology, vol. 55, 1975, pp. 968-974.

Peterman et al., "The Glutamine Synthetase Gene Family of *Arabidopsis thaliana*: Light-Regulation and Differential Expression in Leaves, Roots and Seeds", Molecular and General Genetics, vol. 230, 1991, pp. 145-154.

Rhodes et al., "Metabolic Changes Associated with Adaptation of Plant Cells to Water Stress", Plant Physiology, vol. 82, 1986, pp. 890-903.

Sakakibara et al., "Isolation and Characterization of a cDNA that Encodes Maize Glutamate Dehydrogenase", Plant and Cell Physiology, vol. 36, No. 5, 1995, pp. 789-797.

Shrawat et al., "Genetic Engineering on Improved Nitrogen Use Efficiency in Rice by the Tissue-Specific Expression of Alanine Aminotransferase", Plant Biotechnology Journal, vol. 6, No. 7, Sep. 2008, pp. 722-732.

Skriver et al., "Gene Expression in Response to Abscisic Acid and Osmotic Stress", The Plant Cell, vol. 2, Jun. 1990, pp. 503-512.

Son et al., "Molecular Cloning of an Alanine Aminotransferase from NAD-Malic Enzyme Type C4 Plant *Pancium miliaceum*", Plant Molecular Biology, vol. 20, 1992, pp. 705-713.

Son et al., "Purification and Characterization of Alanine Aminotransferase from *Panicum miliaceum* Leaves", Archives of Biochemistry and Biophysics, vol. 289, No. 2, Sep. 1991, pp. 262-266.

Spencer et al., "Segregation of Transgenes in Maize", Plant Molecular Biology, Vo. 18, 1992, pp. 201-210.

Stewart et al., "Inhibition of Proline Oxidation by Water Stress", Plant Physiology, vol. 59, 1977, pp. 930-932.

Schematic of Key Steps in Nitrogen Utilization in a Plant Cell

FIGURE 2, part A

```
                              1                                                  50
        Barley alaAT    (1)   MAATVAVDNLNPKVLKCEYAVRGEIVIHAQRLQEQLKTQPGSLPFDEILY
        P. miliaceum    (1)   MAATVAVENLNPKVLKCEYAVRGEIVIHAQHLQQQLQTQPGSLPFDEILY
        Rice alaAT1     (1)   AAPSVAVDNLNPKVLNCEYAVRGEIVIHAQRLQQQLQTQPGSLPFDEILY
        Rice alaAT2     (1)   GAAPVSLDTINPKVLKCEYAVRGEIVTHAQ-LQQELQKNPDSLPFDEILY
        Rice alaAT4     (1)   AARALTVSSLNPKVLALADHHLGGLVARRAQLVTVT-VNILIVERKKILQ
        Rice alaAT3     (1)   HSPSITAETINQKVRIFTYEPCGEIVRHARRLEKEIYENPGSLPFQEIIY
             Maize      (1)   MAASVTVENLNPKVLKCEYAVRGEIVIHAQRRQQQLQTQPGSLPFDEILY
   Arabidopsis At1g17290 (1)  SSLPVTLDTINPKVIKCEYAVRGEIVNIAQKLQEDLKTNKDAYPFDEIIY
   Arabidopsis At1g72330 (1)  SSLPVTLDSINPKVLKCEYAVRGEIVNIAQKLQEDLKTNKDAYPFDEIIY
   Arabidopsis At1g23310 (1)  ALKALDYDTLNENVKKCQYAVRGELYLRASELQKEGKK---------IIF
   Arabidopsis At1g70580 (1)  SLKALDYESLNENVKNCQYAVRGELYLRASELQKEGKK---------IIF
           Capsicum     (1)   -MDSITIDTINPKVLKCEYAVRGEIVTIAQKLQQDLKDNPGSHPFDEILY
        Chlamydomonas   (1)   EGKVLHPHLLNENVVKTQYAVRGELYLRAEQLRKEGKE---------IIF
              human     (1)   RAKVLTLDGMNPRVRRVEYAVRGPIVQRALELEQELRQGVK-KPFTEVIR
              yeast     (1)   PAEQLTLEDVNENVLKAKYAVRGAIPMRAEELKAQLEKDPQSLPFDRIIN
            E. coli     (1)   ----MSPIEKSSKLENVCYDIRGPVLKEAKRLEEEG---------NKVLK
        Thermococcus    (1)   ------MVKASKRAMSIEYAIR-DVVLPARELEKQG---------IKIIK
                              51                                                 100
        Barley alaAT   (51)   CNIGNPQSLGQQP-VTFFREVLALCDHPDLLQREEI----KTLFSADSIS
        P. miliaceum   (51)   CNIGNPQSLGQQP-VTFFREVLALCDHPCLLEKEET----KSLFSADAIS
        Rice alaAT1    (51)   CNIGNPQSLGQKP-VTFFREVIALCDHPCLLEKEET----KSLFSADAIS
        Rice alaAT2    (50)   CNIGNPQSLGQQP-VTFFREVLSLCDHPALLDKSET----HALYS-DAIE
        Rice alaAT4    (50)   ADTSMQQELDANPASHPFSEVLALCNHPHLLDRSEA----SFMFSSDAIT
        Rice alaAT3    (51)   CNLGNPQALGQRP-INFFREVLSLCDNPSLIDRDEA----RALFSPCALK
             Maize     (51)   CNIGNPQSLGQQP-VTFFREVLALCDHPCLLEKEET----KSLFSADAIS
   Arabidopsis At1g17290 (51) CNIGNPQSLGQQP-ITFFREVLALCSYTALLDESAT----HGLFSSDSIE
   Arabidopsis At1g72330 (51) CNIGNPQSLGQLP-IKFFREVLALCDHASLLDESET----HGLFSTDSID
   Arabidopsis At1g23310 (42) TNVGNPHALGQKP-LTFPRQVVALCQAPFLLDDPNV----GMLFPADAIA
   Arabidopsis At1g70580 (42) TNVGNPHALGQKP-LTFPRQVVSLCQAPFLLDDPNV----GMIFPADAIA
           Capsicum    (50)   CNIGNPQSLAQQP-ITFFREVLALCDHPSILDKSET----QGLFSADAIE
        Chlamydomonas  (42)   TNVGNPHALGAKP-LTFTRQVLALCAAPFLLDHPKV----EDMFPADAIA
              human    (50)   ANIGDAQAMGQRP-ITFLRQVLALCVNPDLLSSP--------NFPDDAKK
              yeast    (51)   ANIGNPQQLQQKP-LTYYRQVLSLLQYPELLNQNEQQLVDSKLFKLDAIK
            E. coli    (38)   LNIGNPAPFGFDA-----------------------------P-----
        Thermococcus   (35)   LNIGDPVKFDFQP-----------------------------P----E
                              101                                                150
        Barley alaAT   (96)   RAKQILAMIPGRATGAYSHSQGIKGLRDAIASGIASRDG-FPANADDIFL
        P. miliaceum   (96)   RAKQILSTIPGRATGAYSHSQGIKGLRDAIAAGIASRDG-FPANADDIFV
        Rice alaAT1    (96)   RATTILASIPGRATGAYSHSQGIKGLRDAIAAGIASRDG-YPANADDIFL
        Rice alaAT2    (94)   RAWQILDKIPGRATGAYSHSQGIKGLRDEIAAGIAARDG-FHASGDNIFL
        Rice alaAT4    (96)   RAREIVGFIPGKTTGGYSHCQANSIVSEFRANADKYGNE-LSSN-----L
        Rice alaAT3    (96)   RARKIIESLPGRDSGSYTSSQGVRGLREAVADGIAARDG-FPSKPDNIFL
             Maize     (96)   RAKQILATIPGRATGAYSHSQGIKGLRDAIAAGIMSRDG-FPANADDIFI
   Arabidopsis At1g17290 (96) RAWKILDQIPGRATGAYSHSQGIKGLRDAIADGIEARDG-FPADPNDIFM
   Arabidopsis At1g72330 (96) RAWRILDHIPGRATGAYSHSQGIKGLRDVIAAGIEARDG-FPADPNDIFL
   Arabidopsis At1g23310 (87) RAKHYLSLTSGG-LGAYSDSRGLPGVRKEVAEFIQRRDG-YPSNPELIFL
   Arabidopsis At1g70580 (87) RAKHYLSLTSGG-LGAYSDSRGLPGVRKEVAEFIERRDG-YPSDPELIFL
           Capsicum    (95)   RAFQILDQIPGRATGAYSHSQGIKGLRDTIASGIEARDG-FPADPNDLFL
        Chlamydomonas  (87)   RAKKILASFKGG-VGAYTDSRGNPLVREEVARFIEKRDG-VPSNPDHIFL
              human    (91)   RAERILQACGGHSLGAYSVSSGIQLIREDVARYIERRDGGIPADPNNVFL
              yeast   (100)   RAKSLMEDIGGS-VGAYSSSQGVEGIRKSVAEFITKRDEGEISYPEDIFL
            E. coli   (52)   DEILVDVIRNLPTAQGYCDSKGLYSARKAIMQHYQAR-GMRDVTVEDIYI
        Thermococcus  (50)   HMKKAYCEAIMEGHNYYGDSEGDRELREAIVEREKKKNG-VDITPEDVQV
```

FIGURE 2, cont., part B

```
                         151                                              200
        Barley alaAT (145) TDGASPGVHLMMQLLIRNE---KDGILVPIPQYPLYSASIALHGGALVPY
         P. miliaceum (145) TDGASPGVHMMMQLLIRNE---KDGILCPIPQYPLYSASIALHGGTLVPY
          Rice alaAT1 (145) TDGASPGVHMMMQLLIRNE---KDGILCPIPQYPLYSASIALHGGALVPY
          Rice alaAT2 (143) TDGASPAVHMMMQLLIRSE---NDGILCPIPQYPLYSASIALHGGSLVPY
          Rice alaAT4 (140) --TIFDRVHMMMHLLIRGK---KDGILCPIPSHSLYTDSMVLRGATLVPY
          Rice alaAT3 (145) TDGASSAINMMMQILIRSH---EDGILCPLPEYPLYSASIILHGGTMVPY
                Maize (145) TDGASPGVHMMMQLLIRNE---KDGILCPIPQYPLYSASIALHGGTLVPY
  Arabidopsis At1g17290 (145) TDGASPGVHMMMQLLITSE---KDGILCPIPQYPLYSASIALHGGTLVPY
  Arabidopsis At1g72330 (145) TDGASPAVHMMMQLLLSSE---KDGILSPIPQYPLYSASIALHGGSLVPY
  Arabidopsis At1g23310 (135) TDGASKGVMQILNCVIRGN---GDGILVPVPQYPLYSATISLLGGTLVPY
  Arabidopsis At1g70580 (135) TDGASKGVMQILNCVIRGQ---KDGILVPVPQYPLYSATISLLGGTLVPY
             Capsicum (144) TDGASPAVHMMMQLLIRSQ---NDGILCPIPQYPLYSASIALHGGTLVPY
         Chlamydomonas (135) TDGASVAVRLCLNAMIRHD---RDSVLVPIPQYPLYSASIRLYGGTLVGY
                human (141) STGASDAIVTVLKLLVAGEGHTRTGVLIPIPQYPLYSATLAELGAVQVDY
                yeast (149) TAGASAAVNYLLSIFCRGP---ETGVLIPIPQYPLYTATLALNNSQALPY
              E. coli (101) GNGVSELIVQAMQALLNSG----DEMLVPAPDYPLWTAAVSLSSGKAVHY
          Thermococcus  (99) TAAVTEALQFIFGALIDGG----EEILIPGPSYPPYVGLVKFYGGVPKAY
                         201                                              250
        Barley alaAT (192) YLNESTGWGLETSDVKKQLEDARSRGINVRALVVINPGNPTGQVLAEENQ
         P. miliaceum (192) YLDEKTGWGLEISDLKKQLEDARSKGIDVRALVVINPGNPTGQVLAEDNQ
          Rice alaAT1 (192) YLNESTGWGLEISDLKKQLEDSRLKGIDVRALVVINPGNPTGQVLAEENQ
          Rice alaAT2 (190) FLDEETGWGLEVDELKKQLEEAQSKGITVRALVVINPGNPTGQVLAEENQ
          Rice alaAT4 (185) YLDESRGWSVNISDLKKQLDGARAKGIDVRGLVVVNPGNPTGQVLVEENQ
          Rice alaAT3 (192) NLTEDSIWGLEIFEVKRCLEDARASGLTIRAMVVINPGNPTGQVLSITNQ
                Maize (192) YLNEKNGWGLEISDFKTRLEDVRSKGIDVRALVVINPGNPTGQVLAEDNQ
  Arabidopsis At1g17290 (192) YLDEASGWGLEISELKKQLEDARSKGITVRALAVINPGNPTGQVLSEENQ
  Arabidopsis At1g72330 (192) YLDEATGWGLEISDLKKQLEEARSKGISVRALVVINPGNPTGQVLAEENQ
  Arabidopsis At1g23310 (182) YLDESENWGLDVANLRQSVAQARSQGITVRAMVIINPGNPTGQCLSEANI
  Arabidopsis At1g70580 (182) YLEESENWGLDVNNLRQSVAQARSQGITVRAMVIINPGNPTGQCLSEANI
             Capsicum (191) YLDEQTGWGLEISELEHQLNTAKSNGIDVRALVVINPGNPTGQVLGEANQ
         Chlamydomonas (182) FLDERRGWGLSVEELQRALQESREEGKLVRGLVFINPGNPTGQCLSKENL
                human (191) YLDEERAWALDVAELHRALGQAR-DHCRPRALCVINPGNPTGQVQTRECI
                yeast (196) YLDENSGWSTNPEEIETVVKEAIQNEIKPTVLVVINPGNPTGAVLSPESI
              E. coli (147) LCDESSDWFPDLDDIRAKITPRT------RGIVIINPNNPTGAVYSKELL
          Thermococcus (145) RTVEEEGWQPDIDDMRKKITEKT------KAIAVINPNNPTGALYEKKTL
                         251                                              300
        Barley alaAT (242) YDIVKFCKNEGLVLLADEVYQENIYVDNKKFHSFKKIVRSLGYEE----
         P. miliaceum (242) CDIVRFCKNEGLVLLADEVYQENIYVDDKKFNSFKKIARSVGYED----
          Rice alaAT1 (242) RDIVKFCKNEGLVLLADEVYQENIYVDNKKFNSFKKIARSMGYNED---
          Rice alaAT2 (240) KKIVEFCKNEGLVLLADEVYQENIYVEDKKFHSFKKIARSMGYTDD---
          Rice alaAT4 (235) CEIVELCKNECLVLLADEVYQENIYTDQKKFNSFKKVARSIGYGEG---
          Rice alaAT3 (242) EEIVEFCRKEGLVILADEVYQENVYTENKRFNSFKKVARSLGYDHH---
                Maize (242) YDIVKFCKNEGLVLLADEVYQENIYVDNKKFNSFKKIVRSMGYGED---
  Arabidopsis At1g17290 (242) RDVVKFCKQEGLVLLADEVYQENVYVPDKKFHSFKKVRSMGYGEK----
  Arabidopsis At1g72330 (242) RDIVNFCKQEGLVLLADEVYQENVYVPDKKFHSFKKVARSLGYGEK----
  Arabidopsis At1g23310 (232) REILKFCYNEKLVLLGDEVYQQNIYQDERPFISSKKVLMEMGSPFSK---
  Arabidopsis At1g70580 (232) REILRFCCDERLVLLGDEVYQQNIYQDERPFISSKKVLMDMGAPISK---
             Capsicum (241) REIVEFCKKEGLVLLADEVYQENVYVPDKKFHSFKKITRSMGYGEK---
         Chlamydomonas (232) QELIKLAYQEKIVLMADEVYQENVYQDERPFVSAKKVMWEMGEPYRS---
                human (240) EAVIRFAFEERLFLLADEVYQDNVYAAGSQFHSFKKVLMEMGPPYAG---
                yeast (246) AQIFEVAAKYGTVVIADEVYQENIFPG-TKFHSMKKILRHLQREHPGKFD
              E. coli (191) MEIVEIARQHNLIIFADEIYDKILYDDAEHHSIAPLAP-----------
          Thermococcus (189) QEIIDLAGEYDLPIISDEIYDLMTYEG---KHVSP--------GSLT--K
```

FIGURE 2, cont., part C

```
                          301                                              350
        Barley alaAT (288) DLPLVSYQSVSKGYYGECGKRG--GYFEITGFSAPVREQIYKIASVNLCS
         P. miliaceum (288) DLPLVSFQSVSKGYYGECGKRG--GYMEITGFSAPVREQIYKIASVNLCS
          Rice alaAT1 (288) DLPLVSFQSVSKGYYGECGKRG--GYMEITGFSAPVREQIYKVASVNLCS
          Rice alaAT2 (286) DLPLVSFQSVSKGYYGECGKRG--GYMEVTGFSADVREQIYKVASVNLCS
          Rice alaAT4 (281) DISLVSFHSVSNGYYGECGRRG--GYMEVTGFSSEVRGEVYKVASLSACS
          Rice alaAT3 (288) DLSIVSFHSVSMGYYGECGRRG--GYMEICGFGDDVIDEMYKLASLTICP
                Maize (288) DLPLVSLQSVSKGYYGECGKRG--GYMEITGFSAPVREQIYKIASVNLCS
  Arabidopsis At1g17290 (288) DLALVSFQSVSKGYYGECGKRG--GYMEVTGFTSDVREQIYKMASVNLCS
  Arabidopsis At1g72330 (288) DISLVSYQSVSKGYYGECGKRG--GYMEVTGFTSDVREQIYKMASVNLCS
  Arabidopsis At1g23310 (279) EVQLVSFHTVSKGYWGECGQRG--GYFEMTNLPPRVVEEIYKVASIALSP
  Arabidopsis At1g70580 (279) EVQLISFHTVSKGYWGECGQRG--GYFEMTNIPPRTVEEIYKVASIALSP
             Capsicum (287) DISLVSFQSVSKGFYGECGKRG--GYMEITGFSPEVREQIYKLASVNLCS
         Chlamydomonas (279) HVELLSFHTVSKGTAGECGLRG--GYVEMTNIHPGAIEEVYKCASINLSP
                human (287) QQELASFHSTSKGYMGECGFRG--GYVEVVNMDAAVQQQMLKLMSVRLCP
                yeast (295) NVQLASLHSTSKGVSGECGQRG--GYMELTGFSHEMRQVILKLASISLCP
              E. coli (229) DLLTITFNGLSKTYRVAGFRQGWMVLNGPKKHAKGYIEGLEMLASMRLCA
         Thermococcus (226) DVPVIVMNGLSKVYFATGWRLGYMYFVDPENKLAEVREAIGKLARIRLCP
                          351                                              400
        Barley alaAT (336) NITGQILASLVMNPPKASDESYASYKAEKDGILASLARRAKALEHAFNKL
         P. miliaceum (336) NITGQILASLVMNPPKVGDESYAAYKAEKDGILQSLARRAKALEDAFNNL
          Rice alaAT1 (336) NITGQILASLVMNPPKAGDASYASYKAEKDGILQSLARRAKALENAFNSL
          Rice alaAT2 (334) NVSGQILASLIMNPPKAGDESYESFMVEKDGILSSLARRAKALEEAFNSL
          Rice alaAT4 (329) NISGQILMSLVMNPPKVGDESYPSYRAERDSILSSLCCAEAMVSTFNSM
          Rice alaAT3 (336) NIAGQILISLVMDPPKLGDEAFEIFMVEKEETYSSLLKRAKALQKAFNGL
                Maize (336) NITGQILASLVMNPPKAGDESYASYKAEKDGILESLARRAKALEDAFNKL
  Arabidopsis At1g17290 (336) NISGQILASLIMSPPKPGDDSYESYIAEKDGILSSLARRAKTLEEALNKL
  Arabidopsis At1g72330 (336) NISGQILASLVMSPPKPGDDSYDSYMAERDGILSSMAKRAKTLEDALNSL
  Arabidopsis At1g23310 (327) NVSAQIFMGLMVNPPKPGDISYDQFARESKGILESLRRRARLMTDGFNSC
  Arabidopsis At1g70580 (327) NVSAQIFMGLMVSPPKPGDISYDQFVRESKGILESLRRRARMMTDGFNSC
             Capsicum (335) NISGQILASLVMSPPKVGDESYESFSAEKEAVLSSLARRAQALQDALNSL
         Chlamydomonas (327) NTMGQIALSVLVNPPKPGDPSYDQYTKEKASELVSLRRRRHMVTDGFNAL
                human (335) PVPGQALLDLVVSPPAPTDPSFAQFQAEKQAVLAELAAKAKLTEQVFNEA
                yeast (343) VVTGQALVDLMVRPPVEGEESFESDQAERNSIHEKLITRAMTLYETFNSL
              E. coli (279) NVPAQHAIQTALGGYQSISEFITPGGRLYE--------QRNRAWELINDI
         Thermococcus (276) NTPAQKAAIAGLRGPMDYLEEYMAKLKE----------RRDYIYKRLNEM
                          401                                              450
        Barley alaAT (386) EGITCNEAEGAMYVFPQICLPQKAIEAAKAANKAPDAFYALRLLESTGIV
         P. miliaceum (386) EGISCNKAEGAMYLFPQIHLPKKAIEAAKAANKAPDAFYALRLLESTGIV
          Rice alaAT1 (386) EGITCNKTEGAMYLFPQLSLPQKAIDAAKAANKAPDAFYALRLLEATGIV
          Rice alaAT2 (384) EGITCNKAEGAMYLFPRIYLPQKAIGAAQAAGTAPDAYYARRLLEATGIV
          Rice alaAT4 (379) EGMTCNKAEGGISVFPSVRLPPRAIEAAEAMNTEPDVFYALRLLESTGIV
          Rice alaAT3 (386) EGVSCNKFEGAMYLFPRLRLPQAAIKAAQLEGVSPDVFYAHRLLDATGIA
                Maize (386) EGFSCNKAEGAMYLFPQIHLPQKAIEAAKAAKKAPDAFYALRLLESTGIV
  Arabidopsis At1g17290 (386) EGVTCNRAEGAMYLFPCLHLPQKAIAAAEAEKTAPDNFYCKRLLKATGIV
  Arabidopsis At1g72330 (386) EGVTCNRAEGAMYLFPRINLPQKAIEAAEAEKTAPDAFYCKRLLNATGVV
  Arabidopsis At1g23310 (377) KNVVCNFTEGAMYSFPQIRLPTGALQAAKQAGKVPDVFYCLKLLEATGIS
  Arabidopsis At1g70580 (377) KNVVCNFTEGAMYSFPQIKLPSKAIQAAKQAGKVPDVFYCLKLLEATGIS
             Capsicum (385) EGVTCNRAEGAMYLFPRINLPDKAIKAAEVAKTAPDAFYAKLLLNATGIV
         Chlamydomonas (377) DGVTCNFTEGAMYSFPQIKLPAKALEAAKAAGKAGDVFYCLKLLEATGIS
                human (385) PGISCNPVQGAMYSFPRVQLPPRAVERAQELGLAPDMFFCLRLLEETGIC
                yeast (393) EGIECQKPQGAMYLFPKIDLPFKAVQEARHLELTPDEFYCKKLLESTGIC
              E. coli (321) PGVSCVKPRGALYMFPKIDAKR--------FNIHDDQKMVLDFLLQEKVL
         Thermococcus (316) PGISTQKPQGAFYIFPKIEE---------GP-WKSDKEFVLDVLHNAHVL
```

FIGURE 2, cont., part D

```
                          451                                              498
       Barley alaAT  (436) VVPGSGFGQVPGTWHFRCTILPQEDKIPAVISRFTVFHEAFMSEYRD-
         P. miliaceum (436) VVPGSGFGQVPGTWHIRCTILPQEDKIPAVITRFKAFHEAFMAEYRD-
           Rice alaAT1 (436) VVPGSGFGQVPGTWHIRCTILPQEEKIPAIISRFKAFHEGFMAAYRD-
           Rice alaAT2 (434) VVPGSGFGQVPGTWHFRCTILPQEDKIPAIISKFKEFHEKFMDEFRD-
           Rice alaAT4 (429) VVPGSVFGQVPGTWHFRCTILPQEEKTRQIISRFNVFHEAFMEEFRS-
           Rice alaAT3 (436) VVPGSGFHPVSGTSHIRCTILPGEETITAMVPSLQAFHEAFMDEFRG-
                 Maize (436) VVPGSGFGQVPGTWHIRCTILPQEDKIPAVISRFRAFHEAFLAEYRD-
    Arabidopsis At1g17290 (436) VVPGSGFRQVPGTWHFRCTILPQEDKIPAIVDRLTAFHQSFMDEFRD-
    Arabidopsis At1g72330 (436) VVPGSGFGQVPGTWHFRCTILPQEDKIPAIVNRLTEFHKSFMDEFRN-
    Arabidopsis At1g23310 (427) TVPGSGFGQKEGVFHLRTTILPAEDEMPEIMDSFKKFNDEFMTQYDN-
    Arabidopsis At1g70580 (427) TVPGSGFGQKEGVFHLRTTILPAEEEMPEIMDSFKKFNDEFMSQYAD-
              Capsicum (435) VVPGSGFRQVPGTWHFRCTILPQEEKIPAIVSRLTEFHKKFMDEFCG-
          Chlamydomonas (427) TVPGSGFGQEEGTFHLRTTILPREEVMTTFVEKFDKFHKDFMKQYS--
                 human (435) VVPGSGFGQREGTYHFRMTILPPLEKLRLLLEKLSRFHAKFTLEYS--
                 yeast (443) TVPGSGFGQEPGTYHLRTTFLAPG---LEWIKKWESFHKEFFDQYRD-
               E. coli (363) LVQGTAFNW-PWPDHFRIVTLPRVDDIELSLSKFARFLSGYHQL----
           Thermococcus (356) FVHGSGFGE-GGEMHFRSIFLAPVPVLEEAMDNLEKFMKERLG-----
```

FIGURE 3, part A

```
                              1                                                   50
      Barley alaAT      (1)   MAATVAVDNLNPKVLKCEYAVRGEIVIHAQRLQEQLKTQPGSLPFDEILY
        P. miliaceum   (1)   MAATVAVENLNPKVLKCEYAVRGEIVIHAQHLQQQLQTQPGSLPFDEILY
         Rice alaAT1   (1)   AAPSVAVDNLNPKVLNCEYAVRGEIVIHAQRLQQQLQTQPGSLPFDEILY
         Rice alaAT2   (1)   GAAPVSLDTINPKVLKCEYAVRGEIVTHAQ-LQQELQKNPDSLPFDEILY
         Rice alaAT4   (1)   AARALTVSSLNPKVLALADHHLGGLVARRAQLVTVT-VNILIVERKKILQ
         Rice alaAT3   (1)   HSPSITAETINQKVRIFTYEPCGEIVRHARRLEKEIYENPGSLPFQEIIY
               Maize   (1)   MAASVTVENLNPKVLKCEYAVRGEIVIHARRQQQQLQTQPGSLPFDEILY
 Arabidopsis At1g17290 (1)   SSLPVTLDTINPKVIKCEYAVRGEIVNIAQKLQEDLKTNKDAYPFDEIIY
 Arabidopsis At1g72330 (1)   SSLPVTLDSINPKVLKCEYAVRGEIVNIAQKLQEDLKTNKDAYPFDEIIY
 Arabidopsis At1g23310 (1)   ALKALDYDTLNENVKKCQYAVRGELYLRASELQKEGKK---------IIF
 Arabidopsis At1g70580 (1)   SLKALDYESLNENVKNCQYAVRGELYLRASELQKEGKK---------IIF
            Capsicum  (1)   -MDSITIDTINPKVLKCEYAVRGEIVTIAQKLQQDLKDNPGSHPFDEILY
                             51                                                  100
      Barley alaAT     (51)  CNIGNPQSLGQQP-VTFFREVLALCDHPDLLQREEIKTLFSADSISRAKQ
        P. miliaceum  (51)  CNIGNPQSLGQQP-VTFFREVLALCDHPCLLEKEETKSLFSADAISRAKQ
         Rice alaAT1  (51)  CNIGNPQSLGQKP-VTFFREVIALCDHPCLLEKEETKSLFSADAISRATT
         Rice alaAT2  (50)  CNIGNPQSLGQQP-VTFFREVLSLCDHPALLDKSETHALYS-DAIERAWQ
         Rice alaAT4  (50)  ADTSMQQELDANPASHPFSEVLALCNHPHLLDRSEASFMFSSDAITRARE
         Rice alaAT3  (51)  CNLGNPQALGQRP-INFFREVLSLCDNPSLIDRDEARALFSPCALKRARK
               Maize  (51)  CNIGNPQSLGQQP-VTFFREVLALCDHPCLLEKEETKSLFSADAISRAKQ
 Arabidopsis At1g17290(51)  CNIGNPQSLGQQP-ITFFREVLALCSYTALLDESATHGLFSSDSIERAWK
 Arabidopsis At1g72330(51)  CNIGNPQSLGQLP-IKFFREVLALCDHASLLDESETHGLFSTDSIDRAWR
 Arabidopsis At1g23310(42)  TNVGNPHALGQKP-LTFPRQVVALCQAPFLLDDPNVGMLFPADAIARAKH
 Arabidopsis At1g70580(42)  TNVGNPHALGQKP-LTFPRQVVSLCQAPFLLDDPNVGMIFPADAIARAKH
            Capsicum (50)  CNIGNPQSLAQQP-ITFFREVLALCDHPSILDKSETQGLFSADAIERAFQ
                            101                                                 150
      Barley alaAT    (100)  ILAMIPGRATGAYSHSQGIKGLRDAIASGIASRDGFPANADDIFLTDGAS
        P. miliaceum (100)  ILSTIPGRATGAYSHSQGIKGLRDAIAAGIASRDGFPANADDIFVTDGAS
         Rice alaAT1 (100)  ILASIPGRATGAYSHSQGIKGLRDAIAAGIASRDGYPANADDIFLTDGAS
         Rice alaAT2 (98)   ILDKIPGRATGAYSHSQGIKGLRDEIAAGIAARDGFHASGDNIFLTDGAS
         Rice alaAT4 (100)  IVGFIPGKTTGGYSHCQANSIVSEFRANADKYGNELSSN-----L--TIF
         Rice alaAT3 (100)  IIESLPGRDSGSYTSSQGVRGLREAVADGIAARDGFPSKPDNIFLTDGAS
               Maize (100)  ILATIPGRATGAYSHSQGIKGLRDAIAAGIMSRDGFPANADDIFITDGAS
 Arabidopsis At1g17290(100) ILDQIPGRATGAYSHSQGIKGLRDAIADGIEARDGFPADPNDIFMTDGAS
 Arabidopsis At1g72330(100) ILDHIPGRATGAYSHSQGIKGLRDVIAAGIEARDGFPADPNDIFLTDGAS
 Arabidopsis At1g23310(91)  YLSLTSGG-LGAYSDSRGLPGVRKEVAEFIQRRDGYPSNPELIFLTDGAS
 Arabidopsis At1g70580(91)  YLSLTSGG-LGAYSDSRGLPGVRKEVAEFIERRDGYPSDPELIFLTDGAS
            Capsicum (99)  ILDQIPGRATGAYSHSQGIKGLRDTIASGIEARDGFPADPNDLFLTDGAS
                            151                                                 200
      Barley alaAT    (150)  PGVHLMMQLLIRNEKDGILVPIPQYPLYSASIALHGGALVPYYLNESTGW
        P. miliaceum (150)  PGVHMMMQLLIRNEKDGILCPIPQYPLYSASIALHGGTLVPYYLDEKTGW
         Rice alaAT1 (150)  PGVHMMMQLLIRNEKDGILCPIPQYPLYSASIALHGGALVPYYLNESTGW
         Rice alaAT2 (148)  PAVHMMMQLLIRSENDGILCPIPQYPLYSASIALHGGSLVPYFLDEETGW
         Rice alaAT4 (143)  DRVHMMMHLLIRGKKDGILCPIPSHSLYTDSMVLRGATLVPYYLDESRGW
         Rice alaAT3 (150)  SAINMMMQILIRSHEDGILCPLPEYPLYSASIILHGGTMVPYNLTEDSIW
               Maize (150)  PGVHMMMQLLIRNEKDGILCPIPQYPLYSASIALHGGTLVPYYLNEKNGW
 Arabidopsis At1g17290(150) PGVHMMMQLLITSEKDGILCPIPQYPLYSASIALHGGTLVPYYLDEASGW
 Arabidopsis At1g72330(150) PAVHMMMQLLLSSEKDGILSPIPQYPLYSASIALHGGSLVPYYLDEATGW
 Arabidopsis At1g23310(140) KGVMQILNCVIRGNGDGILVPVPQYPLYSATISLLGGTLVPYYLDESENW
 Arabidopsis At1g70580(140) KGVMQILNCVIRGQKDGILVPVPQYPLYSATISLLGGTLVPYYLEESENW
            Capsicum (149) PAVHMMMQLLIRSQNDGILCPIPQYPLYSASIALHGGTLVPYYLDEQTGW
```

FIGURE 3, cont., part B

```
                          201                                                250
     Barley alaAT   (200) GLETSDVKKQLEDARSRGINVRALVVINPGNPTGQVLAEENQYDIVKFCK
      P. miliaceum  (200) GLEISDLKKQLEDARSKGIDVRALVVINPGNPTGQVLAEDNQCDIVRFCK
        Rice alaAT1 (200) GLEISDLKKQLEDSRLKGIDVRALVVINPGNPTGQVLAEENQRDIVKFCK
        Rice alaAT2 (198) GLEVDELKKQLEEAQSKGITVRALVVINPGNPTGQVLAEENQKKIVEFCK
        Rice alaAT4 (193) SVNISDLKKQLDGARAKGIDVRGLVVVNPGNPTGQVLVEENQCEIVELCK
        Rice alaAT3 (200) GLEIFEVKRCLEDARASGLTIRAMVVINPGNPTGQVLSITNQEEIVEFCR
             Maize  (200) GLEISDFKTRLEDVRSKGIDVRALVVINPGNPTGQVLAEDNQYDIVKFCK
Arabidopsis At1g17290 (200) GLEISELKKQLEDARSKGITVRALAVINPGNPTGQVLSEENQRDVVKFCK
Arabidopsis At1g72330 (200) GLEISDLKKQLEEARSKGISVRALVVINPGNPTGQVLAEENQRDIVNFCK
Arabidopsis At1g23310 (190) GLDVANLRQSVAQARSQGITVRAMVIINPGNPTGQCLSEANIREILKFCY
Arabidopsis At1g70580 (190) GLDVNNLRQSVAQARSQGITVRAMVIINPGNPTGQCLSEANIREILRFCC
           Capsicum (199) GLEISELEHQLNTAKSNGIDVRALVVINPGNPTGQVLGEANQREIVEFCK
                          251                                                300
     Barley alaAT   (250) NEGLVLLADEVYQENIYVDNKKFHSFKKIVRSLGYGEE-DLPLVSYQSVS
      P. miliaceum  (250) NEGLVLLADEVYQENIYVDDKKFNSFKKIARSVGYGED-DLPLVSFQSVS
        Rice alaAT1 (250) NEGLVLLADEVYQENIYVDNKKFNSFKKIARSMGYNED-DLPLVSFQSVS
        Rice alaAT2 (248) NEGLVLLADEVYQENIYVEDKKFHSFKKIARSMGYTDD-DLPLVSFQSVS
        Rice alaAT4 (243) NECLVLLADEVYQENIYTDQKKFNSFKKVARSIGYGEG-DISLVSFHSVS
        Rice alaAT3 (250) KEGLVILADEVYQENVYTENKRFNSFKKVARSLGYDHH-DLSIVSFHSVS
             Maize  (250) NEGLVLLADEVYQENIYVDNKKFNSFKKIVRSMGYGED-DLPLVSLQSVS
Arabidopsis At1g17290 (250) QEGLVLLADEVYQENVYVPDKKFHSFKKVARSMGYGEK-DLALVSFQSVS
Arabidopsis At1g72330 (250) QEGLVLLADEVYQENVYVPDKKFHSFKKVARSLGYGEK-DISLVSYQSVS
Arabidopsis At1g23310 (240) NEKLVLLGDEVYQQNIYQDERPFISSKKVLMEMGSPFSKEVQLVSFHTVS
Arabidopsis At1g70580 (240) DERLVLLGDEVYQQNIYQDERPFISSKKVLMDMGAPISKEVQLISFHTVS
           Capsicum (249) KEGLVLLADEVYQENVYVPDKKFHSFKKITRSMGYGEK-DISLVSFQSVS
                          301                                                350
     Barley alaAT   (299) KGYYGECGKRGGYFEITGFSAPVREQIYKIASVNLCSNITGQILASLVMN
      P. miliaceum  (299) KGYYGECGKRGGYMEITGFSAPVREQIYKIASVNLCSNITGQILASLVMN
        Rice alaAT1 (299) KGYYGECGKRGGYMEITGFSAPVREQIYKVASVNLCSNITGQILASLVMN
        Rice alaAT2 (297) KGYYGECGKRGGYMEVTGFSADVREQIYKVASVNLCSNVSGQILASLIMN
        Rice alaAT4 (292) NGYYGECGRRGGYMEVTGFSSEVRGEVYKVASLSACSNISGQILMSLVMN
        Rice alaAT3 (299) MGYYGECGRRGGYMEICGFGDDVIDEMYKLASLTICPNIAGQILISLVMD
             Maize  (299) KGYYGECGKRGGYMEITGFSAPVREQIYKIASVNLCSNITGQILASLVMN
Arabidopsis At1g17290 (299) KGYYGECGKRGGYMEVTGFTSDVREQIYKMASVNLCSNISGQILASLIMS
Arabidopsis At1g72330 (299) KGYYGECGKRGGYMEVTGFTSDVREQIYKMASVNLCSNISGQILASLVMS
Arabidopsis At1g23310 (290) KGYWGECGQRGGYFEMTNLPPRVVEEIYKVASIALSPNVSAQIFMGLMVN
Arabidopsis At1g70580 (290) KGYWGECGQRGGYFEMTNIPPRTVEEIYKVASIALSPNVSAQIFMGLMVS
           Capsicum (298) KGFYGECGKRGGYMEITGFSPEVREQIYKLASVNLCSNISGQILASLVMS
                          351                                                400
     Barley alaAT   (349) PPKASDESYASYKAEKDGILASLARRAKALEHAFNKLEGITCNEAEGAMY
      P. miliaceum  (349) PPKVGDESYAAYKAEKDGILQSLARRAKALEDAFNNLEGISCNKAEGAMY
        Rice alaAT1 (349) PPKAGDASYASYKAEKDGILQSLARRAKALENAFNSLEGITCNKTEGAMY
        Rice alaAT2 (347) PPKAGDESYESFMVEKDGILSSLARRAKALEEAFNSLEGITCNKAEGAMY
        Rice alaAT4 (342) PPKVGDESYPSYRAERDSILSSLSCCAEAMVSTFNSMEGMTCNKAEGGIS
        Rice alaAT3 (349) PPKLGDEAFEIFMVEKEETYSSLLKRAKALQKAFNGLEGVSCNKFEGAMY
             Maize  (349) PPKAGDESYASYKAEKDGILESLARRAKALEDAFNKLEGFSCNKAEGAMY
Arabidopsis At1g17290 (349) PPKPGDDSYESYIAEKDGILSSLARRAKTLEEALNKLEGVTCNRAEGAMY
Arabidopsis At1g72330 (349) PPKPGDDSYDSYMAERDGILSSMAKRAKTLEDALNSLEGVTCNRAEGAMY
Arabidopsis At1g23310 (340) PPKPGDISYDQFARESKGILESLRRRARLMTDGFNSCKNVVCNFTEGAMY
Arabidopsis At1g70580 (340) PPKPGDISYDQFVRESKGILESLRRRARMMTDGFNSCKNVVCNFTEGAMY
           Capsicum (348) PPKVGDESYESFSAEKEAVLSSLARRAQALQDALNSLEGVTCNRAEGAMY
```

FIGURE 3, cont., part C

```
                            401                                               450
        Barley alaAT  (399) VFPQICLPQKAIEAAKAANKAPDAFYALRLLESTGIVVVPGSGFGQVPGT
         P. miliaceum (399) LFPQIHLPKKAIEAAKAANKAPDAFYALRLLESTGIVVVPGSGFGQVPGT
           Rice alaAT1 (399) LFPQLSLPQKAIDAAKAANKAPDAFYALRLLEATGIVVVPGSGFGQVPGT
           Rice alaAT2 (397) LFPRIYLPQKAIGAAQAAGTAPDAYYARRLLEATGIVVVPGSGFGQVPGT
           Rice alaAT4 (392) VFPSVRLPPRAIEAAEAMNTEPDVFYALRLLESTGIVVVPGSVFGQVPGT
           Rice alaAT3 (399) LFPRLRLPQAAIKAAQLEGVSPDVFYAHRLLDATGIAVVPGSGFHPVSGT
                Maize  (399) LFPQIHLPQKAIEAAKAAKKAPDAFYALRLLESTGIVVVPGSGFGQVPGT
  Arabidopsis At1g17290 (399) LFPCLHLPQKAIAAAEAEKTAPDNFYCKRLLKATGIVVVPGSGFRQVPGT
  Arabidopsis At1g72330 (399) LFPRINLPQKAIEAAEAEKTAPDAFYCKRLLNATGVVVVPGSGFGQVPGT
  Arabidopsis At1g23310 (390) SFPQIRLPTGALQAAKQAGKVPDVFYCLKLLEATGISTVPGSGFGQKEGV
  Arabidopsis At1g70580 (390) SFPQIKLPSKAIQAAKQAGKVPDVFYCLKLLEATGISTVPGSGFGQKEGV
              Capsicum (398) LFPRINLPDKAIKAAEVAKTAPDAFYAKLLLNATGIVVVPGSGFRQVPGT
                            451                       484
        Barley alaAT  (449) WHFRCTILPQEDKIPAVISRFTVFHEAFMSEYRD
         P. miliaceum (449) WHIRCTILPQEDKIPAVITRFKAFHEAFMAEYRD
           Rice alaAT1 (449) WHIRCTILPQEEKIPAIISRFKAFHEGFMAAYRD
           Rice alaAT2 (447) WHFRCTILPQEDKIPAIISKFKEFHEKFMDEFRD
           Rice alaAT4 (442) WHFRCTILPQEEKTRQIISRFNVFHEAFMEEFRS
           Rice alaAT3 (449) SHIRCTILPGEETITAMVPSLQAFHEAFMDEFRG
                Maize  (449) WHIRCTILPQEDKIPAVISRFRAFHEAFLAEYRD
  Arabidopsis At1g17290 (449) WHFRCTILPQEDKIPAIVDRLTAFHQSFMDEFRD
  Arabidopsis At1g72330 (449) WHFRCTILPQEDKIPAIVNRLTEFHKSFMDEFRN
  Arabidopsis At1g23310 (440) FHLRTTILPAEDEMPEIMDSFKKFNDEFMTQYDN
  Arabidopsis At1g70580 (440) FHLRTTILPAEEEMPEIMDSFKKFNDEFMSQYAD
              Capsicum (448) WHFRCTILPQEEKIPAIVSRLTEFHKKFMDEFCG
```

FIGURE 4

OsAnt1 regulatory region

```
     Primer 1
  1  AGGAAGTGAT TTTTAGCGTA GCTGTGTTTG TAGCGTAATT GCGTAAAGTC CTTTCAATTT

61  TGCTATATCT CACTCGAAAG ATTTTTTCTT ATCTCTCACT CGATTTCTC  ACTCAAATTT

121  ACAGTGTATT TTCTTGTAAG TTACAGTGTA ATTTATGAAA CTTACACTGT AACTTTTGTA

181  AGTTACACTG TAATTTTTGA ATCTTCACAT GTAAATTTTA AATTTTGTAT TGGATTTGGT

241  CTTTTTCTTG AGGATATGGT AATTTAATGT TCATTATGGT GTTTCTTAAT TGCTTTTTGC

301  TTTTTATTAT ATCTATCGGA TTTTAATACA AAGATTAAAA ATCTGTGTGA TACGATTATA

361  AAAATCTTTC GAAAGATGTA TAGGTACTCC CAAGCCCTTT TAAGAAAGTT TTTCAAGACA

421  AAAGTTTTTG GATGAAAGGT AGTTATAGGG AAAAAGGAAT GTGCGTTTAT GTTTATTTGC

481  ATTGCTTATT AGCAACCAAA AACTAATCTA TAAGTAAATC TTTTATATAC GTGCGCTTAA

541  TAATTCAAAA GCAAATTCAT GTAAAATAAA AGCGATGAA  GAAACTTTAA AAAGTTATCA

601  AATTTAGATT TTATTAAATT TTAGTTTACA AGAGCGCTAC GATGAAGGCT TTAAAAAGAT

661  GGGAAAATAA AACCTTTGAC CTTTCTGGAC TTCACCAAAC AGCTCACGCT TTCGGCTTCG

721  TGCCGTCTCG TCCCGTGCTA CTGCTACCCC CTCCTGACCC CACCCGCCAC TCCACGCTCC

781  CTTCTCCTCC CCTTCCCGTG ACACACAGTC CCCACTCCAC CGCCTCCGTA TAAGTATCCC

841  TTCCTTACCG CCGGCCAGCC ACAGCCACCG CCTCCCCAC  CCCACCCCGA TCCCCTCCCC

901  GCCGTACGGG CGCAGAAGGA ACCCGTCTTC TAGAAGGAGG AGGAGGGCTA CCTCTCTCTC

961  TCTCTCTTCT GCC
                 Primer 2
```

Schematic Representation of the Steps for Producing the OsAnt1pro-Gus Construct

Schematic Representation of the Steps for Producing the OsAnt1pro-AlaAT Construct

FIGURE 7
Expression of the GUS Reporter Gene
Directed by the OsAnt1 Promoter
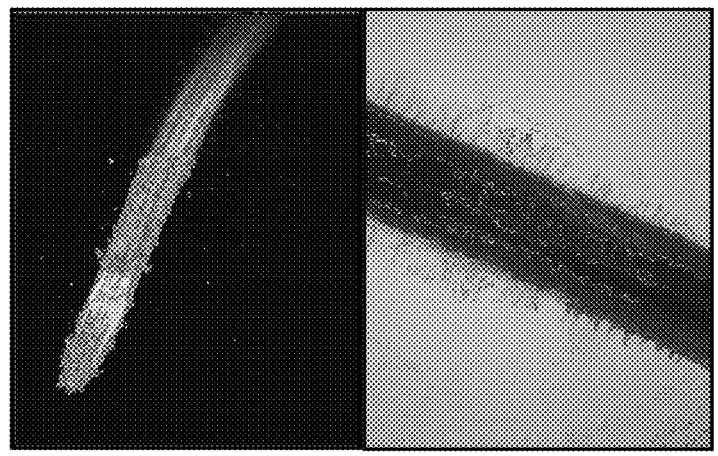
A
Developing Roots
B
Root Hairs
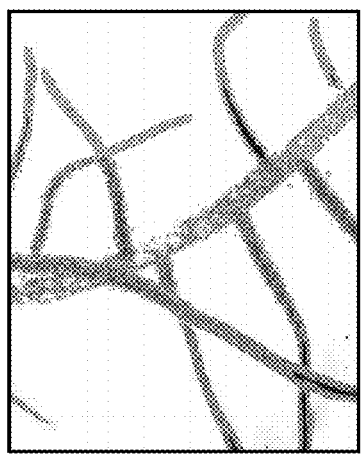
C
Lateral Roots Average Dry Weight Biomass of *Oryza sativa* Plants
Transformed with OsAnt1pro-AlaAT

Average Total Seed Weight of *Oryza sativa* Plants Transformed with OsAnt1pro-AlaAT Relationship between Dry Weight Biomass and Total Seed Weight of *Oryza sativa* Plants Transformed with OsAnt1pro-AlaAT

FIGURE 11

Sorghum Ant promoter

```
  1 GATTCGACAA TATTTATCAA ATAAAAACGA AAATACTACA TTAGTGAAAT CTGAATTTTT
 61 TTTCGAACTA AACAAGGCCC AAGACACAGA ACGTGCACAC GCAAAGCTGG CGTTCAATGA
121 TACGTATAAT GATAAAATTA TATTTGTTGT ATTTTTTAAA CCTACAAACA CGCCACGCCC
181 ATGCCCACGC CCACGCTTTC GTCTCGTCTC GTCCCGTGAA CAAACAACAA CAGTACAGCA
241 GCAGCACCCA CCGCACCACC ATTCCTCCGC GCCCAGCCTC CTTCGTCTCC TTCCCTCCCG
301 GAGCAGTTCA CAGTCCCCAC TCCACCTCCT CCTACAAATA CACCTCACTA CTTCACCACG
361 CCTCTGCTCC CCTGCCTTCC GCTTCCCTCC CTATCCCCCC CACCCCCCCG CATCGTACGG
421 AACCTGCCAA CGCCGCCGGC GCC
```

FIGURE 12

Maize Ant promoter

```
  1  TCTGTCCCGT GAACAAACAA ACGGCAAGGC CGTCCAACCG TACCACTCCT CCGCGCCGGG
 61  CCCGGGCTCC ATCGCCTTCC CGGAGCAGTT CACAGTCCCC ACTCCACCTC CTTCTACAAA
121  TACACCTCAG TCTCAGCCCC CCACCACATC CGCTCCCCGC CTTCCGCTTC CCTACCCCCC
181  GCATCACCTA CCAACGCCGG CGCC
```

NITROGEN-EFFICIENT MONOCOT PLANTS

CROSS REFERENCE TO RELATED APPLICATIONS

This application is a Divisional of U.S. application Ser. No. 11/644,321, filed Dec. 21, 2006, now U.S. Pat. No. 8,288,611, which claims the benefit of U.S. Application No. 60/753,818, filed Dec. 23, 2005, the contents of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 595792001110SeqListing.txt, date recorded: Dec. 11, 2012, size: 73 KB).

FIELD OF INVENTION

The invention relates to monocot plants having enhanced nitrogen utilization efficiency (NUE), to methods for enhancing NUE in monocot plants, and to methods of increasing biomass and seed yield in monocot plants grown under nitrogen limiting conditions. This invention also relates to monocot antiquitin promoters.

BACKGROUND OF THE INVENTION

In many ecosystems, both natural and agricultural, the productivity of plants is limited by the three primary nutrients: nitrogen, phosphorous and potassium. The most important of these three limiting nutrients is usually nitrogen. Nitrogen sources are often the major components in fertilizers (Hageman and Lambert, I. Corn and Corn Improvement, 3rd ed., Sprague & Dudley, American Society of Agronomy, pp. 431-461, 1988). Since nitrogen is usually the rate-limiting element in plant growth, most field crops have a fundamental dependence on inorganic nitrogenous fertilizer. The nitrogen source in fertilizer is usually ammonium nitrate, potassium nitrate, or urea.

Each year, approximately 85 to 90 million metric tons (MMt) of nitrogenous fertilizers are added to the soil worldwide. This is up from only 1.3 MMt in 1930 and from 10.2 MMt in 1960. It is predicted to increase to 240 MMt by the year 2050 (Tilman et al., Proc. Nat. Acad. Sci. USA. 96: 5995-6000, 1999). It is estimated that 50% to 70% of the applied nitrogen is lost from the plant-soil system. Because NO3- is soluble and not retained by the soil matrix, excess NO3- may leach into the water and be depleted by microorganisms. In fact, most of the applied nitrogen is rapidly depleted by soil microorganisms, leaching, and other factors, rather than being taken up by the plants.

Increased nitrogen utilization efficiency by plants would have a number of beneficial effects. For example, nitrogen utilization efficient plants would be able to grow and yield better than conventional plants in nitrogen poor soils. The use of nitrogen efficient plants would reduce the requirement for the addition of nitrogenous fertilizers to crops. Since fertilizer application accounts for a significant percentage of the costs associated with crop production, such a reduction in fertilizer use would result in a direct monetary savings.

A reduction in fertilizer application would also lessen the environmental damage resulting from extensive nitrogenous fertilizer use. These detrimental effects of nitrogenous fertilizer use on the environment are manifested in increased eutrophication, acid rain, soil acidification, and the greenhouse effect.

Monocots represent a large percentage of the crops grown on the world's 3.7 billion acres of cultivable land. In the United States alone, over 80 million acres of maize, 59 million acres of wheat, 4 million acres of barley and 3 million acres of rice were planted in 2004.

Given the worldwide requirements for monocots and the diminishing fertility of existing fields, it is desirable to generate monocot plants that are able to grow under suboptimal nutrient conditions. One means for accomplishing this goal is to generate monocot plants that can utilize nitrogen more efficiently. Such monocot plants would have the advantage of being able to grow in soils that are poorer in nitrogen, as a result of being able to more efficiently use the nitrogen that is available. Additionally, such monocot plants may demonstrate enhanced productivity in soils that have normal nitrogen levels as well.

Rice is routinely used as the model crop for genetic and physiological studies in other monocot crops including maize, wheat, sugarcane, barley, sorghum, rye and grass. Because of its importance as a model crop, rice was the first crop plant to be sequenced. The International Rice Genome Sequencing Project, a consortium of publicly funded laboratories, completed the sequencing of the rice genome in December 2004. Rice has a small, diploid genome that is well conserved and syntenic across monocots. It is easily transformed and transgenic studies have been performed in rice to study a number of phenotypic traits, including flowering, abiotic stress response, disease resistance, drought tolerance, and morphological development.

Because of the critical importance of nitrogen to plant growth, previous studies have attempted to increase the efficiency of nitrogen utilization in plants using a variety of means. These methods have included conventional breeding programs directed toward the development of plants that are more efficient at nitrogen utilization. Recombinant deoxyribonucleic acid (DNA) and transgenic plant methods have also been employed in an attempt to generate nitrogen efficient plants.

A variety of different genes have been over expressed in dicot plants to increase nitrogen use efficiency with variable results (for review, see Good et al., Trends Plant Sci 9:597-605, 2004). However, monocots and dicots differ from each other in many ways including morphologically, developmentally, metabolically, phenotypically, and genetically. Because of these numerous differences, it would not be predictable that successful whether successful approaches to increase nitrogen utilization efficiency in dicots would necessarily work in monocots.

In the dicot canola, over expression of the enzyme alanine aminotransferase (AlaAT) under the direction of the *Brassica* turgor gene-26 (also known as antiquitin) promoter elevates AlaAT levels and increases NUE (U.S. Pat. No. 6,084,153). However, whether over expression of AlaAT would increase NUE in monocot plants has not been previously reported.

Increasing NUE within monocot plants is desired within the art.

SUMMARY OF THE INVENTION

The invention addresses the need for monocot plants with enhanced growth characteristics and nitrogen utilization efficiencies when grown under low nitrogen conditions by providing such plants and methods for generating transgenic monocot plants with elevated levels of AlaAT.

In one aspect, the invention provides transgenic monocot plants including a recombinant DNA sequence encoding an AlaAT. The transgenic monocot plant may be barley, rice, sugar cane, maize, sorghum, rye, wheat, or grass. Grass includes lawn, turfgrass, forage and the like. Preferably, the AlaAT is operably linked to a promoter, most preferably, a monocot antiquitin promoter. Seeds from the transgenic monocot plants are also provided.

In other embodiments, transgenic rice, maize, wheat, sorghum, barley, and sugar cane include a recombinant DNA sequence encoding an AlaAT and seeds therefrom.

In another aspect of the invention, a method of producing a transgenic monocot plant is provided including the steps of: (1) selecting a nucleic acid encoding an AlaAT, (2) selecting a promoter that is operable in a monocot plant, (3) coupling the selected nucleic acid to the selected promoter to form a genetic construct, (4) transforming a monocot plant cell with the genetic construct to form a transformed cell, and (5) growing a transgenic monocot plant from the transformed cell to produce a transgenic plant. In this embodiment, overexpression of AlaAT causes at least a 5% to 7.5%, 7.5 to 10%, 10 to 15% or 15 to 20%, or more increase in plant biomass and/or seed yield when expressed in a transgenic monocot plant compared to the plant biomass or seed yield of a comparable monocot plant not expressing this construct when the plants are grown under suboptimal nitrogen conditions.

In other embodiments of the invention, a similar methods of producing transgenic rice, maize, wheat, and sorghum plants are provided.

In yet another aspect of the invention, transgenic monocot plants are described wherein the transgenic monocot plant expresses a recombinant AlaAT and exhibits at least a 5% increase in plant biomass or seed yield compared to biomass or seed yield of a comparable plant lacking the recombinant AlaAT. Also described are seeds produced from the transgenic monocots. The monocots include but are not limited to, maize, wheat, rice, barley and rye.

A method for increasing biomass of a monocot plant by contacting and introducing into a plant an AlaAT coding region in operative linkage with monocot antiquitin promoter is described. Similar methods for increasing seed yield of a plant and are also provided.

The nucleic acids encoding AlaAT that are used in the genetic constructs of these inventions may be derived from any organism preferably a plant, and most preferably from a monocot plant including, but not limited to, barley, rice, sugar cane, rye, wheat, maize, or grass.

In yet another aspect, the invention provides an isolated monocot antiquitin promoter sequence. The monocot promoter sequence may be from barley, rice, sugar cane, maize, sorghum, rye, wheat, or grass. In certain embodiments, it is a sorghum promoter that includes SEQ ID NO: 9 or an active fragment thereof. In other embodiments, it is a maize promoter that includes SEQ ID NO: 10 or an active fragment thereof.

Also provided are methods of directing expression of a target gene by contacting and introducing into a plant a target gene in operative linkage with a monocot antiquitin promoter.

Also described are genetic constructs, transformed plants, and plant seeds including a monocot antiquitin promoter sequence operatively linked with a target gene. Preferably, the target gene encodes a nitrogen utilization protein, such as, for example, a high affinity nitrate transporter, a low affinity nitrate transporter, an ammonium transporter, an ammonia transporter, an amino acid transporter, alanine dehydrogenase, glutamine synthetase, asparagine synthetase, glutamate synthase, glutamate 2:oxogluturate amino transferase, asparaginase, glutamate dehydrogenase, nitrate reductase, aspartate aminotransferase, or AlaAT.

BRIEF DESCRIPTION OF THE DRAWINGS

FIG. 2 parts A-D show an alignment of the amino acid sequences (SEQ ID NO:s 29 to 45) of AlaAT from various organisms. Note that some of sequences used for these alignments are truncated sequences which contain less than the complete sequence of the cited AlaAT. The alignment was performed using the methionine (M) of the barley AlaAT sequence as the reference first residue.

FIG. 3 parts A-C show an alignment of the amino acid sequences (SEQ ID NO:s 29 to 40) of AlaAT from various plant species. Note that some of sequences used for these alignments are truncated sequences that contain less than the complete sequence of the cited AlaAT. The alignment was performed using the methionine (M) of the barley AlaAT sequence as the reference first residue.

FIG. 4 shows the nucleotide sequence for the OSAnt1 promoter of the invention (SEQ ID NO:1). The sequence was isolated using a blastn search of the National Center for Biotechnology Information (NCBI) database using the nucleotide sequence (366-3175 bp) of the *Brassica* btg26 gene (Stroeher et al., 1995, *Plant Mol. Biol.* 27:541-551) to identify the homologous rice nucleotide sequence (accession number AF323586). This sequence was then used in turn against the TIGR *Oryza sativa* sequencing project (see: tigr.org/tdb/e2k1/osa1/), as set out in Example 1. The putative TATA box is shown in bold and the primers used in PCR amplifying the sequence from the rice genome are underlined.

FIG. 7 shows expression of the GUS reporter gene directed by the OsAnt1 promoter of the invention. Expression is present in the cell expansion area of root tips of developing roots (panel A); in root hairs of developing roots (panel B); and in lateral roots of roots (panel C) of an *Oryza sativa* plant transformed with the genetic construct OsAnt1pro-Gus as shown in FIG. 5, in accordance with the method described in Example 1. Darkly stained areas indicate expression of the GUS reporter gene.

FIG. 11 shows the nucleotide sequence of the sorghum antiquitin promoter of the invention (SEQ ID NO:9). The sequence was derived from accession CW033386 as described in Example 5 and includes 443 nucleotides of sequence upstream of the ATG start codon of a sorghum antiquitin gene.

FIG. 12 shows the nucleotide sequence of a partial maize antiquitin promoter (SEQ ID NO:10). The sequence was derived from accession BH215004 as described in Example 5 and contains 204-bp upstream of a maize antiquitin gene.

DETAILED DESCRIPTION

Monocot plants having enhanced NUE, methods for enhancing NUE in monocot plants, and methods of increasing biomass and seed yield in monocot plants grown under nitrogen limiting conditions are described herein. Limiting nitrogen conditions are conditions under which the plant biomass or seed yield are reduced as a result of reduced nitrogen levels. Under such conditions, the plant biomass or seed yield can be increased by increasing the amount of available nitrogen by fertilization or other means. Limiting conditions are also known as suboptimal conditions.

Figure 1:
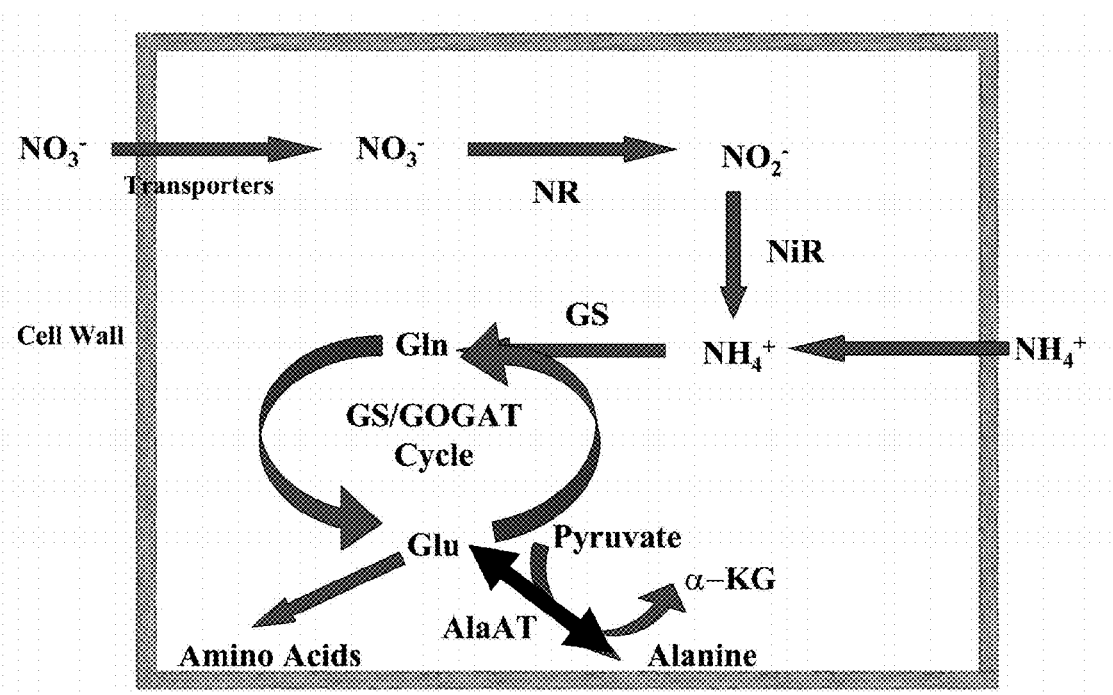
FIG. 1 shows a schematic representation of the key steps in nitrogen utilization in a plant cell. Nitrate ($NO_3^-$) is transported into the plant cell and converted to nitrite ($NO_2^-$) by nitrate reductase (NR). Nitrite is translocated from the cytoplasm to the chloroplast where it is reduced by nitrite reductase (NiR) to ammonium ($NH_4^+$). Glutamine synthetase (GS) functions in assimilating or recycling ammonium. An enzyme couple glutamine synthetase (GS)/glutamate synthase (GOGAT) catalyzes the conversion of glutamine (Gln) to glutamate (Glu). Glutamate is a building block of many amino acids. In addition, alanine is synthesized by the enzyme AlaAT from pyruvate and glutamate in a reversible reaction.

Nitrogen assimilation and metabolism in plants occurs through the coordinated action of a variety of enzymes acting upon a variety of substrates (FIG. 1). Nitrogen assimilation occurs primarily through the activities of glutamine synthetase (GS) and glutamate synthase (GOGAT). From the GS-GOGAT cycle, glutamate is used as a nitrogen source to supply nitrogen for other required metabolic reactions. The metabolic flow of nitrogen is principally mediated by transamination reactions in which an amino group of glutamate is transferred to other carbon skeletons. The transfer of the amino group from glutamate to these other carbon skeletons results in the disposition of nitrogen in more readily usable forms such as other amino acids like aspartate or alanine. Examples of such enzymes are the aminotransferases. FIG. 1 shows the reaction catalyzed by the enzyme AlaAT which catalyzes the transfer of an amino group from glutamate to pyruvate thus generating alanine.

While not limiting the invention to a particular mechanism, it is believed that over expression of AlaAT increases nitrogen efficiency by depleting the available pools of nitrogen storing amino acids such as glutamate, which in turn leads to upregulation of the uptake and assimilation pathways in the plant. By transferring an amino group from glutamate to pyruvate, the action of AlaAT depletes the pools of glutamate, a nitrogen storage compound. Moreover, the pool of alpha-ketoglutarate is replenished. To compensate for glutamate depletion, the plant increases uptake and assimilation of nitrogen to restore the balance. The increased uptake and assimilation activity allows the plant to more effectively utilize lower (suboptimal) levels of nitrogen present in the soil.

Monocot antiquitin promoters, such as rice, sorghum, and maize, are also described herein for use with any type of coding regions of interest.

DEFINITIONS

The language "transgenic" refers to a monocot plant that contains an exogenous nucleic acid molecule that can be derived from the same monocot plant species, from a heterologous plant species, or from a non-plant species.

A "promoter" is a regulatory nucleic acid sequence, typically located upstream (5') of a gene or protein coding sequence that, in conjunction with various cellular proteins, is responsible for regulating the expression of the gene or protein coding sequence. Such promoters can be the full length promoter or active fragments thereof. By "active fragment" is meant a fragment that has at least about 0.1%, preferably at least about 10%, and more preferably at least about 25% of the activity of a reference promoter sequence as tested via methods known to those of skill in the art for detecting promoter activity, e.g., measurement of GUS reporter gene levels. DNA sequences necessary for activity can be identified by synthesizing various fragments and testing for expression or introducing point mutations in certain regions and testing for loss of activity.

Heterologous fragments of promoters or other promoter sequences may be combined to mediate the activity of a promoter sequence. For example, the CaMV 35S promoter or other known promoter sequences may be combined with the promoter sequence described herein to mediate expression of a coding region of interest.

The language "coding region of interest" or "target gene" includes any gene that is desirably expressed in one or more than one plant tissue. Likewise, a "target protein" refers to any protein that is desirably expressed in one or more than one plant tissue. Examples of a coding region of interest which may advantageously be utilized in conjunction with the methods described herein include nucleic acid sequences that encode one or more than one protein involved in nitrogen assimilation, nitrogen utilization, nitrogen uptake or a combination thereof.

The term "elevated levels" of a protein of interest, as used herein in reference to protein levels in a transgenic monocot plant, means higher levels of protein as compared to the protein levels of a corresponding monocot plant variety lacking the transgene such as an over expressed nucleic acid molecule encoding an AlaAT.

The gene constructs described herein can also include further enhancers, either translation or transcription enhancers, as may be required. These enhancer regions are well known to persons skilled in the art and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region or from the structural gene. The sequence can also be derived from the promoter selected to express the gene and can be specifically modified to increase translation of the messenger ribonucleic acid (mRNA).

The gene constructs of the invention can further include a 3'-untranslated (or terminator) region that contains a polyadenylation signal and other regulatory signals capable of effecting mRNA processing or gene expression. Nonlimiting examples of suitable 3'-regions are the 3'-transcribed non-translated regions containing a polyadenylation signal of *Agrobacterium* tumor-inducing (Ti) plasmid genes such as the nopaline synthase (Nos gene), plant genes such as the soybean storage protein genes, and the small subunit of the ribulose-1,5-bisphosphate carboxylase (ssRUBISCO) gene.

By "operatively linked" or "operative linkage" it is meant that the particular sequences interact either directly or indirectly to carry out an intended function, such as mediation or modulation of gene expression. The interaction of operatively linked sequences may be mediated, for example, by proteins that interact with the operatively linked sequences.

The term "exogenous" as used herein in reference to a nucleic acid molecule means a nucleic acid molecule originating from outside the plant. An exogenous nucleic acid molecule can have a naturally occurring or non-naturally occurring nucleotide sequence. One skilled in the art understands that an exogenous nucleic acid molecule can be a heterologous nucleic acid molecule derived from the same plant species or a different plant species than the plant into which the nucleic acid molecule is introduced. Alternatively, it can be a nucleic acid molecule derived from a non-plant species such as fungi, yeast, bacteria or other non-plant organisms.

The following description is of a preferred embodiment.

Overview of Alanine Aminotransferases (AlaATs)

As a general class of enzymes, aminotransferases are pyridoxal phosphate-dependent enzymes that catalyze reactions known as transamination reactions. The transamination reaction catalyzed by aminotransferases involves the transfer of an α-amino group from an amino acid to the α-keto position of an α-keto acid. In the process, the amino acid becomes an α-keto acid while the α-keto acid acceptor becomes an α-amino acid. The specific aminotransferase, AlaAT, utilizes glutamate as the amino group donor and pyruvate as the amino group acceptor. Transamination of pyruvate to form alanine is found in virtually all organisms. Accordingly, enzymes with AlaAT activity are also found in virtually all organisms as well. This group of AlaATs forms a basis for the isolation and selection of the AlaATs of the invention.

Identification of AlaATs

Because most organisms possess AlaAT activity and enzymes, a number of methods can be used to identify and isolate these sequences from different species. Given the strong correlation between structure and function, one may use knowledge of the sequences of known members of the AlaAT family to collect additional family members that can serve as candidate AlaATs for use in the invention.

Database searching: One method that can be used to generate a group of AlaAT sequences for use in the invention is database searching. Because the genomes of a number of organisms have been sequenced, computer-based database searching based on amino acid or nucleic acid homology will reveal sequences which are homologous to a known AlaAT that is used as the query sequence. One common tool for such computer database searching is the BLAST program available from the NCBI. The NCBI Basic Local Alignment Search Tool (BLAST) (Altschul et al., *J. Mol. Biol.* 215(3): 403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website. A description of how to determine sequence identity using this program is available at the NCBI website. An example of using a BLAST program to identify members of the AlaAT family is described in Example 7. The use of computer programs such as Softberry and PSORT can be used to determine the subcellular localization of these enzymes to exclude enzymes that are targeted to less optimal sites, i.e., to the peroxisome.

Among the methods for sequence alignment which are well known in the art are the programs and alignment algorithms described in: Smith and Waterman, *J. Mol. Biol.* 147 (1):195-197, 1981; Needleman and Wunsch, *J. Mol. Biol.* 48(3):443-453, 1970; Pearson and Lipman, *Proc. Natl. Acad. Sci. U.S.A.* 85(8):2444-2448, 1988; Higgins and Sharp, *Gene* 73(1):237-244, 1988; Higgins and Sharp, *Comput. Appl. Biosci.* 5(2):151-3. (1989); Corpet, *Nucleic Acids Res.* 16(22): 10881-90, 1988; Huang et al., *Comput. Appl. Biosci.* 8(2): 155-65, 1992; and Pearson et al., *Methods Mol. Biol.* 25:365-389, 1994. Altschul et al. (*Nature Genet.* 6(2):119-129, 1994) present a detailed consideration of sequence alignment methods and homology calculations.

Depending upon the extent and placement of regions of homology, homologous sequences, identified using computer-based search methods such as those described above, can be reasonably suspected of encoding an AlaAT. Whether such a sequence actually encodes an AlaAT can be determined by a number of means. As a first indicator, the annotation to a GenBank entry is used. Many sequences have been previously identified and tested by investigators as corresponding to AlaAT activity and the annotation to such a GenBank entry would so indicate.

Alternatively, a sequence identified from a search can be tested experimentally to determine if it encodes an AlaAT activity. In the case of a nucleic acid sequence that has been identified, it can be isolated for testing using a variety of methods known in the art. For example, the sequence of interest can be amplified by polymerase chain reaction (PCR) using primers that correspond to the 5' and 3' ends of the complementary DNA (cDNA). Such PCR methods are well known in the art and are disclosed in sources such as the laboratory manual PCR Protocols: A Guide to Methods and Applications by M. Innes, et al., Academic Press, 1989. Alternatively, the desired sequence can be obtained by conventional hybridization screening using oligonucleotides corresponding to the known nucleic acid sequence to screen a cDNA library. Screening methods based on hybridization are well known in the art and are disclosed in Sambrook, Fritsch and Maniatis, MOLECULAR CLONING: A LABORATORY MANUAL, 2nd edition, 1989; CURRENT PROTOCOLS IN MOLECULAR BIOLOGY (F. M. Ausubel et al., eds., 1987).

Once a DNA sequence encoding the candidate AlaAT has been obtained, it can be cloned into a variety of expression vectors using conventional molecular biological methods to verify that an AlaAT has been isolated.

The AlaAT coding region can be modified in any suitable way. For example, it can be modified to be transcribable and translatable in the plant system; for example, the nucleotide sequence encoding the AlaAT protein can be modified such that it contains all of the necessary poly-adenylation sequences, start sites and termination sites which allow the coding sequence to be transcribed to mRNA and the mRNA to be translated in the monocot plant. Further, the coding region may be modified such that its codon usage is more similar to that of native genes of the monocot plant (i.e., plant optimized sequence may be used). Such nucleotide sequence modifications and the methods by which they may be made are well known to one of skill in the art.

Many vectors for protein expression in *E. coli*, yeast, mammalian cells, or plants are commercially available. Expression of such a construct containing an AlaAT in an appropriate host cell, such as an *E. coli*, using a plamid such as pET vectors available from Novagen (www.Novagen.com), will reveal if the plasmid encodes an AlaAT activity. Methods for assaying for AlaAT activity are well known in the art. One such method is disclosed in U.S. Pat. No. 6,084,153, which is hereby incorporated by reference in its entirety. In this method, leaf tissue is weighed and then ground with sand in a mortar and pestle in extraction buffer containing 0.1 M Tris-HCl (pH 8.5), 10 mM dithiothreitol, 15% glycerol, and 10% (w/v) PVPP. The extract is clarified by centrifugation at 6000 rpm, and the supernatant was assayed for enzyme activity.

Alanine is added to start the reaction as described. See Good and Crosby, *Plant Physiol.* 90:1305-1309, 1989. This assay can be utilized for other organisms such as bacteria and yeast by simply substituting bacteria or yeast extract for the leaf tissue extract.

Hybridization and PCR methods: Other methods can be used to isolate AlaATs that may be used in the invention. In particular, high, medium, or low stringency hybridization methods can be used to isolate orthologues or homologues of known AlaATs that maybe used in the practice of this invention. Hybridization conditions are sequence dependent and vary according to the experimental parameters used. Generally, stringent hybridization conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (1989) and Tijssen (Hybridization with Nucleic Acid Probes, Part II, pp. 415. Elsevier, Amsterdam, Netherlands, 1993). Examples of factors that affect nucleic acid hybridization include: temperature, salt conditions, the presence of organic solvents in the hybridization mixtures, and the lengths and base compositions of the sequences to be hybridized and the extent of base mismatching. An example of high stringency conditions for hybridizing a probe to a filter-bound DNA is 5×SSC, 2% sodium dodecyl sulfate (SDS), 100 ug/ml single stranded DNA at 55-65° C. overnight, and washing twice in 0.1×SSC and 0.1% SDS at 60-65° C. for 20 minutes.

Reduced stringency conditions can be used to isolate nucleic acid sequences that are related but have mismatches. Examples of such conditions include lowering the hybridization and wash temperatures or raising the salt concentrations of the wash solutions. Protocols for such medium and low stringency hybridization methods can be found in commonly used molecular biology manuals such as the aforementioned Sambrook, et al. and Ausubel, et al. references.

Other methods that can be used to isolate orthologues or homologues suitable for use in the invention include PCR cloning. Unique or degenerate primers can be designed to encode conserved regions in AlaAT nucleotide or amino acid sequences. Such conserved regions can be identified by aligning the sequences of known AlaATs using the alignments disclosed above. The PCR primers so designed can be used in PCR reactions to generate a portion of an AlaAT sequence from a species of interest which then can be used to isolate a full length cDNA by conventional library screening methods or by means of additional PCR methods such as Rapid Amplification of cDNA Ends (RACE). Protocols for such PCR methods are well known in the art and can be found in sources such as PCR Protocols: A Guide to Methods and Applications by M. Innes, et al., Academic Press, 1989.

An alternative strategy for identifying AlaATs for use in the invention entails the biochemical purification of AlaATs from a source of interest based on enzymatic activity. Because enzymatic assays for AlaAT activity are well known in the art, a skilled artisan would be able to fractionate a cell or tissue of interest and use conventional biochemical methods such as chromatography to purify an AlaAT to homogeneity. Such biochemical methods are available in sources such as Protein Purification: Principles and Practice by Robert K. Scopes, Springer Advanced Texts in Chemistry, 3rd edition, 1994; Guide to Protein Purification (Methods in Enzymology Series, Vol. 182, 1990) by Abelson et al., Protein Purification Techniques: A Practical Approach (Practical Approach Series, 2001) by Simon Roe (Ed.). The AlaAT, once purified to homogeneity, can be used to derive partial amino acid sequences, from which oligonucleotides can be designed to clone the corresponding cDNA by conventional molecular biological methods such as library screening or PCR as described above.

FIGS. 2 and 3 and Tables 1 and 2 show alignments between AlaATs from a variety of species, ranging from *E. coli* to humans and including a number of plant species. The percent homologies range from over 90% to under 25% when the sequence of each AlaAT is compared with that of every other AlaAT as shown in Table 1. A number of highly conserved amino acid sequences that are present in all AlaAT sequences are highlighted in black in FIGS. 2 and 3. Such evolutionarily conserved amino acid sequences represent consensus sequences or sequence motifs that are characteristic of AlaATs. Frequently, such sequences form active sites or other functionally significant regions of a protein.

TABLE 1

| | Barley AlaAT | P. miliaceum AlaAT | Rice AlaAT1 | Rice AlaAT2 | Rice AlaAT4 | Rice AlaAT3 | Maize AlaAT | *Arabidopsis* At1g-17290 | *Arabidopsis* At1g-72330 | *Arabidopsis* At1g-23310 |
|---|---|---|---|---|---|---|---|---|---|---|
| Barley AlaAT | 100 | 90 | 89 | 80 | 58 | 60 | 90 | 77 | 78 | 53 |
| P. miliaceum AlaAT | | 100 | 91 | 82 | 60 | 61 | 94 | 78 | 77 | 53 |
| Rice AlaAT1 | | | 100 | 82 | 59 | 62 | 91 | 77 | 76 | 54 |
| Rice AlaAT2 | | | | 100 | 57 | 64 | 81 | 80 | 80 | 53 |
| Rice AlaAT4 | | | | | 100 | 49 | 58 | 56 | 57 | 42 |
| Rice AlaAT3 | | | | | | 100 | 61 | 62 | 61 | 46 |
| Maize AlaAT | | | | | | | 100 | 77 | 76 | 52 |
| *Arabidopsis* At1g-17290 | | | | | | | | 100 | 89 | 52 |
| *Arabidopsis* At1g-72330 | | | | | | | | | 100 | 51 |
| *Arabidopsis* At1g-23310 | | | | | | | | | | 100 |
| *Arabidopsis* At1g-70580 | | | | | | | | | | |
| *Capsicum* AlaAT | | | | | | | | | | |
| *Chlamydomonas* AlaAT | | | | | | | | | | |
| Human AlaAT | | | | | | | | | | |
| Yeast AlaAT | | | | | | | | | | |
| *E. coli* AlaAT | | | | | | | | | | |
| *Thermococcus* AlaAT | | | | | | | | | | |

TABLE 1-continued

|  | Arabidopsis At1g-70580 | Capsicum AlaAT | Chlamydomonas AlaAT | Human AlaAT | Yeast AlaAT | E. coli AlaAT | Thermococcus AlaAT |
|---|---|---|---|---|---|---|---|
| Barley AlaAT | 52 | 76 | 51 | 47 | 46 | 24 | 24 |
| P. miliaceum AlaAT | 52 | 77 | 51 | 47 | 47 | 24 | 24 |
| Rice AlaAT1 | 53 | 76 | 51 | 47 | 46 | 24 | 23 |
| Rice AlaAT2 | 52 | 80 | 50 | 48 | 48 | 25 | 24 |
| Rice AlaAT4 | 42 | 57 | 42 | 38 | 38 | 19 | 19 |
| Rice AlaAT3 | 46 | 63 | 46 | 44 | 42 | 24 | 22 |
| Maize AlaAT | 51 | 76 | 50 | 46 | 47 | 23 | 24 |
| Arabidopsis At1g-17290 | 51 | 81 | 50 | 48 | 44 | 23 | 23 |
| Arabidopsis At1g-72330 | 50 | 82 | 49 | 48 | 45 | 23 | 24 |
| Arabidopsis At1g-23310 | 93 | 51 | 67 | 46 | 44 | 24 | 26 |
| Arabidopsis At1g-70580 | 100 | 51 | 66 | 45 | 45 | 24 | 26 |
| Capsicum AlaAT |  | 100 | 50 | 48 | 46 | 23 | 24 |
| Chlamydomonas AlaAT |  |  | 100 | 47 | 42 | 25 | 26 |
| Human AlaAT |  |  |  | 100 | 44 | 22 | 25 |
| Yeast AlaAT |  |  |  |  | 100 | 19 | 24 |
| E. coli AlaAT |  |  |  |  |  | 100 | 45 |
| Thermococcus AlaAT |  |  |  |  |  |  | 100 |

TABLE 2

|  | Barley AlaAT | P. miliaceum | Rice AlaAT1 | Rice AlaAT2 | Rice AlaAT4 | Rice AlaAT3 | Maize | Arabidopsis At1g-17290 | Arabidopsis At1g-72330 | Arabidopsis At1g-23310 | Arabidopsis At1g-70580 | Capsicum |
|---|---|---|---|---|---|---|---|---|---|---|---|---|
| Barley AlaAT | 100 | 90 | 88 | 80 | 57 | 58 | 90 | 76 | 77 | 51 | 50 | 75 |
| P. miliaceum |  | 100 | 91 | 82 | 59 | 60 | 94 | 77 | 77 | 52 | 51 | 77 |
| Rice AlaAT1 |  |  | 100 | 82 | 58 | 60 | 90 | 76 | 76 | 53 | 52 | 76 |
| Rice AlaAT2 |  |  |  | 100 | 56 | 63 | 80 | 80 | 80 | 51 | 50 | 80 |
| Rice AlaAT4 |  |  |  |  | 100 | 48 | 57 | 54 | 56 | 41 | 40 | 56 |
| Rice AlaAT3 |  |  |  |  |  | 100 | 60 | 61 | 60 | 44 | 44 | 62 |
| Maize |  |  |  |  |  |  | 100 | 76 | 75 | 51 | 50 | 76 |
| Arabidopsis At1g17290 |  |  |  |  |  |  |  | 100 | 89 | 50 | 50 | 81 |
| Arabidopsis At1g72330 |  |  |  |  |  |  |  |  | 100 | 49 | 49 | 82 |
| Arabidopsis At1g23310 |  |  |  |  |  |  |  |  |  | 100 | 93 | 50 |
| Arabidopsis At1g70580 |  |  |  |  |  |  |  |  |  |  | 100 | 50 |
| Capsicum |  |  |  |  |  |  |  |  |  |  |  | 100 |

Overexpression of AlaATs in Monocot Plants

Once an AlaAT has been identified and verified as corresponding to a bona fide AlaAT, a construct for overexpression of the AlaAT in a monocot plant of interest is generated using methods well known in the art. A variety of plasmids are available for this purpose as disclosed below. A variety of promoters such as constitutive promoters, various inducible promoters, or tissue-specific promoters can be used for expression.

Promoters

The promoters suitable for use in the constructs of this invention are functional in monocot plants and in host organisms used for expressing the constructs described. Many plant promoters are publicly known and several examples are listed below. These include constitutive promoters, inducible promoters, tissue- and cell-specific promoters and developmentally regulated promoters. Methods are disclosed below for the selection of promoters that are suitable for use in practicing the invention.

Promoters can be isolated by procedures well known in the art of plant molecular biology. Exemplary, but non-limiting, promoters that can be used in the practice of this invention include: the rice antiquitin (OsAnt1) promoter, which is described in Example 1 below, as well as other antiquitin promoters, as described in Example 5 below; the rice actin 1 (Act-1) promoter, which is described in U.S. Pat. No. 5,641,876; the maize ubiquitin-1 (Ubi-1) promoter, which is described in U.S. Pat. Nos. 5,510,474, 6,054,574, and 6,977,325; the maize alcohol dehydrogenase-1 (Adh1) promoter, which is described in Kyozuka et al., Mol. Gen. Genet. 228 (1-2): 40-48, 1991; and the CaMV 35S and 19S promoters, which are described in U.S. Pat. No. 5,352,605. For other promoters useful in monocots, see: cambia.org website.

One type of promoter particularly useful for expression of a target gene such as AlaAT in a plant is a monocot antiquitin promoter. The rice antiquitin promoter is described in Example 1. Other antiquitin promoters are described in Example 5. Knowing the monocot antiquitin promoters disclosed in these Examples, one of skill could readily identify other monocot antiquitin promoters using methods similar to those described in Example 1 for identification of the rice antiquitin promoter using the btg 26 gene. For example, the sequence can be subject to analysis with a promoter prediction software such as the TSSP plant promoter prediction software found at the softberry.com website to identify likely TATA box sequences and other promoter sequence elements and further analyzed for promoter motifs that may be recognition sites for transcription factors using Signal Scan Software (Prestridge, 1991; available at bimas.dcrt.nih.gov/molbio/signal).

Sequences likely to encode promoters can be confirmed by synthesizing various fragments and testing for expression or introducing point mutations in certain regions and testing for loss of activity using any assay system known to those of skill in the art as being useful for measuring the promoter activity, such as expression of a reporter gene under the control of a promoter sequence. Reporter genes can be any polynucleotide the transcription of which under the control of a promoter sequence, the subsequent translation thereof, or both, can be readily detected by a skilled artisan. The reporter gene does not have to encode a full length protein. In some instances, the reporter gene can even be an oligonucleotide. Most commonly, the reporter gene encodes a protein with detectable activity. Common reporter genes include GUS, luciferase, GFP, beta-galactosidase, CAT, alkaline phosphatase, etc. In preferred embodiments, the reporter gene is GUS.

The expression of the reporter gene can be measured at either the mRNA or protein level using any method known to those of skill in the art. For example, mRNA levels can be detected using a cell-free transcription assay. Alternatively, protein levels can be measured by detecting enzyme activity, using antibodies specific for the protein, or a transcription-translation assay, which allows detection of both the mRNA level and the protein or peptide level.

Promoters from genes that are regulated similarly to the antiquitin genes in plants might also find use in the invention. These genes could be turgor responsive genes that are expressed in root tissues and could be induced by ABA and/or under stress conditions such as drought and salt.

Transformation Methods

After a suitable construct has been made, transgenic plants of interest can be generated using transformation methods well known in the art and described herein as well as in the Examples below. An exogenous nucleic acid molecule can be introduced into a monocot plant for ectopic expression using a variety of transformation methodologies including *Agrobacterium*-mediated transformation and direct gene transfer methods such as electroporation and microprojectile-mediated transformation (see, generally, Wang et al. (eds), Transformation of Plants and Soil Microorganisms, Cambridge, UK: University Press, 1995, which is incorporated herein by reference). Transformation methods based upon the soil bacterium, *Agrobacterium tumefaciens*, are particularly useful for introducing an exogenous nucleic acid molecule into a seed plant. The wild-type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plain host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of co-culturing *Agrobacterium* with cultured plant cells or wounded tissue such as root explants, hypocotyledons, stem pieces or tubers, for example, also are well known in the art (Glick and Thompson, Methods in Plant Molecular Biology and Biotechnology. CRC Press, Boca Raton, Fla., pp 179-20519, 1993). Wounded cells within the plant tissue that have been infected by *Agrobacterium* can develop organs de novo when cultured under the appropriate conditions; the resulting transgenic shoots eventually give rise to transgenic plants that ectopically express a nucleic acid molecule encoding an AlaAT protein. *Agrobacterium* also can be used for transformation of whole seed as described in Bechtold et al., *C. R. Acad. Sci. Paris. Life Sci.* 316:1194-1199, 1993, (which is incorporated herein by reference). *Agrobacterium*-mediated transformation is useful for producing a variety of transgenic seed plants (Wang et al., supra, 1995).

Microprojectile-mediated transformation also can be used to produce a transgenic plant that ectopically expresses AlaAT. This method, first described by Klein et al. (*Nature* 327:70-73, 1987, which is incorporated herein by reference), relies on microprojectiles such as gold or tungsten that are coated with the desired nucleic acid molecule by precipitation with calcium chloride, spermidine or PEG. The microprojectile particles are accelerated at high speed into a plant tissue using a device such as the BIOLISTIC PD-1000 (Biorad, Hercules, Calif.).

Microprojectile-mediated delivery or "particle bombardment" is especially useful to transform plants that are difficult to transform or regenerate using other methods. Microprojectile-mediated transformation has been used, for example, to generate a variety of transgenic plant species, including cotton, tobacco, maize, hybrid poplar and papaya (see Glick and Thompson, supra, 1993) as well as cereal crops such as wheat, oat, barley, sorghum and rice (Duan et al., *Nature Biotech.* 14:494-498, 1996; Shimamoto, *Curr. Opin. Biotech.* 5:158-162, 1994; each of which is incorporated herein by reference). In view of the above, the skilled artisan will recognize that *Agrobacterium*-mediated or microprojectile-mediated transformation, as disclosed herein, or other methods known in the art can be used to produce a transgenic seed plant of the invention.

Alternative gene transfer and transformation methods useful in the invention include, but are not limited to, liposomes, electroporation or chemical-mediated uptake of free DNA, calcium phosphate co-precipitation techniques, and micro- or macroinjection, direct DNA transformation, and may involve Ti plasmids, Ri plasmids, or plant virus vectors. Such transformation methods are well documented in the art.

Growth and NUE Assays

The resulting transgenic plant of interest are tested for expression of the AlaAT transgene and those plant lines that express the AlaAT transgene are tested for the effect of the expressed transgene on plant growth or nitrogen utilization. Suitable tests for monocot plant growth can include a variety of assays such as measuring plant height, seed weight, stem diameter, number of plant leaves, plant biomass as measured in fresh weight or dry weight of roots, leaves, shoots, buds, and flowers, to name but a few such measurement parameters. Tests for NUE can include growth of transgenic plants under different suboptimal nitrogen conditions. Tests may be field test, greenhouse or growth chamber tests or in vitro tests. Plants may be grown hydroponically in Perlite™, other commercially available growing material, soil, or in agar-based media.

Use of Monocot Antiquitin Promoters to Direct Expression of Other Coding Regions Monocot antiquitin promoters can also be used to direct expression of coding regions other than AlaAT.

The coding region of interest, or target gene, operatively linked to the monocot antiquitin promoter may be any nucleotide sequence that is desirably expressed within a plant. General classes of coding regions which may be advantageously employed in the methods and constructs of the invention include nucleotide sequences encoding structural proteins; proteins involved in the transport of nitrogen; proteins involved in the uptake of nitrogen; proteins involved in both the transport and uptake of nitrogen; enzymes and proteins involved in nitrogen utilization; proteins involved in plant resistance to pesticides or herbicides; proteins involved in plant resistance to nematodes, viruses, insects, or bacteria; proteins involved in plant resistance to stress, for example but not limited to osmotic, temperature, pH, or oxygen stress; proteins involved in stimulation or continuation of plant growth; proteins involved in phytoremediation; or proteins having pharmaceutical properties or encoding enzymes which produce compounds having pharmaceutical properties.

For example, the coding region of interest may encode a nitrogen utilization protein and, in particular, an enzyme that assimilates ammonia into amino acids or uses the formed amino acids in biosynthetic reactions. This protein may be selected from, but not limited to, a nitrate transporter (high or low affinity), an ammonium transporter, an ammonia transporter, an amino acid transporter, alanine dehydrogenase, glutamine synthetase (GS), asparagine synthetase (AS), glutamate synthase (also known as glutamate 2:oxogluturate amino transferase and GOGAT), asparaginase (ANS), glutamate dehydrogenase (GDH), nitrate reductase, aspartate aminotransferase (AspAT), AlaAT, and other known aminotransferases. Such proteins are disclosed in US Patent Application Publication Number 2005/0044585, which is hereby incorporated by reference in its entirety.

The target gene or coding region of interest may be naturally expressed in the plant or it may be heterologous to the plant. The gene may originate from any source, including viral, bacterial, plant or animal sources. Preferably, the coding region of interest is heterologous to the monocot antiquitin promoter sequence to which it is operatively linked, in that it is not from the gene the monocot antiquitin promoter sequence is naturally linked to.

The coding region can be modified in any suitable way in order to engineer a gene with desirable properties. The coding region can be modified to be transcribable and translatable in the plant system; for example, the nucleotide sequence encoding the protein of interest can be modified such that it contains all of the necessary poly-adenylation sequences, start sites and termination sites which allow the coding sequence to be transcribed to mRNA (messenger ribonucleic acid) and the mRNA to be translated in the plant. Further, the coding region may be modified such that its codon usage is more similar to that of native genes of the plant (i.e., plant optimized sequence may be used). Such nucleotide sequence modifications and the methods by which they may be made are well known to one of skill in the art.

The methods and constructs described herein allow the production of plants and seeds having expression of one or more desired genes in the plant. There is a wide variety of possible applications of the plants described herein, including, but not limited to, the production of plants having increased stress tolerance, improved nitrogen uptake, improved nitrogen utilization, improved nutrient content, improved nutrient yields of desired compounds, and phytoremediative properties. Specific applications are further described below.

The following examples further demonstrate several preferred embodiments of this invention. While the examples illustrate the invention, they are not intended to limit the invention.

EXAMPLES

Example 1

Demonstration of NUE in Rice Expressing Barley AlaAT

Identification and Characterization of a Rice Antiquitin Promoter (OsAnt1)

The nucleotide sequence (bp 366-3175) of the btg26 gene (Stroeher et al., *Plant Mol. Biol.* 27:541-551, 1995; accession number S77096) was used to search the nucleotide database at NCBI using the blastn search tool. A rice sequence (accession number AF323586) was identified and this nucleotide sequence was used to search the TIGR *Oryza sativa* sequencing project (tigr.org/tdb/e2k1/osa1/). The rice homologue of btg26, *Oryza sativa* antiquitin (OsAnt1), was identified on chromosome 9 of rice (accession number AP005570; 100216-91996 base pairs). A 973-bp sequence (nucleotides 101189-100216 of AP005570) upstream of the start codon of OsAnt1 is shown in FIG. 4 (SEQ ID NO:1).

The sequence of the 403 bps upstream (5') of the ATG start codon of the OsAnt1 gene was selected for further analysis. To determine if the sequence was likely to function as a promoter sequence, the sequence was analyzed using the TSSP plant promoter prediction software found at the softberry.com website. The analysis predicted that the sequence was a plant promoter sequence. The most likely location of the TATA box (bold in FIG. 4), as well as other promoter sequence elements, was determined.

Since the projected OsAnt1 promoter sequence was predicted to contain promoter elements according to the Softberry analysis, the sequences were analyzed for promoter motifs that may be recognition sites for transcription factors using Signal Scan Software (Prestridge, *Comput Appl Biosci* 7(2):203-6, 1991; at bimas.dcrt.nih.gov/molbio/signal). Five different signal sequences were predicted in the OsAnt1 promoter, including ADR1, DBF-A, GAL4, HSTF and RAF transcription factor binding sites.

The OsAnt1 sequence was compared to nucleic acid sequences of btg26 promoter sequences from *Brassica napus* and *Arabidopsis* using the ClustalW 1.8 multiple sequence alignment software on the BCM Search Launcher homepage (searchlauncher.bcm.tmc.edu/) and BOXSHADE server (ch.embnet.org/software/BOX_form.html). Inspection of conserved nucleotides revealed that the *Brassica* and *Arabidopsis* turgor gene-26 promoter sequences are more similar to each other than to the OsAnt1 sequence. A feature among all three promoter sequences (rice, *Brassica, Arabidopsis*) is the polypyrimidine (CT) tracts evident within the nucleotide sequences. These tracts range from 20-22 bases and are found just upstream of the probable TATA boxes in all three promoter sequences. Furthermore, the OsAnt1 sequence has a second polypyrimidine tract just upstream of the ATG start codon.

Cloning of a Rice Antiquitin Promoter

Rice genomic DNA was isolated from cv. Kitaake. The following PCR primers (positions underlined in FIG. 4) corresponding to the OsAnt1 promoter region were selected:

Primer 1:    AGGAAGTGATTTTTAGCGTAGCTG;    (SEQ ID NO: 2)

Primer 2:    ATGGCAGAAGAGAGAGAGAGAGAGG.    (SEQ ID NO: 3)

Touch-down PCR was conducted using rice genomic DNA and the above primers. A 975-bp fragment was produced. The amplified PCR fragment was ligated into pCR®II-TOPO vector (Invitrogen) and transformed into *E. coli*, TOP 10 cells. The resulting plasmid is designated pT-riceOsAnt1pro.

Sequence analysis indicated that the 975-bp PCR fragment encodes a promoter sequence designated the OsAnt1 promoter sequence. Comparison of the OsAnt1 promoter from cv. Kitaake with that of cv. Nipponbare (obtained from the database) revealed that they share 99.9% identity. The putative TATA box was found 145-bps upstream of the start codon.

Production of the OsAnt1pro-GUS Construct

Figure 5:
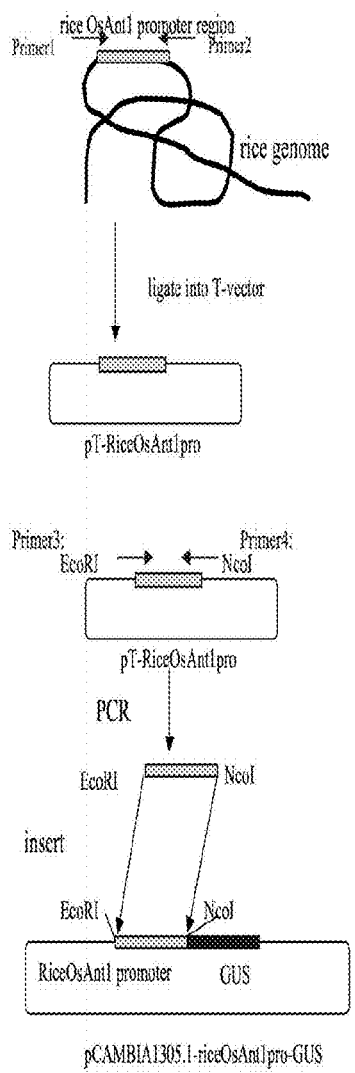
FIG. 5 shows a schematic representation of the steps for producing the genetic construct OsAnt1pro-Gus, using the reporter gene beta-glucuronidase (GUS) in accordance with the method described in Example 1.

The beta-glucuronidase (GUS) reporter gene driven by OsAnt1 was produced using the steps shown schematically in FIG. 5. The RiceOsAnt1pro-GUS construct was produced by amplifying the pT-RiceOsAnt1pro template using the following primers:

Primer 3: EcoRI-OsAnt1 promoter sequence
GGAATTCAGGAAGTGATTTTT    (SEQ ID NO: 4)

Primer 4: NcoI-OsAnt1 promoter sequence
CATGCCATGGATGGCAGAAGA    (SEQ ID NO: 5)

The resultant PCR fragments were ligated into the plant binary vector, pCAMBIA1305.1, digested with EcoR1 and Nco1 to produce a pCAMBIA1305.1-riceOsAnt1pro-GUS construct. The EcoRI and NcoI sequences at the end of primers 3 and 4, respectively, allowed insertion of the PCR fragment into the pCAMBIA1305.1 vector, replacing the existing CaMV35s promoter with the OsAnt1 promoter sequence. The NcoI sequence (CCATGG) includes a Met codon, ATG, which is in frame with the GUS reporter gene and allows expression of the GUS reporter gene from the OsAnt1 promoter sequence.

Production of the OsAnt1pro-AlaAT Construct

Figure 6:
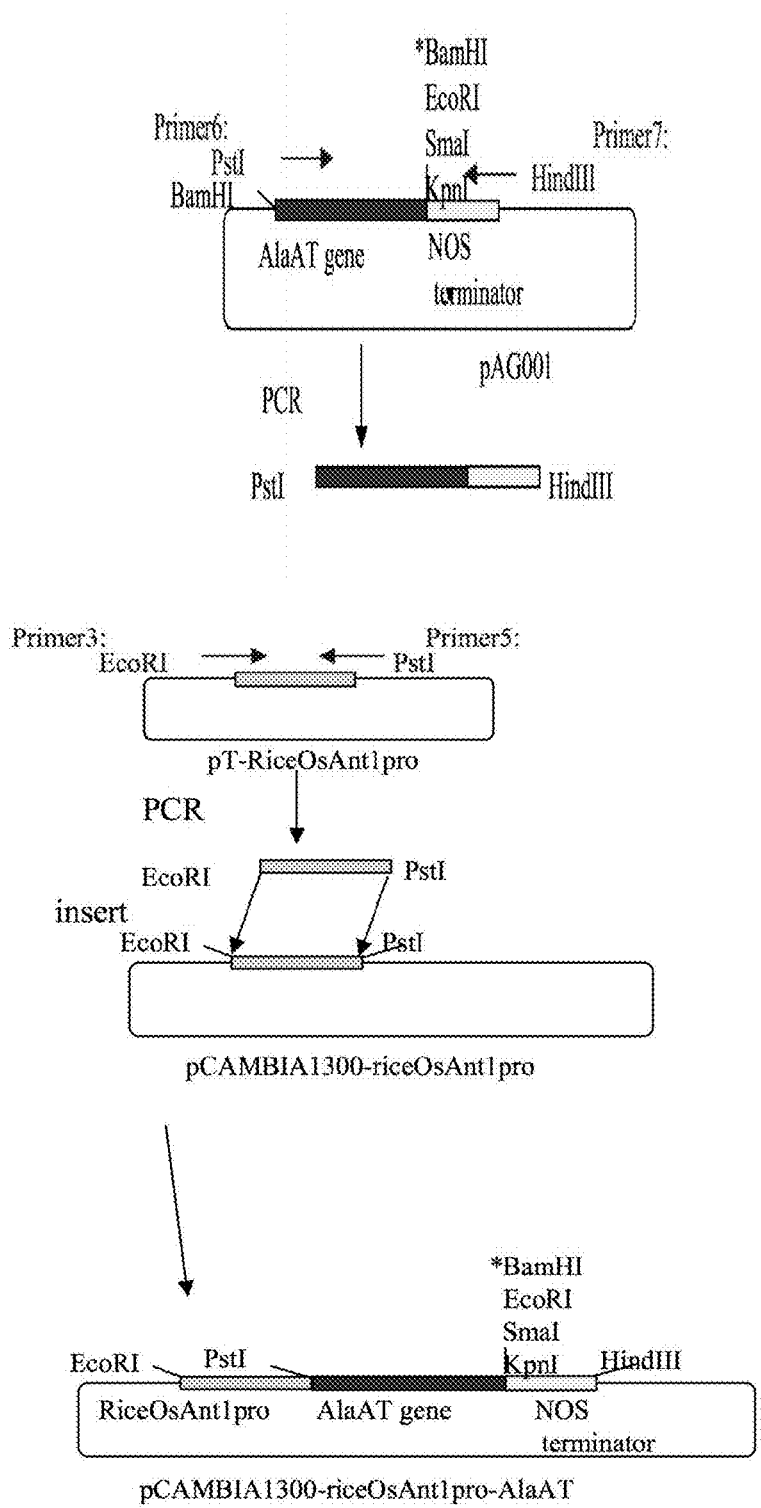
FIG. 6 shows a schematic representation of the steps for producing the genetic construct OsAnt1pro-AlaAT in accordance with the method described in Example 1.

The barley AlaAT gene driven by OsAnt1 was produced using the steps shown schematically in FIG. 6. The RiceOsAnt1pro-AlaAT construct was produced by amplifying the pT-RiceOsAnt1 pro template using the following primers:

Primer 3: EcoRI-OsAnt1 promoter sequence
GGAATTCAGGAAGTGATTTTT    (SEQ ID NO: 4)

Primer 5: PstI-OsAnt1 promoter sequence
AACTGCAGATGGCAGAAGA    (SEQ ID NO: 6)

The resultant PCR fragments, digested with EcoR1 and Pst1, were ligated into the plant binary vector, pCAMBIA1300, and digested with EcoR1 and Pst1 to produce pCAMBIA1300-riceOsAnt1pro.

An AlaAT DNA fragment was amplified by PCR using pAG001 as a template. pAG001 is described in U.S. Pat. No. 6,084,153 where it is identified as pbtg26/AlaAT/nos. It contains the btg26 promoter linked to the barley AlaAT gene with a nopaline synthase terminator. The barley AlaAT/nos terminator sequences were amplified from pAG001 using the following primers:

Primer 6: PstIAlaAT sequence
AACTGCAGATGGCTGCCACCG    (SEQ ID NO: 7)

Primer 7: HindIII-NOS terminator sequence
CCCAAGCTTCCCGATCTAGTA    (SEQ ID NO: 8)

The resulting AlaAT/nos fragment was digested with Pst and HindIII and ligated into the pCAMBIA1300-riceOsAnt1pro digested with Pst1 and HindIII to produce a pCAMBIA1300-riceOsAnt1pro-AlaAT construct.

Transformation of Rice

Rice transformation methods are well known in the art (Sridevi et al., *Current Sci.* 88:128-132, 2005; Saharan et al., *African J. Biotech* 3(11):572-575, 2004; Khanna et al., *Aust. J. Plant Physiol.* 26:311-324, 1999; Zhang et al., *Molecular Biotechnology* 8(3):223-231, 1988; Rashid et al., *Plant Cell Rep.* 15:727-730, 1996; Aldemita and Hodges, *Planta* 199: 612-617, 1996; Hiei et al., *Plant J.* 6:271-282, 1997; Li et al., *Plant Cell Rpt* 12:250-255, 1993; Christou et al., *Biotechnology* 9:957-962, 1991). *Agrobacterium*-mediated transformation of rice was carried out as modified from U.S. Pat. No. 5,591,616 as described below.

pCAMBIA1305.1-riceOsAnt1pro-GUS and pCAMBIA1300-riceOsAnt1pro-AlaAT were transferred into *Agrobacterium* strain EHA105 (Hood et al., *Transgenic Res.* 2: 208-218, 1993) by electroporation (Sambrook et al., supra, 1989). *Agrobacterium* cells were plated on solid AB medium (Chilton et al., *Proc. Natl. Acad. Sci. USA* 71:3672-3676, 1974) containing 50 mg/l kanamycin and incubated at 28° C. for 3 days. The bacteria were then collected with a flat spatula and resuspended in liquid co-cultivation medium (R2-CL, Table 3) by gentle vortexing prior to transforming the rice tissues.

Mature seeds of rice (*Oryza sativa* L. cv. Nipponbare) were used in the transformation experiment. The seeds were dehusked and surface sterilized by dipping (1 min) in 70% (v/v) ethanol followed by soaking in 50% bleach plus 0.1% Tween-20 for 10 min and then rinsing five times in sterile distilled water. Following sterilization, seeds were cultured on callus induction medium (NB, Table 3) and incubated for three weeks in the dark at 28° C.

TABLE 3

Medium used for callus induction, inoculation, co-culture, resting phase, selection, regeneration and rooting

| Medium | Composition |
| --- | --- |
| NB[a] Callus induction medium | N6 major salt and iron source (Chu (1975) *Sci. Sin.* 5: 659-668) + B5 major salts and vitamins (Gamborg et al. (1968) |

TABLE 3-continued

Medium used for callus induction, inoculation, co-culture, resting phase, selection, regeneration and rooting

| Medium | Composition |
|---|---|
| (filter sterilize) | *Exp. Cell Res.* 50: 151-158) + 3AA (100 mg/l L-tryptophan + 500 mg/l L-proline + 500 mg/l L-glutamine) + 500 mg/l casein hydrolysate + 2.0 mg/l 2,4-D + 0.5 mg/l picloram + 30 g/l sucrose, pH 5.8, 0.3% gelrite |
| R2-CL Liquid co-culture medium (filter sterilize) | R2 major and minor salts, vitamins and iron source without sucrose (Ohira et al. (1973) *Plant and Cell Physiol.* 14: 1113-1121) + 0.25M glucose + 125 µM acetosyringone + 10 mM MES buffer, pH 5.2 + 50 mM potassium phosphate buffer, pH 5.2 + 400 mg/l L-cysteine + 2.0 mg/l 2,4-D + 0.5 mg/l picloram + 0.5 mg/l BAP, pH 5.2 |
| R2-CS Solid co-culture medium (filter sterilize) | R2 major and minor salts, vitamins and iron source without sucrose (Ohira et al. (1973) *Plant and Cell Physiol.* 14: 1113-1121) + 0.25M glucose + 125 µM acetosyringone + 10 mM MES buffer, pH 5.2 + 50 mM potassium phosphate buffer, pH 5.2 + 400 mg/l L-cysteine + .2.0 mg/l 2,4-D + 0.5 mg/l picloram + 0.5 mg/l BAP, pH 5.2 + 0.3% gelrite |
| R2-AS Resting phase (filter sterilize) | R2 major and minor salts, vitamins and iron source without sucrose + 0.25M sucrose + 0.5 mM acetosyringone + 10 mM MES buffer, pH 5.0 + 50 mM potassium phosphate buffer, pH 5.0 + 10 mM $CaCl_2$ + 400 mg/l L-cysteine + 2.0 mg/l 2,4-D + 0.5 mg/l picloram + 0.5 mg/l BAP + 250 mg/l cefotaxime + 250 mg/l amoxicillin, pH 5.0, 0.3% gelrite |
| R2S Selection medium (filter sterilize) | R2 major and minor salts, vitamins and iron source + 30 g/l sucrose + 2.0 mg/l 2,4-D + 0.5 mg/l picloram + 50 mg/l hygromycin + 250 mg/l cefotaxime + 100 mg/l amoxicillin, pH 5.8, 0.3% gelrite |
| NBS Selection medium-II (filter sterilize) | NB medium + 3AA + 2.0 mg/l 2,4-D + 0.5 mg/l Picloram + 50 mg/l hygromycin + 250 mg/l cefotaxime + 100 mg/l amoxicillin, pH 5.8, 0.3% gelrite |
| PRN Pre-regeneration medium (filter sterilize) | NB medium + 3AA + 5 mg/l ABA + 2 mg/l BAP + 0.5 mg/l NAA + 50 mg/l hygromycin + 100 mg/l cefotaxime + 50 mg/l amoxicillin, pH 5.8, 0.4% gelrite |
| RN Regeneration medium (filter sterilize) | NB medium + 3 mg/l BAP + 0.5 mg/l NAA + 50 mg/l hygromycin + 100 mg/l cefotaxime + 50 mg/l amoxicillin, pH 5.8, 0.4% gelrite |
| R Rooting medium (Autoclave/filter sterilize) | ½MS (Murashige and Skoog (1962) *Physiol. Plant* 15: 473-497) + 50 mg/l hygromycin[b] + 100 mg/l cefotaxime + 50 mg/l amoxicillin, pH 5.8, 0.3% gelrite |

[a]NB medium with 1.25 mg/l $CuSO_4$
[b]Optional

After three weeks, 3-5 mm long embryogenic nodular units released from the scutellum-derived callus at the explant/medium interface were immersed into 25 ml of liquid co-culture medium (R2-CL, Table 3) containing *Agrobacterium* cells at the density of 3-5×10$^9$ cells/ml ($OD_{600}$=1) in a 100 mm-diameter Petri dish for 10-15 minutes. Embryogenic units were then blotted dry on sterilized filter paper, transferred to a Petri dish containing solid co-culture medium (R2-CS, Table 3) and incubated for three days at 25° C. in the dark. Co-cultured embryogenic calli were then transferred to resting medium (R2-AS, Table 3) and incubated at 28° C. in the dark for a week.

After a week, uncontaminated embryogenic units were then individually transferred to selection medium (R2S, Table 3) containing hygromycin for selection of transformed tissue and incubated at 28° C. in the dark. Following 3 weeks of selection on R2S medium, the embryogenic units that turned dark brown with brownish protuberances arising throughout the callus surface were transferred to NBS selection medium (Table 3). After 5 weeks of co-culture, the protuberances developed into brownish globular structures that were gently teased apart from callus and incubated for 2 weeks in the resealed Petri dish. After 2 weeks, these globular structures converted into round shaped, compact and yellowish calli.

The putatively transgenic, hygromycin-resistant calli were gently picked out, transferred, cultured on pre-regeneration medium (PRN, Table 3) and then incubated for a further week. All of the resistant calli originating from a single co-cultured embryogenic nodular unit were grouped in a sector of the PRN dish. Creamy-white, lobed calli with a smooth and dry appearance were individually transferred to regeneration medium (RN, Table 3), incubated for 2 days in the dark, then maintained for three weeks under a 12/12-h (day/night) photoperiod with light provided at an intensity of 55 µmol/m per sec. Green shoots regenerating from a resistant callus were dissected and sub-cultured in test tube containing rooting medium (R, Table 3) for 1-2 weeks to promote vigorous roots and tillers before being transferred to pots in growth rooms. Transgenic plants were grown to maturity in 16-cm pots containing soil-less potting mixture (Metromix 220). Plants were maintained in growth rooms set to 28° C. and 14/10 hours day/night photoperiods. Fertilizer was applied twice a week starting two weeks after planting in pots. The fertilizer mix contained 225 g 20/20/20 fertilizer, 50 g of plant micronutrients, 6.1 g of $CuSO_4.5H_2O$, 140 g FeEDTA, 13.8 g $ZnSO_4.7H_2O$, 260 g $MgSO_4.7H_2O$, 3.7 g $H_3BO_3$ for a total of 712.4 g. Two grams of the fertilizer mix are dissolved in 8 liters of water and applied twice a week to 24 plants.

Analysis of Expression Directed by the OsAnt1 Promoter Sequence

Induction of expression directed by the OsAnt1 promoter sequence was examined using rice plants transformed with the OsAnt1pro-GUS construct. Plants were germinated and grown hydroponically in sterile conditions in Magenta jars. Two-week-old plants were stained for in vivo GUS activity by injecting into the root media 5 mls of 50 mM phosphate buffer (pH 7.5) containing 0.2 mM X-gluc (5-bromo-4-chloro-3-indolyl-beta-glucuronic acid) and incubating the plants in this media for 1-24 hours. Root tissue was then viewed under a dissection microscope and photographs were taken, which are shown in FIG. 7.

Dark stained areas in FIG. 7 indicate expression of the GUS reporter gene. There is no expression of the GUS reporter gene driven by the OsAnt1 promoter in the root tip (specifically the dividing cells); however, expression begins very quickly in the cell expansion zone, just behind the root tip. The OsAnt1 promoter sequence directed expression of the GUS reporter gene in the root hairs as well. Further from the root tip in more mature roots, expression is lost from the main root, but lateral roots stain very heavily, indicating that OsAnt1 directs expression in these lateral roots very strongly.

Analysis of Transformed Rice Plants Containing the AlaAt Construct

Fifty-eight OsAnt1/AlaAT/NOS transgenic plants were generated and measurements for flowering, tiller number, seed weights and biomass at maturity were recorded for the $T_0$ generation plants.

Figure 8:
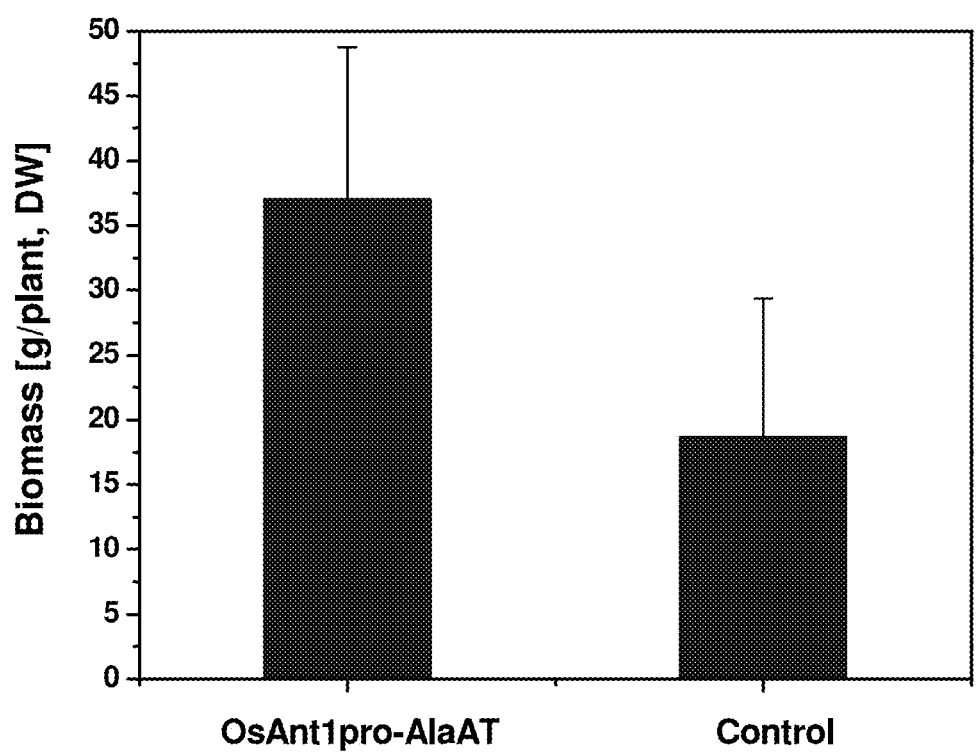
FIG. 8 shows the average dry weight biomass (grams) of *Oryza sativa* plants transformed with the genetic construct OsAnt1pro-AlaAT as shown in FIG. 6 compared to the average dry weight biomass (grams) of control, wild-type *Oryza sativa* plants grown under the same growth conditions as given in Example 1.

The dry weight biomass of OsAnt1/AlaAT plants and control plants was measured at maturity, and the data is presented in FIG. 8. The average biomass of the transgenic OsAnt1/AlaAT plants was higher than the average biomass of control plants.

Figure 9:
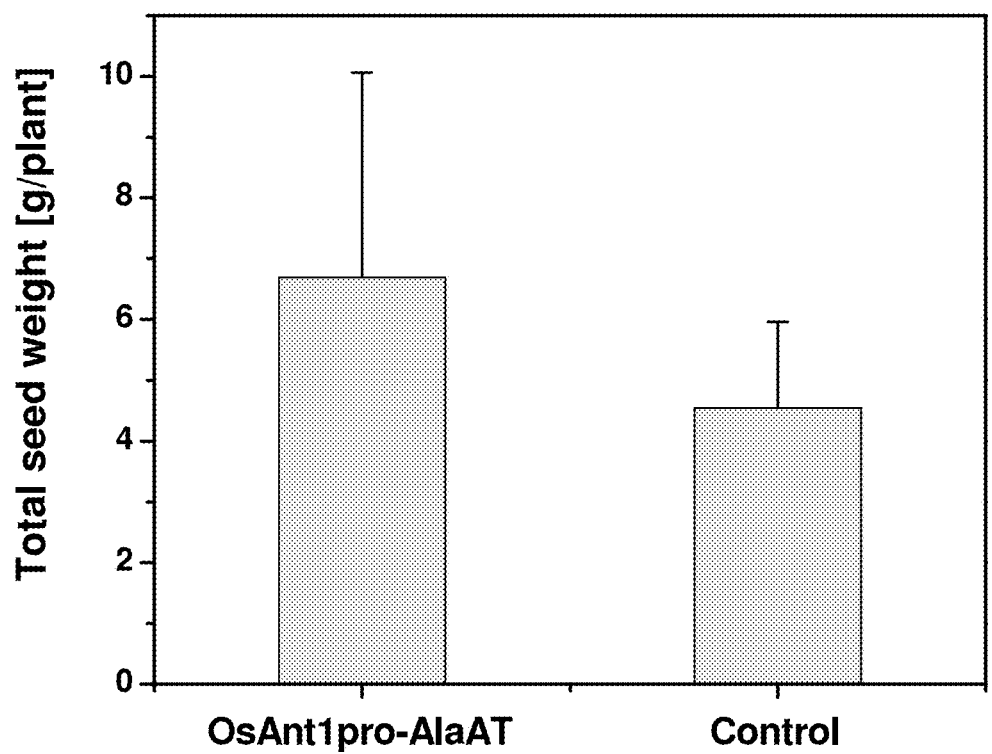
FIG. 9 shows the average total seed weight (grams) of seeds collected from Oryza sativa plants transformed with the genetic construct OsAnt1pro-AlaAT as shown in FIG. 6 compared to the average total seed weight (grams) of seeds collected from control, wild-type Oryza sativa plants grown under the same growth conditions as given in Example 1.

Seeds were collected from OsAnt1/AlaAT plants and control plants at maturity and the total weight of the seeds was measured. The results are shown in FIG. 9, which shows that the total seed weight of seeds collected from OsAnt1/AlaAT plants was higher than that of the seed weight from control plants.

Figure 10:
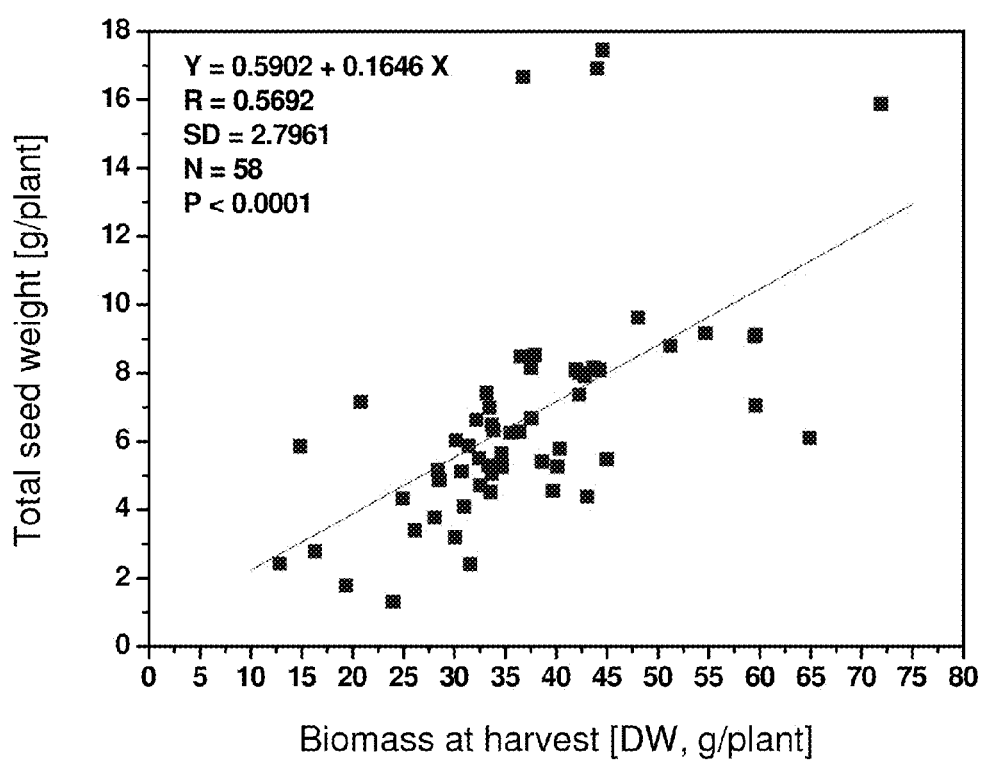
FIG. 10 shows the relationship between dry weight biomass (grams) and total seed weight (grams) for each transgenic plant.

FIG. 10 shows the relationship between dry weight biomass and total seed weight for each transgenic plant. A substantially linear correlation is shown, which indicates that an increase in biomass results in a corresponding increase in total seed weight in OsAnt1/AlaAT plants.

These results indicate that OsAnt1/AlaAT transgenic plants are capable of optimizing the utilization of available nutrients thereby resulting in an increase in plant biomass, seed yield or a combination thereof.

Example 2

Demonstration of NUE in Maize using OsAnt1/Barley AlaAT

The OsAnt1-pro-AlaAT construct can be incorporated into suitable plant binary vectors for use in *Agrobacterium*-mediated transformation of maize. Many methods for transformation of immature embryos of maize using a variety of selectable markers are known in the art (Ishida et al., *Nature Biotech.* 14:745-750, 1996; Lupotto, *Maydica* 44:211-218, 1999; Zhao et al.; *Molec. Breeding* 8:323-333, 2001; Frame et al., *Plant Physiol.* 129:13-22, 2002 and Miller et al., *Transgenic Res.* 11:381-396, 2002, U.S. Pat. No. 5,591,616. Contract production of transgenic maize plants is also available through facilities such as the Plant Transformation Facility, Iowa State University, Ames, Iowa.

Alternatively, the OsAnt1pro-AlaAT sequence can be used similarly in biolistic transformation methods for maize (Wright et al., *Plant Cell Reports* 20(5):429-436, 2001; Brettschneider et al., *Theoret. Appl. Genet.* 94:737-748, 1997; Gordon-Kamm et al., *Plant Cell* 2(7):603-618, 1990; Fromm et al., *Biotechnology* (NY). 8(9):833-9. 1990).

Maize plants can be tested for NUE by measurement of biomass and seed yield during growth under various nitrogen fertilizer regimes including limiting nitrogen. Plant biomass can be fresh weight or dry weight, total plant weight, leaf weight or root weight. Suboptimal nitrogen conditions are those conditions in which nitrogen concentrations limit growth. Under such conditions, addition of added nitrogen such as fertilizer will increase growth. For each of these tests, biomass and seed yield can be evaluated in growth chamber, greenhouse or field tests.

Example 3

Demonstration of NUE in Wheat using OsAnt1/Barley AlaAT

Similar to maize, the OsAnt1-pro-AlaAT construct can be used for particle-gun bombardment transformation methods of wheat (Pastori et al., *J. Exp. Bot.* 52(357):857-863, 2001; Becker et al., *Plant J.* 5:299-307, 1994) or incorporated into suitable plant binary vectors for use in *Agrobacterium*-mediated transformation of wheat (Cheng et al., *Plant Physiol.* 115:971-980, 1997; U.S. Patent Application US2003/0024014A1) Other methods for wheat transformation are established in the art.

Wheat plants can be tested for NUE by measurement of biomass and seed yield during growth under various nitrogen fertilizer regimes including limiting nitrogen. Plant biomass can be fresh weight or dry weight, total plant weight, leaf weight or root weight. Suboptimal nitrogen conditions are those conditions in which nitrogen concentrations limit growth. Under such conditions, addition of added nitrogen such as fertilizer will increase growth. For each of these tests, biomass and seed yield can be evaluated in growth chamber, greenhouse or field tests.

Example 4

Demonstration of NUE in Sorghum using OsAnt1/Barley AlaAT

*Agrobacterium*-mediated sorghum transformation of immature embryos with a binary vector containing any of the OsAnt promoter/AlaAT constructs can be achieved according to methods established in the art (Zhao et al., *Plant Mol. Biol.* 44(6):789-98, 2000; Gao et al., *Genome* 48(2):321-33, 2005; Zhao, Z. Y., *Methods Mol, Biol.* 343:233-44, 2006; Howe et al., *Plant Cell Rep.* 25(8):784-91, 2006).

*Sorghum* plants can be tested for NUE by measurement of biomass and seed yield during growth under various nitrogen fertilizer regimes including limiting nitrogen. Plant biomass can be fresh weight or dry weight, total plant weight, leaf weight or root weight. Suboptimal nitrogen conditions are those conditions in which nitrogen concentrations limit growth. Under such conditions, addition of added nitrogen such as fertilizer will increase growth. For each of these tests, biomass and seed yield can be evaluated in growth chamber, greenhouse or field tests.

Example 5

Identification of Alternate (Antiquitin) Promoter Sequences for Use in NUE Constructs Other antiquitin promoter sequences useful in monocots can be identified in sequence databases. As described for isolation of the rice promoter in Example 1, the nucleotide sequence (bp 366-3175) of the btg26 gene (Stroeher et al., *Plant Mol. Biol.* 27:541-551, 1995; accession number S77096) is used to search the nucleotide database at NCBI using the blastn search tool. In addition to the rice sequence identified, other monocot antiquitin sequences are identified in the nr database including sorghum (accession number U87982), maize (accession numbers AY103614 and BT017791), cocoa (*Theobroma cacao*; accession number DQ448866; and *Curculigo latifolia*, accession number X64110). ESTs for wheat, sugarcane and switchgrass can also be identified in databases using the identified rice antiquitin nucleotide or amino acid sequences using various search algorithms.

Similar to the identification of the OsAnt1 promoter, a sorghum promoter sequence was identified by using the rice nucleotide sequence of the antiquitin clone (accession number AF323586) in a BLAST search of the sorghum sequences in the NCBI Genome Sequence Survey (gss) Database. Clone CW033386 was identified as containing 443 nucleotides of sequence upstream of the ATG start codon of a sorghum antiquitin gene (SEQ ID NO:9, FIG. 11). This sequence can be used as a promoter sequence alone or methods to clone and sequence larger genomic fragments can be used to identify sequences further upstream. These fragments can be parts of BAC sequences or from further genome sequencing efforts in sorghum or the like. One skilled in the art could also walk-up the genome using methods such as inverse PCR and genome walking kits.

An upstream sequence of the maize antiquitin gene was identified in a BLAST search using the sequence of the rice antiquitin clone against the *Zea mays* sequences in the NCBI Genome Survey Sequences Database. Accession BH215004 was identified as containing a 204-bp sequence upstream of a maize antiquitin gene (SEQ ID NO:10, FIG. 12). This sequence can be used as a promoter sequence alone or methods to clone and sequence larger genomic fragments can be used to identify sequences up to 1.5 kb upstream of this particular antiquitin gene. Sequences including the longer promoters could be used to design promoter/AlaAT gene constructs as described below.

Example 6

Construction of Alternate Expression Cassettes for NUE Constructs

Promoter cassettes for expression of various genes are constructed by combining the promoter of interest with a nos terminator with convenient restriction sites in between the promoter and terminator for gene cloning. Other restriction sites flank the promoter and terminator to facilitate movement of the cassette to a binary vector for plant transformation.

A base vector containing the nos terminator is constructed by PCR amplifying the nos region contained in the binary vectors described in U.S. Pat. No. 6,084,153 with the primers NOSupper2: 5'-CCTAGGCCATGGTTCAAACATTTG-GCAATAAAGTTT-3' (SEQ ID NO: 11) and NOSlower: 5'-TTAATTAACGATCTAGTAACATAGATGACA-3' (SEQ ID NO: 12). NOSupper2 supplies AvrII and NcoI restriction sites at the 5'-end of the nos terminator and NOSlower supplies a PacI site at the 3' end of the amplified fragment. PCR was performed using the BD Advantage™ 2 PCR kit following manufacturer's instructions. The resulting 263 bp fragment is cloned into pCR®2.1-TOPO® vector using a TOPO TA Cloning® Kit (Invitrogen) and One Shot® *E. coli* cells following manufacturer's instructions. This plasmid is Nos/PCR2.1.

The Nco1 site in the kanamycin resistance gene in the Nos/pCR2.1 backbone is removed using the QuikChange® XL Site-Directed Mutagenesis Kit (Stratagene) following manufacturer's instructions. Primers that may be used to introduce a silent nucleotide change are NcoIpCR2.1 Lower 5'-GCAGGCATCGCCATGAGTCACGACGAGATC-3' (SEQ ID NO: 13) and NcoIpCR2.1 Upper 5'-GATCTCGTCGTGACTCATGGCGATGCCTGC-3' (SEQ ID NO: 14). Deletion of the Nco1 site may be verified by restriction analysis and growth of the *E. coli* on kanamycin. This resulting plasmid is Nos/pCR2.1mut.

An alternative expression cassette for expressing genes from the OsAnt1 promoter is made in the following manner. The OsAnt1 promoter is cloned from rice var. Nipponbare genomic DNA (made by manufacturer's recommendation, Sigma Extract-n-AMP™) using PCR. Primers for a slightly longer version of the OsAnt1 promoter than that shown in SEQ ID NO: 1 are:

```
Forward primer
                                        (SEQ ID NO: 15)
5'-
ATTAAACCTAGGTTAATTAAGTTTAAACGACCTATAAAGTCAAATGCAAA
T- 3'
and reverse primer
                                        (SEQ ID NO: 16)
5-
TTTAATTCATGAGACGTCTTTGCGATCGCGCAGAAGAGAGAGAGAGAG
GTAG- 3'.
```

The forward primer incorporates Avr II, PacI and PmeI restriction sites and the reverse primer incorporates BspHI, Aat II and AsiSI and restriction sites to facilitate further cloning steps. The resulting 1.1 kb fragment (corresponding to nucleotides 101336-100216 of AP005570) is cloned into pCR®2.1-TOPO® vector using a TOPO TA Cloning® Kit (Invitrogen) and One Shot *E. coli* cells following manufacturer's instructions. The resulting plasmid is digested with restriction enzymes Avr II and BspH1 and is cloned into Nos/pCR2.1mut that has been digested with Avr II and Nco1. The resulting construct has an OsAnt1 promoter and a nos3'-region with unique AsiSI and AatII sites between them for cloning genes of interest. The expression cassette is flanked by Avr II, Pac I, and Pme I restriction sites on the 5'-end and a PacI restriction site on the 3'-end to facilitate movement into a plant binary expression vector.

An expression cassette utilizing a sorghum Ant promoter is designed in a similar manner. Forward primer 5'-ATTAAAC-CTAGGTTAATTAAGTTTAAACGATTCGAC AATATT-TATCAAAT-3' (SEQ ID NO: 17) and reverse primer 5-TT-TAATTCATGAGACGT CTTTGCGATCGCGGCGCCGGCGGC GTTGGCAGGT-3' (SEQ ID NO: 18) can be used to amplify a 443-bp Ant promoter (SEQ ID NO:9) from sorghum genomic DNA as described above for the OsAnt1 promoter and rice DNA. The cloned promoter fragment is flanked by AvrII, Pac 1 and Pme 1 restriction sites on the 5'-end and BspHI, Aat II and Asi SI sites on the 3'-end. The promoter fragment is digested with restriction enzymes Avr II and BspH1 and is cloned into Nos/pCR2.1mut that has been digested with Avr II and Nco1.

The resulting construct has a sorghum Ant promoter and a nos3'-region with unique AsiSI and Aat II sites between them for cloning genes of interest. The expression cassette is flanked by Avr II, Pac I, and Pme I restriction sites on the 5'-end and a PacI restriction site on the 3'-end to facilitate movement into a plant binary expression vector.

An expression cassette utilizing a maize Ant promoter (see Example 5) is also designed in a similar manner to that described for the rice and sorghum. Promoter regions from other antiquitin genes can also be used as they are identified from genome sequencing projects and other technologies.

Example 7

Identification and Cloning of Alternate Alanine Aminotransferase (AlaAt) Genes for Use in NUE Constructs Aminotransferases are enzymes which catalyze the reversible transfer of amino groups from amino acids to oxo acids. They can be divided into four subgroups based on mutual structural relatedness (Mehta et al., *Eur. J. Biochem.* 214(2): 549-561, 1993). AlaAT enzymes catalyze the reversible interconversion of alanine and 2-oxoglutarate to pyruvate and glutamate and belong to subgroup 1. In addition to the barley alanine aminotransferase, other alanine aminotransferases are useful for conferring NUE in monocots.

To identify homologous AlaAT genes, the barley AlaAT protein sequence (NCBI accession number CAA81231) was used as a query to search the NCBI protein sequence database using the BLAST algorithm. Genes with a high degree of sequence homology to barley AlaAT were found in all major classes of eukaryotes. Related sequences were also found in bacteria. A tBlastn search of the NCBI EST database revealed that AlaAT homologs are widespread in plants, but because most of these sequences were not full length they were not analyzed further. As additional genomic sequences for monocots become available, additional homologs may be identified using these methods.

Full length sequences identified in the BLAST search were further analyzed using the AlignX program (part of Vector NTI program suite, Invitrogen). A lineup of representative sequences and the corresponding homology table using sequences from a range of organisms is shown in FIG. 2 and Table 1. The most homologous sequences were plant sequences. A lineup of representative plant sequences and the corresponding homology table is shown in FIG. 3 and Table 2. Note that some of sequences used for these alignments have been truncated so that they contain less than the complete sequence of the cited AlaAT. The alignment was performed using the methionine (M) of the barley AlaAT sequence as the reference first residue.

mRNA Isolation and cDNA Synthesis

Tissue for RNA isolation was prepared from maize (A188) and rice (Nipponbare) in the following manner. Seeds were germinated in H₂O⁻ on germination paper at 24° C. in a sealed bag (maize, rice). After 7 days root tissue was collected and stored in RNAlater® (Ambion) for RNA isolation. Seedlings of pepper (*Capsicum annuum*, Pepper Hot Asia, Santaka, Botanical Interests Broomfield, Colo.) were sterilized and germinated in half strength MS and whole seedlings were used. Leaves from soil-grown *Arabidopsis* plants (Columbia 0) were used.

RNA was prepared from the plant tissues using the RNAqueous™-4PCR kit (Ambion). cDNA was synthesized from purified RNA using the Superscript III Platinum® 2-step q-RT-PCR kit (Invitrogen) as per the manufacturer's instructions.

PCR Amplification of AlaAT

AlaAT genes may be amplified by PCR from cDNA from many sources including maize (*Zea mays*), rice (*Oryza sativa*), *Arabidopsis thaliana*, or pepper (*Capsicum annuum*). The template for barley (*Hordeum vulgare* L. cv Himalaya) AlaAT is plasmid pAG001 (obtained from Allen Good, University of Alberta) which contains the barley AlaAT coding sequences as described in Muench and Good, 1994, GenBank accession CAA81231. PCR primers contain an AsiS I restriction site on the 5'-end and an Aat II restriction site at the 3'-end to facilitate cloning into expression cassettes. The primer pairs for the individual genes are listed below:

```
Barley Fw:
                                     (SEQ ID NO: 19)
5'-ATTAAAGCGATCGCACCATGGCTGCCACCGTCGCCGTGGA-3'

Barley Rv:
                                     (SEQ ID NO: 20)
5'-TAGTGAGACGTCTTAGTCACGATACTCTGACA-3'

Maize Fw:
                                     (SEQ ID NO: 21)
5'-ATTAAAGCGATCGCACCatggccgccagcgtcaccgtgga-3'

Maize Rv:
                                     (SEQ ID NO: 22)
5-TAGTGAGACGTCTTAGTCGCGGTACTCGGCCAA-3'

Rice Fw:
                                     (SEQ ID NO: 23)
5'-ATTAAAGCGATCGCACCATGGCTGCTCCCAGCGTCGCCGT-3'

Rice Rv:
                                     (SEQ ID NO: 24)
5'-TAGTGAGACGTCTCAGTCGCGGTACGCTGCCATGAA-3'

Arabidopsis At1g17290 Fw:
                                     (SEQ ID NO: 25)
5'-
ATTAAAGCGATCGCACCATGCGGAGATTCGTGATTGGCCAA-3'

Arabidopsis At1g17290 Rv:
                                     (SEQ ID NO: 26)
5'-
TAGTGAGACGTCTTAGTCGCGGAACTCGTCCATGAA-3'

Pepper Fw:
                                     (SEQ ID NO: 27)
5'-ATTAAAGCGATCGCACCATGGATTCCATCACTATTGAT-3'

Pepper Rv:
                                     (SEQ ID NO: 28)
5'-TAGTGAGACGTCTTAGCCGCAGAATTCATCCAT-3'
```

AlaAT genes may be amplified using the BD Advantage™ 2 PCR kit following manufacturer's instructions (Clontech, Mountain View, Calif.). The resulting PCR products may be purified using QIAquick™ Purification Kit (Qiagen®, Hilden, Germany) and digested with AsiSI and Aat II restriction enzymes. The products may be ligated to the OsAnt1, sorghum Ant or maize Ant expression cassettes described above that have been digested with AsiSI and Aat II restriction enzymes.

The AlaAT gene in each of the expression constructs is sequence verified for PCR fidelity and integrity of the ATG start codon.

Example 8

Binary Vector Construction and Plant Transformation

The Ant promoter/AlaAT gene/nos 3' expression cassettes are cloned into a binary vector for plant transformation by digestion with Pme1 and Pac1 and ligation with pARC110 digested with the same enzymes. pARC110 is an *Agrobacterium binary* vector originally based on pZP100 (Hajdukiewicz et al., *Plant Mol. Biol.* 25, 989-994, 1994). pARC110 utilizes a Basta selectable marker driven by a CaMV 35S promoter and a nos terminator. The selectable marker is located near the left border, and the unique restriction sites Xba I, Avr II, Pac 1, and Pst I have been engineered close to the RB for gene cloning. The chloramphenicol bacterial selectable marker in the backbone of pZP100 was also replaced with the kanamycin resistance gene (nptIII) from the pCAMBIA 1304 vector (found on the internet at the cambia.org website.

The promoter/AlaAT/nos 3' gene binary vectors can be introduced into *Agrobacterium tumefaciens* strains for *Agrobacterium*-mediated transformation of monocot crop plants or vector DNA is used for particle gun bombardment methods of plant transformation.

Example 9

Use of Alternate Antiquitin/AlaAt Constructs in Rice Transformation Using Selection on Bialophos

*Agrobacterium*-mediated rice transformation with the OsAnt1/AlaAT construct, or any alternate Ant/AlaAT construct, is achieved using a transformation method based on the method described in U.S. Pat. No. 7,060,876 and European Patent No. 672752B1. A detailed description follows.

Plasmids were transferred into *Agrobacterium* strain EHA105 (Hood et al., *Transgenic Res.* 2: 208-218, 1993) by electroporation (Sambrook et al. in Molecular Cloning, A Laboratory Manual Cold Spring Harbor, N.Y.: Cold Spring Harbor Laboratory Press, 1989). *Agrobacterium* cells were plated on solid AB medium (Chilton et al., 1974) containing 50 mg/l kanamycin and incubated at 28° C. for 3 days. The bacteria were then collected with a flat spatula and resuspended in liquid co-cultivation medium (R2-CL, Table 4) by gentle vortexing prior to transforming the rice tissues.

Mature seeds of rice (*Oryza sativa* L. cv. Nipponbare) were used in the transformation experiment. The seeds were dehusked and surface sterilized by dipping (1 min) in 70% (v/v) ethanol followed by soaking in 50% bleach plus 0.1% Tween-20 for 10 min and then rinsing five times in sterile distilled water. Following sterilization, seeds were cultured on callus induction medium (N6C, Table 4) and incubated for three weeks in the dark at 26° C.

TABLE 4

Medium used for callus induction, inoculation, co-culture, resting phase, selection, regeneration and rooting

| Medium | Composition |
|---|---|
| N6C<br>Callus induction medium<br>(autoclave) | N6 major salt, iron source, minor salts and vitamins (Chu (1975) *Sci. Sin.* 5: 659-668) + 3AA (100 mg/l myo-inositol + 500 mg/l L-proline + 500 mg/l L-glutamine) + 300 mg/l casein hydrolysate + 2.0 mg/l 2,4-D + 30 g/l sucrose, pH 5.8, 0.35% gellan gum |
| R2-CL<br>Liquid co-culture medium<br>(filter sterilize) | R2 major and minor salts, vitamins and iron source without sucrose (Ohira et al. (1973) *Plant and Cell Physiol.* 14: 1113-1121) + 0.25M glucose + 125 μM acetosyringone + 2.0 mg/l 2,4-D, pH 5.2 |
| R2-CS<br>Solid co-culture medium<br>(filter sterilize) | R2-CL + 0.35% gellan gum |
| N6S<br>Selection medium<br>(filter sterilize) | N6C medium + 200 mg/l Timentin + 7.5 mg/l bialaphos, pH 5.8 |
| RN<br>Regeneration medium | MS medium (Murashige & Skoog (1962) *Physiol Plant* 15: 473-497) + 2 mg/l kinetin + 0.02 mg/l NAA + 200 mg/l Timentin + 7.5 mg/l bialaphos, pH 5.8, 0.35% gellan gum. |
| R<br>Rooting medium | ½ strength MS medium (Murashige & Skoog (1962) *Physiol. Plant* 15: 473-497) + 100 mg/l Timentin, pH 5.8, 0.35% gellan gum |

After three weeks, 3-5 mm long embryogenic nodular units released from the scutellum-derived callus at the explant/medium interface were immersed into 25 ml of liquid co-culture medium (R2-CL, Table 4) containing *Agrobacterium* cells at the density of $10^9$ cells/ml ($OD_{600}$=0.3) in a 100 mm-diameter Petri dish for 10-15 minutes. Embryogenic units were then blotted dry on sterilized filter paper, transferred to a Petri dish containing solid co-culture medium (R2-CS, Table 4) and incubated for three days at 25° C. in the dark. Co-cultivated embryogenic calli were then transferred to N6 liquid medium containing 400 mg/l Timentin for disinfection and placed for 4 hours on an orbital shaker (100 rpm) at 26° C. in the dark. After dry blotting on sterile filter paper, calli were placed on N6 selection medium (N6S, Table 4) and kept at 26° C. in dark.

After 4 weeks of culture, uncontaminated embryogenic units had developed into large yellowish globular structures that were transferred onto fresh N6S medium and cultured for another 4-5 weeks at 26° C. in dark.

The globular structures had proliferated many round-shaped, compact and yellowish calli. These putatively transgenic, bialaphos-resistant calli were gently picked out, transferred and cultured on regeneration medium (RN, Table 4), incubated for 1 week in the dark, then maintained for 4-5 weeks under a 14/10 hours day/night photoperiod with light provided at an intensity of 70 μmol/m per sec. Green shoots regenerating from a resistant callus were dissected and subcultured in culture vessels containing rooting medium (R, Table 4) for 2 weeks to promote vigorous roots and tillers before being transferred to 2-inch pots filled with sterile Sunshine Mix #3. The transgenic plantlets were acclimated by maintaining them in growth rooms set to 26° C., 14/10 hours day/night photoperiod and high humidity. Fertilizer was applied three times a week starting two weeks after planting in pots. The fertilizer mix is Simmons Solution (San Joaquin Sulphur Co., Lodi, Calif.) with addition of calcium nitrate. Sixteen g of Simmons and 60 g of calcium nitrate are mixed for 40 gallons of fertilizer.

Nitrogen efficient monocot plants including but not limited to maize, sorghum, barley, wheat, rye and grass can be developed using the methods outlined in the above examples.

The invention has been described with regard to one or more embodiments. However, it will be apparent to persons skilled in the art that a number of variations and modifications can be made without departing from the scope of the invention as defined in the claims. The following statements of the invention are intended to characterize possible elements of the invention according to the foregoing description given in the specification. Because this application is a provisional application, these statements may be changed upon preparation and filing of the complete application. Such changes are not intended to affect the scope of equivalents according to the claims issuing from the complete application, if such changes occur.

All citations are hereby incorporated by reference.

We claim:

1. A transgenic monocot plant comprising a rice antiquitin promoter operably linked with a nucleic acid encoding an alanine aminotransferase, wherein the rice antiquitin promoter comprises SEQ ID NO:1 or a sequence having 99.9% sequence identity to SEQ ID NO:1.

2. The transgenic monocot plant of claim 1, wherein expression of said nucleic acid in said monocot plant causes an increase in plant dry weight biomass as compared to the plant dry weight biomass of a comparable monocot plant not expressing said nucleic acid when the plant expressing the nucleic acid and the plant not expressing the nucleic acid are grown under conditions that are limiting nitrogen conditions for the plant not expressing the nucleic acid.

3. The transgenic monocot plant of claim 2, wherein said alanine aminotransferase is selected from the group consisting of barley, rice, and maize, alanine amino transferases.

4. The transgenic monocot plant of claim 2, wherein the transgenic monocot plant is selected from the group consisting of barley, rice, sugar cane, maize, sorghum, rye, wheat and turfgrass.

5. The transgenic monocot plant of claim 2, wherein the transgenic monocot plant is rice.

6. The transgenic monocot plant of claim 2, wherein the rice antiquitin promoter comprises SEQ ID NO: 1.

7. The transgenic monocot plant of claim 2, wherein the rice antiquitin promoter comprises a sequence having 99.9% sequence identity to SEQ ID NO:1.

8. The transgenic monocot plant of claim 1, wherein expression of said nucleic acid in said monocot plant causes an increase in seed weight as compared to the seed weight of a comparable monocot plant not expressing said nucleic acid when the plant expressing the nucleic acid and the plant not expressing the nucleic acid are grown under conditions that are limiting nitrogen conditions for the plant not expressing the nucleic acid.

9. The transgenic monocot plant of claim 8, wherein said alanine aminotransferase is selected from the group consisting of barley, rice, and maize, alanine amino transferases.

10. The transgenic monocot plant of claim 8, wherein the transgenic monocot plant is selected from the group consisting of barley, rice, sugar cane, maize, sorghum, rye, wheat and turfgrass.

11. The transgenic monocot plant of claim 8, wherein the transgenic monocot plant is rice.

12. The transgenic monocot plant of claim 8, wherein the rice antiquitin promoter comprises SEQ ID NO: 1.

13. The transgenic monocot plant of claim 8, wherein the rice antiquitin promoter comprises a sequence having 99.9% sequence identity to SEQ ID NO:1.

14. Seed from the transgenic monocot plant of claim 1, wherein the seed comprises the rice antiquitin promoter operably linked with the nucleic acid encoding the alanine aminotransferase.

15. The transgenic monocot plant of claim 2, wherein said alanine aminotransferase is selected from the group consisting of *Hordeum vulgare, Panicum miliaceum, Oryza sativa, Zea mays, Arabidopsis thaliana*, and *Capsicum* sp. alanine amino transferases.

16. The transgenic monocot plant of claim 8, wherein said alanine aminotransferase is selected from the group consisting of *Hordeum vulgare, Panicum miliaceum, Oryza sativa, Zea mays, Arabidopsis thaliana*, and *Capsicum* sp. alanine amino transferases.

\* \* \* \* \*

SEQUENCE LISTING

```
<160> NUMBER OF SEQ ID NOS: 45

<210> SEQ ID NO 1
<211> LENGTH: 973
<212> TYPE: DNA
<213> ORGANISM: Oryza sativa

<400> SEQUENCE: 1
aggaagtgat ttttagcgta gctgtgtttg tagcgtaatt gcgtaaagtc ctttcaattt    60
tgctatatct cactcgaaag attttttctt atctctcact cgattttctc actcaaattt   120
acagtgtatt ttcttgtaag ttacagtgta atttatgaaa cttacactgt aacttttgta   180
agttacactg taattttga atcttcacat gtaaatttta aattttgtat tggatttggt    240 cttttcttg aggatatggt aatttaatgt tcattatggt gtttcttaat tgcttttgc     300 tttttattat atctatcgga ttttaataca aagattaaaa atctgtgtga tacgattata   360
aaaatctttc gaaagatgta taggtactcc caagcccttt taagaaagtt tttcaagaca   420 aaagttttg gatgaaaggt agttataggg aaaaaggaat gtgcgtttat gtttatttgc    480
attgcttatt ggcaaccaaa aactaatcta taagtaaatc ttttatatac gtgcgcttaa   540
taattcaaaa gcaaattcat gtaaaataaa atgcgatgaa gaaactttaa aaagttatca   600
aatttagatt ttattaaatt ttagtttaca agagcgctac gatgaaggct ttaaaaagat   660
gggaaaataa aacctttgac ctttctggac ttcaccaaac agctcacgct ttcggcttcg   720
tgccgtctcg tcccgtgcta ctgctacccc ctcctgaccc cacccgccac tccacgctcc   780
cttctcctcc ccttcccgtg acacacagtc cccactccac cgcctccgta taagtatccc   840
ttccttaccg ccggccagcc acagccaccg cctcccccac cccacccga tcccctcccc    900 gccgtacggg cgcagaagga acccgtcttc tagaaggagg aggagggcta cctctctctc   960
tctctcttct gcc                                                      973

<210> SEQ ID NO 2
<211> LENGTH: 24
<212> TYPE: DNA
<213> ORGANISM: Artificial Sequence
<220> FEATURE:
<223> OTHER INFORMATION: Synthesized Construct

<400> SEQUENCE: 2
aggaagtgat ttttagcgta gctg                                          24

<210> SEQ ID NO 3
<211> LENGTH: 25
```

```
<212> TYPE: DNA
<213> ORGANISM: Artificial Sequence
<220> FEATURE:
<223> OTHER INFORMATION: Synthesized Construct

<400> SEQUENCE: 3
atggcagaag agagagagag agagg                                          25

<210> SEQ ID NO 4
<211> LENGTH: 21
<212> TYPE: DNA
<213> ORGANISM: Artificial Sequence
<220> FEATURE:
<223> OTHER INFORMATION: Synthesized Construct

<400> SEQUENCE: 4
ggaattcagg aagtgatttt t                                              21

<210> SEQ ID NO 5
<211> LENGTH: 21
<212> TYPE: DNA
<213> ORGANISM: Artificial Sequence
<220> FEATURE:
<223> OTHER INFORMATION: Synthesized Construct

<400> SEQUENCE: 5
catgccatgg atggcagaag a                                              21

<210> SEQ ID NO 6
<211> LENGTH: 19
<212> TYPE: DNA
<213> ORGANISM: Artificial Sequence
<220> FEATURE:
<223> OTHER INFORMATION: Synthesized Construct

<400> SEQUENCE: 6
aactgcagat ggcagaaga                                                 19

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
aactgcagat ggctgccacc g                                              21

<210> SEQ ID NO 8
<211> LENGTH: 21
<212> TYPE: DNA
<213> ORGANISM: Artificial Sequence
<220> FEATURE:
<223> OTHER INFORMATION: Synthesized Construct

<400> SEQUENCE: 8
cccaagcttc ccgatctagt a                                              21

<210> SEQ ID NO 9
<211> LENGTH: 443
<212> TYPE: DNA
<213> ORGANISM: Sorghum bicolor

<400> SEQUENCE: 9
gattcgacaa tatttatcaa ataaaaacga aaatactaca ttagtgaaat ctgaattttt    60
tttcgaacta acaaggcccc aagacacaga acgtgcacac gcaaagctgg cgttcaatga  120
```

```
tacgtataat gataaaatta tatttgttgt atttttttaaa cctacaaaca cgccacgccc    180
atgcccacgc ccacgctttc gtctcgtctc gtcccgtgaa caaacaacaa cagtacagca    240
gcagcaccca ccgcaccacc attcctccgc gcccagcctc cttcgtctcc ttccctcccg    300
gagcagttca cagtccccac tccacctcct cctacaaata cacctcacta cttcaccacg    360
cctctgctcc cctgccttcc gcttccctcc ctatccccccc cacccccccg catcgtacgg    420
aacctgccaa cgccgccggc gcc                                             443

<210> SEQ ID NO 10
<211> LENGTH: 204
<212> TYPE: DNA
<213> ORGANISM: Zea mays

<400> SEQUENCE: 10
tctgtcccgt gaacaaacaa acggcaaggc cgtccaaccg taccactcct ccgcgccggg    60
cccgggctcc atcgccttcc cggagcagtt cacagtcccc actccacctc cttctacaaa    120
tacacctcag tctcagcccc ccaccacatc cgctccccgc cttccgcttc cctaccccccc  180 gcatcaccta ccaacgccgg cgcc                                            204

<210> SEQ ID NO 11
<211> LENGTH: 36
<212> TYPE: DNA
<213> ORGANISM: Artificial Sequence
<220> FEATURE:
<223> OTHER INFORMATION: Synthesized Construct

<400> SEQUENCE: 11
cctaggccat ggttcaaaca tttggcaata aagttt                               36

<210> SEQ ID NO 12
<211> LENGTH: 30
<212> TYPE: DNA
<213> ORGANISM: Artificial Sequence
<220> FEATURE:
<223> OTHER INFORMATION: Synthesized Construct

<400> SEQUENCE: 12
ttaattaacg atctagtaac atagatgaca                                      30

<210> SEQ ID NO 13
<211> LENGTH: 30
<212> TYPE: DNA
<213> ORGANISM: Artificial Sequence
<220> FEATURE:
<223> OTHER INFORMATION: Synthesized Construct

<400> SEQUENCE: 13
gcaggcatcg ccatgagtca cgacgagatc                                      30

<210> SEQ ID NO 14
<211> LENGTH: 30
<212> TYPE: DNA
<213> ORGANISM: Artificial Sequence
<220> FEATURE:
<223> OTHER INFORMATION: Synthesized Construct

<400> SEQUENCE: 14
gatctcgtcg tgactcatgg cgatgcctgc                                      30

<210> SEQ ID NO 15
<211> LENGTH: 51
```

```
<212> TYPE: DNA
<213> ORGANISM: Artificial Sequence
<220> FEATURE:
<223> OTHER INFORMATION: Synthesized Construct

<400> SEQUENCE: 15
attaaaccta ggttaattaa gtttaaacga cctataaagt caaatgcaaa t          51

<210> SEQ ID NO 16
<211> LENGTH: 54
<212> TYPE: DNA
<213> ORGANISM: Artificial Sequence
<220> FEATURE:
<223> OTHER INFORMATION: Synthesized Construct

<400> SEQUENCE: 16
tttaattcat gagacgtctt tgcgatcgcg cagaagagag agagagagag gtag       54

<210> SEQ ID NO 17
<211> LENGTH: 50
<212> TYPE: DNA
<213> ORGANISM: Artificial Sequence
<220> FEATURE:
<223> OTHER INFORMATION: Synthesized Construct

<400> SEQUENCE: 17
attaaaccta ggttaattaa gtttaaacga ttcgacaata tttatcaaat            50

<210> SEQ ID NO 18
<211> LENGTH: 51
<212> TYPE: DNA
<213> ORGANISM: Artificial Sequence
<220> FEATURE:
<223> OTHER INFORMATION: Synthesized Construct

<400> SEQUENCE: 18
tttaattcat gagacgtctt tgcgatcgcg gcgccggcgg cgttggcagg t          51

<210> SEQ ID NO 19
<211> LENGTH: 40
<212> TYPE: DNA
<213> ORGANISM: Artificial Sequence
<220> FEATURE:
<223> OTHER INFORMATION: Synthesized Construct

<400> SEQUENCE: 19
attaaagcga tcgcaccatg gctgccaccg tcgccgtgga                       40

<210> SEQ ID NO 20
<211> LENGTH: 32
<212> TYPE: DNA
<213> ORGANISM: Artificial Sequence
<220> FEATURE:
<223> OTHER INFORMATION: Synthesized Construct

<400> SEQUENCE: 20
tagtgagacg tcttagtcac gatactctga ca                               32

<210> SEQ ID NO 21
<211> LENGTH: 40
<212> TYPE: DNA
<213> ORGANISM: Artificial Sequence
<220> FEATURE:
<223> OTHER INFORMATION: Synthesized Construct

<400> SEQUENCE: 21
attaaagcga tcgcaccatg gccgccagcg tcaccgtgga                       40
```

<210> SEQ ID NO 22
<211> LENGTH: 33
<212> TYPE: DNA
<213> ORGANISM: Artificial Sequence
<220> FEATURE:
<223> OTHER INFORMATION: Synthesized Construct

<400> SEQUENCE: 22
tagtgagacg tcttagtcgc ggtactcggc caa    33

<210> SEQ ID NO 23
<211> LENGTH: 40
<212> TYPE: DNA
<213> ORGANISM: Artificial Sequence
<220> FEATURE:
<223> OTHER INFORMATION: Synthesized Construct

<400> SEQUENCE: 23
attaaagcga tcgcaccatg gctgctccca gcgtcgccgt    40

<210> SEQ ID NO 24
<211> LENGTH: 36
<212> TYPE: DNA
<213> ORGANISM: Artificial Sequence
<220> FEATURE:
<223> OTHER INFORMATION: Synthesized Construct

<400> SEQUENCE: 24
tagtgagacg tctcagtcgc ggtacgctgc catgaa    36

<210> SEQ ID NO 25
<211> LENGTH: 41
<212> TYPE: DNA
<213> ORGANISM: Artificial Sequence
<220> FEATURE:
<223> OTHER INFORMATION: Synthesized Construct

<400> SEQUENCE: 25
attaaagcga tcgcaccatg cggagattcg tgattggcca a    41

<210> SEQ ID NO 26
<211> LENGTH: 36
<212> TYPE: DNA
<213> ORGANISM: Artificial Sequence
<220> FEATURE:
<223> OTHER INFORMATION: Synthesized Construct

<400> SEQUENCE: 26
tagtgagacg tcttagtcgc ggaactcgtc catgaa    36

<210> SEQ ID NO 27
<211> LENGTH: 38
<212> TYPE: DNA
<213> ORGANISM: Artificial Sequence
<220> FEATURE:
<223> OTHER INFORMATION: Synthesized Construct

<400> SEQUENCE: 27
attaaagcga tcgcaccatg gattccatca ctattgat    38

<210> SEQ ID NO 28
<211> LENGTH: 33
<212> TYPE: DNA
<213> ORGANISM: Artificial Sequence
<220> FEATURE:
<223> OTHER INFORMATION: Synthesized Construct

<400> SEQUENCE: 28
tagtgagacg tcttagccgc agaattcatc cat                          33

<210> SEQ ID NO 29
<211> LENGTH: 482
<212> TYPE: PRT
<213> ORGANISM: Hordeum vulgare

<400> SEQUENCE: 29

```
Met Ala Ala Thr Val Ala Val Asp Asn Leu Asn Pro Lys Val Leu Lys
 1               5                  10                  15

Cys Glu Tyr Ala Val Arg Gly Glu Ile Val Ile His Ala Gln Arg Leu
            20                  25                  30

Gln Glu Gln Leu Lys Thr Gln Pro Gly Ser Leu Pro Phe Asp Glu Ile
        35                  40                  45

Leu Tyr Cys Asn Ile Gly Asn Pro Gln Ser Leu Gly Gln Gln Pro Val
    50                  55                  60

Thr Phe Phe Arg Glu Val Leu Ala Leu Cys Asp His Pro Asp Leu Leu
65                  70                  75                  80

Gln Arg Glu Glu Ile Lys Thr Leu Phe Ser Ala Asp Ser Ile Ser Arg
                85                  90                  95

Ala Lys Gln Ile Leu Ala Met Ile Pro Gly Arg Ala Thr Gly Ala Tyr
            100                 105                 110

Ser His Ser Gln Gly Ile Lys Gly Leu Arg Asp Ala Ile Ala Ser Gly
        115                 120                 125

Ile Ala Ser Arg Asp Gly Phe Pro Ala Asn Ala Asp Asp Ile Phe Leu
    130                 135                 140

Thr Asp Gly Ala Ser Pro Gly Val His Leu Met Met Gln Leu Leu Ile
145                 150                 155                 160

Arg Asn Glu Lys Asp Gly Ile Leu Val Pro Ile Pro Gln Tyr Pro Leu
                165                 170                 175

Tyr Ser Ala Ser Ile Ala Leu His Gly Gly Ala Leu Val Pro Tyr Tyr
            180                 185                 190

Leu Asn Glu Ser Thr Gly Trp Gly Leu Glu Thr Ser Asp Val Lys Lys
        195                 200                 205

Gln Leu Glu Asp Ala Arg Ser Arg Gly Ile Asn Val Arg Ala Leu Val
    210                 215                 220

Val Ile Asn Pro Gly Asn Pro Thr Gly Gln Val Leu Ala Glu Glu Asn
225                 230                 235                 240

Gln Tyr Asp Ile Val Lys Phe Cys Lys Asn Glu Gly Leu Val Leu Leu
                245                 250                 255

Ala Asp Glu Val Tyr Gln Glu Asn Ile Tyr Val Asp Asn Lys Lys Phe
            260                 265                 270

His Ser Phe Lys Lys Ile Val Arg Ser Leu Gly Tyr Gly Glu Glu Asp
        275                 280                 285

Leu Pro Leu Val Ser Tyr Gln Ser Val Ser Lys Gly Tyr Tyr Gly Glu
    290                 295                 300

Cys Gly Lys Arg Gly Gly Tyr Phe Glu Ile Thr Gly Phe Ser Ala Pro
305                 310                 315                 320

Val Arg Glu Gln Ile Tyr Lys Ile Ala Ser Val Asn Leu Cys Ser Asn
                325                 330                 335

Ile Thr Gly Gln Ile Leu Ala Ser Leu Val Met Asn Pro Pro Lys Ala
            340                 345                 350

Ser Asp Glu Ser Tyr Ala Ser Tyr Lys Ala Glu Lys Asp Gly Ile Leu
```

```
                355                 360                 365
Ala Ser Leu Ala Arg Arg Ala Lys Ala Leu Glu His Ala Phe Asn Lys
370                 375                 380

Leu Glu Gly Ile Thr Cys Asn Glu Ala Glu Gly Ala Met Tyr Val Phe
385                 390                 395                 400

Pro Gln Ile Cys Leu Pro Gln Lys Ala Ile Glu Ala Ala Lys Ala Ala
                405                 410                 415

Asn Lys Ala Pro Asp Ala Phe Tyr Ala Leu Arg Leu Leu Glu Ser Thr
            420                 425                 430

Gly Ile Val Val Pro Gly Ser Gly Phe Gly Gln Val Pro Gly Thr
            435                 440                 445

Trp His Phe Arg Cys Thr Ile Leu Pro Gln Glu Asp Lys Ile Pro Ala
    450                 455                 460

Val Ile Ser Arg Phe Thr Val Phe His Glu Ala Phe Met Ser Glu Tyr
465                 470                 475                 480

Arg Asp

<210> SEQ ID NO 30
<211> LENGTH: 482
<212> TYPE: PRT
<213> ORGANISM: Panicum miliaceum

<400> SEQUENCE: 30

Met Ala Ala Thr Val Ala Val Glu Asn Leu Asn Pro Lys Val Leu Lys
1               5                   10                  15

Cys Glu Tyr Ala Val Arg Gly Glu Ile Val Ile His Ala Gln His Leu
            20                  25                  30

Gln Gln Gln Leu Gln Thr Gln Pro Gly Ser Leu Pro Phe Asp Glu Ile
        35                  40                  45

Leu Tyr Cys Asn Ile Gly Asn Pro Gln Ser Leu Gly Gln Gln Pro Val
    50                  55                  60

Thr Phe Phe Arg Glu Val Leu Ala Leu Cys Asp His Pro Cys Leu Leu
65                  70                  75                  80

Glu Lys Glu Glu Thr Lys Ser Leu Phe Ser Ala Asp Ala Ile Ser Arg
                85                  90                  95

Ala Lys Gln Ile Leu Ser Thr Ile Pro Gly Arg Ala Thr Gly Ala Tyr
            100                 105                 110

Ser His Ser Gln Gly Ile Lys Gly Leu Arg Asp Ala Ile Ala Ala Gly
        115                 120                 125

Ile Ala Ser Arg Asp Gly Phe Pro Ala Asn Ala Asp Asp Ile Phe Val
130                 135                 140

Thr Asp Gly Ala Ser Pro Gly Val His Met Met Met Gln Leu Leu Ile
145                 150                 155                 160

Arg Asn Glu Lys Asp Gly Ile Leu Cys Pro Ile Pro Gln Tyr Pro Leu
                165                 170                 175

Tyr Ser Ala Ser Ile Ala Leu His Gly Gly Thr Leu Val Pro Tyr Tyr
            180                 185                 190

Leu Asp Glu Lys Thr Gly Trp Gly Leu Glu Ile Ser Asp Leu Lys Lys
        195                 200                 205

Gln Leu Glu Asp Ala Arg Ser Lys Gly Ile Asp Val Arg Ala Leu Val
    210                 215                 220

Val Ile Asn Pro Gly Asn Pro Thr Gly Gln Val Leu Ala Glu Asp Asn
225                 230                 235                 240

Gln Cys Asp Ile Val Arg Phe Cys Lys Asn Glu Gly Leu Val Leu Leu
                245                 250                 255
```

Ala Asp Glu Val Tyr Gln Glu Asn Ile Tyr Val Asp Lys Lys Phe
          260                 265                 270

Asn Ser Phe Lys Lys Ile Ala Arg Ser Val Gly Tyr Gly Glu Asp Asp
      275                 280                 285

Leu Pro Leu Val Ser Phe Gln Ser Val Ser Lys Gly Tyr Tyr Gly Glu
      290                 295                 300

Cys Gly Lys Arg Gly Gly Tyr Met Glu Ile Thr Gly Phe Ser Ala Pro
305                 310                 315                 320

Val Arg Glu Gln Ile Tyr Lys Ile Ala Ser Val Asn Leu Cys Ser Asn
              325                 330                 335

Ile Thr Gly Gln Ile Leu Ala Ser Leu Val Met Asn Pro Pro Lys Val
          340                 345                 350

Gly Asp Glu Ser Tyr Ala Ala Tyr Lys Ala Glu Lys Asp Gly Ile Leu
      355                 360                 365

Gln Ser Leu Ala Arg Arg Ala Lys Ala Leu Glu Asp Ala Phe Asn Asn
      370                 375                 380

Leu Glu Gly Ile Ser Cys Asn Lys Ala Glu Gly Ala Met Tyr Leu Phe
385                 390                 395                 400

Pro Gln Ile His Leu Pro Lys Lys Ala Ile Glu Ala Ala Lys Ala Ala
              405                 410                 415

Asn Lys Ala Pro Asp Ala Phe Tyr Ala Leu Arg Leu Leu Glu Ser Thr
          420                 425                 430

Gly Ile Val Val Val Pro Gly Ser Gly Phe Gly Gln Val Pro Gly Thr
      435                 440                 445

Trp His Ile Arg Cys Thr Ile Leu Pro Gln Glu Asp Lys Ile Pro Ala
      450                 455                 460

Val Ile Thr Arg Phe Lys Ala Phe His Glu Ala Phe Met Ala Glu Tyr
465                 470                 475                 480

Arg Asp

<210> SEQ ID NO 31
<211> LENGTH: 482
<212> TYPE: PRT
<213> ORGANISM: Oryza sativa

<400> SEQUENCE: 31

Ala Ala Pro Ser Val Ala Val Asp Asn Leu Asn Pro Lys Val Leu Asn
1               5                   10                  15

Cys Glu Tyr Ala Val Arg Gly Glu Ile Val Ile His Ala Gln Arg Leu
              20                  25                  30

Gln Gln Gln Leu Gln Thr Gln Pro Gly Ser Leu Pro Phe Asp Glu Ile
          35                  40                  45

Leu Tyr Cys Asn Ile Gly Asn Pro Gln Ser Leu Gly Gln Lys Pro Val
      50                  55                  60

Thr Phe Phe Arg Glu Val Ile Ala Leu Cys Asp His Pro Cys Leu Leu
65                  70                  75                  80

Glu Lys Glu Glu Thr Lys Ser Leu Phe Ser Ala Asp Ala Ile Ser Arg
              85                  90                  95

Ala Thr Thr Ile Leu Ala Ser Ile Pro Gly Arg Ala Thr Gly Ala Tyr
          100                 105                 110

Ser His Ser Gln Gly Ile Lys Gly Leu Arg Asp Ala Ile Ala Ala Gly
      115                 120                 125

Ile Ala Ser Arg Asp Gly Tyr Pro Ala Asn Ala Asp Asp Ile Phe Leu
      130                 135                 140

Thr Asp Gly Ala Ser Pro Gly Val His Met Met Gln Leu Leu Ile
145                 150                 155                 160

Arg Asn Glu Lys Asp Gly Ile Leu Cys Pro Ile Pro Gln Tyr Pro Leu
            165                 170                 175

Tyr Ser Ala Ser Ile Ala Leu His Gly Gly Ala Leu Val Pro Tyr Tyr
            180                 185                 190

Leu Asn Glu Ser Thr Gly Trp Gly Leu Glu Ile Ser Asp Leu Lys Lys
            195                 200                 205

Gln Leu Glu Asp Ser Arg Leu Lys Gly Ile Asp Val Arg Ala Leu Val
        210                 215                 220

Val Ile Asn Pro Gly Asn Pro Thr Gly Gln Val Leu Ala Glu Glu Asn
225                 230                 235                 240

Gln Arg Asp Ile Val Lys Phe Cys Lys Asn Glu Gly Leu Val Leu Leu
            245                 250                 255

Ala Asp Glu Val Tyr Gln Glu Asn Ile Tyr Val Asp Asn Lys Lys Phe
            260                 265                 270

Asn Ser Phe Lys Lys Ile Ala Arg Ser Met Gly Tyr Asn Glu Asp Asp
        275                 280                 285

Leu Pro Leu Val Ser Phe Gln Ser Val Ser Lys Gly Tyr Tyr Gly Glu
    290                 295                 300

Cys Gly Lys Arg Gly Gly Tyr Met Glu Ile Thr Gly Phe Ser Ala Pro
305                 310                 315                 320

Val Arg Glu Gln Ile Tyr Lys Val Ala Ser Val Asn Leu Cys Ser Asn
            325                 330                 335

Ile Thr Gly Gln Ile Leu Ala Ser Leu Val Met Asn Pro Pro Lys Ala
            340                 345                 350

Gly Asp Ala Ser Tyr Ala Ser Tyr Lys Ala Glu Lys Asp Gly Ile Leu
        355                 360                 365

Gln Ser Leu Ala Arg Arg Ala Lys Ala Leu Glu Asn Ala Phe Asn Ser
    370                 375                 380

Leu Glu Gly Ile Thr Cys Asn Lys Thr Glu Gly Ala Met Tyr Leu Phe
385                 390                 395                 400

Pro Gln Leu Ser Leu Pro Gln Lys Ala Ile Asp Ala Ala Lys Ala Ala
            405                 410                 415

Asn Lys Ala Pro Asp Ala Phe Tyr Ala Leu Arg Leu Leu Glu Ala Thr
            420                 425                 430

Gly Ile Val Val Pro Gly Ser Gly Phe Gly Gln Val Pro Gly Thr
        435                 440                 445

Trp His Ile Arg Cys Thr Leu Pro Gln Glu Glu Lys Ile Pro Ala
    450                 455                 460

Ile Ile Ser Arg Phe Lys Ala Phe His Glu Gly Phe Met Ala Ala Tyr
465                 470                 475                 480

Arg Asp

<210> SEQ ID NO 32
<211> LENGTH: 480
<212> TYPE: PRT
<213> ORGANISM: Oryza sativa

<400> SEQUENCE: 32

Gly Ala Ala Pro Val Ser Leu Asp Thr Ile Asn Pro Lys Val Leu Lys
1               5                   10                  15

Cys Glu Tyr Ala Val Arg Gly Glu Ile Val Thr His Ala Gln Leu Gln
            20                  25                  30

Gln Glu Leu Gln Lys Asn Pro Asp Ser Leu Pro Phe Asp Glu Ile Leu

-continued

```
                35                  40                  45
Tyr Cys Asn Ile Gly Asn Pro Gln Ser Leu Gly Gln Gln Pro Val Thr
 50                  55                  60
Phe Phe Arg Glu Val Leu Ser Leu Cys Asp His Pro Ala Leu Leu Asp
 65                  70                  75                  80
Lys Ser Glu Thr His Ala Leu Tyr Ser Asp Ala Ile Glu Arg Ala Trp
                 85                  90                  95
Gln Ile Leu Asp Lys Ile Pro Gly Arg Ala Thr Gly Ala Tyr Ser His
                100                 105                 110
Ser Gln Gly Ile Lys Gly Leu Arg Asp Glu Ile Ala Ala Gly Ile Ala
                115                 120                 125
Ala Arg Asp Gly Phe His Ala Ser Gly Asp Asn Ile Phe Leu Thr Asp
130                 135                 140
Gly Ala Ser Pro Ala Val His Met Met Met Gln Leu Leu Ile Arg Ser
145                 150                 155                 160
Glu Asn Asp Gly Ile Leu Cys Pro Ile Pro Gln Tyr Pro Leu Tyr Ser
                165                 170                 175
Ala Ser Ile Ala Leu His Gly Gly Ser Leu Val Pro Tyr Phe Leu Asp
                180                 185                 190
Glu Glu Thr Gly Trp Gly Leu Glu Val Asp Glu Leu Lys Lys Gln Leu
                195                 200                 205
Glu Glu Ala Gln Ser Lys Gly Ile Thr Val Arg Ala Leu Val Val Ile
                210                 215                 220
Asn Pro Gly Asn Pro Thr Gly Gln Val Leu Ala Glu Glu Asn Gln Lys
225                 230                 235                 240
Lys Ile Val Glu Phe Cys Lys Asn Glu Gly Leu Val Leu Leu Ala Asp
                245                 250                 255
Glu Val Tyr Gln Glu Asn Ile Tyr Val Glu Asp Lys Lys Phe His Ser
                260                 265                 270
Phe Lys Lys Ile Ala Arg Ser Met Gly Tyr Thr Asp Asp Leu Pro
                275                 280                 285
Leu Val Ser Phe Gln Ser Val Ser Lys Gly Tyr Tyr Gly Glu Cys Gly
                290                 295                 300
Lys Arg Gly Gly Tyr Met Glu Val Thr Gly Phe Ser Ala Asp Val Arg
305                 310                 315                 320
Glu Gln Ile Tyr Lys Val Ala Ser Val Asn Leu Cys Ser Asn Val Ser
                325                 330                 335
Gly Gln Leu Leu Ala Ser Leu Ile Met Asn Pro Pro Lys Ala Gly Asp
                340                 345                 350
Glu Ser Tyr Glu Ser Phe Met Val Glu Lys Asp Gly Ile Leu Ser Ser
                355                 360                 365
Leu Ala Arg Arg Ala Lys Ala Leu Glu Glu Ala Phe Asn Ser Leu Glu
                370                 375                 380
Gly Ile Thr Cys Asn Lys Ala Glu Gly Ala Met Tyr Leu Phe Pro Arg
385                 390                 395                 400
Ile Tyr Leu Pro Gln Lys Ala Ile Gly Ala Ala Gln Ala Ala Gly Thr
                405                 410                 415
Ala Pro Asp Ala Tyr Tyr Ala Arg Arg Leu Leu Glu Ala Thr Gly Ile
                420                 425                 430
Val Val Val Pro Gly Ser Gly Phe Gly Gln Val Pro Gly Thr Trp His
                435                 440                 445
Phe Arg Cys Thr Ile Leu Pro Gln Glu Asp Lys Ile Pro Ala Ile Ile
450                 455                 460
```

```
Ser Lys Phe Lys Glu Phe His Glu Lys Phe Met Asp Glu Phe Arg Asp
465                 470                 475                 480
```

<210> SEQ ID NO 33
<211> LENGTH: 475
<212> TYPE: PRT
<213> ORGANISM: Oryza sativa

<400> SEQUENCE: 33

```
Ala Ala Arg Ala Leu Thr Val Ser Ser Leu Asn Pro Lys Val Leu Ala
  1               5                  10                  15

Leu Ala Asp His His Leu Gly Gly Leu Val Ala Arg Arg Ala Gln Leu
             20                  25                  30

Val Thr Val Thr Val Asn Ile Leu Ile Val Glu Arg Lys Lys Ile Leu
         35                  40                  45

Gln Ala Asp Thr Ser Met Gln Gln Glu Leu Asp Ala Asn Pro Ala Ser
 50                  55                  60

His Pro Phe Ser Glu Val Leu Ala Leu Cys Asn His Pro His Leu Leu
 65                  70                  75                  80

Asp Arg Ser Glu Ala Ser Phe Met Phe Ser Ser Asp Ala Ile Thr Arg
                 85                  90                  95

Ala Arg Glu Ile Val Gly Phe Ile Pro Gly Lys Thr Thr Gly Gly Tyr
            100                 105                 110

Ser His Cys Gln Ala Asn Ser Ile Val Ser Glu Phe Arg Ala Asn Ala
        115                 120                 125

Asp Lys Tyr Gly Asn Glu Leu Ser Ser Asn Leu Thr Ile Phe Asp Arg
    130                 135                 140

Val His Met Met Met His Leu Leu Ile Arg Gly Lys Lys Asp Gly Ile
145                 150                 155                 160

Leu Cys Pro Ile Pro Ser His Ser Leu Tyr Thr Asp Ser Met Val Leu
                165                 170                 175

Arg Gly Ala Thr Leu Val Pro Tyr Tyr Leu Asp Glu Ser Arg Gly Trp
            180                 185                 190

Ser Val Asn Ile Ser Asp Leu Lys Lys Gln Leu Asp Gly Ala Arg Ala
        195                 200                 205

Lys Gly Ile Asp Val Arg Gly Leu Val Val Asn Pro Gly Asn Pro
    210                 215                 220

Thr Gly Gln Val Leu Val Glu Glu Asn Gln Cys Glu Ile Val Glu Leu
225                 230                 235                 240

Cys Lys Asn Glu Cys Leu Val Leu Leu Ala Asp Glu Val Tyr Gln Glu
                245                 250                 255

Asn Ile Tyr Thr Asp Gln Lys Lys Phe Asn Ser Phe Lys Lys Val Ala
            260                 265                 270

Arg Ser Ile Gly Tyr Gly Glu Gly Asp Ile Ser Leu Val Ser Phe His
        275                 280                 285

Ser Val Ser Asn Gly Tyr Tyr Gly Glu Cys Gly Arg Arg Gly Gly Tyr
    290                 295                 300

Met Glu Val Thr Gly Phe Ser Ser Glu Val Arg Gly Glu Val Tyr Lys
305                 310                 315                 320

Val Ala Ser Leu Ser Ala Cys Ser Asn Ile Ser Gly Gln Ile Leu Met
                325                 330                 335

Ser Leu Val Met Asn Pro Pro Lys Val Gly Asp Glu Ser Tyr Pro Ser
            340                 345                 350

Tyr Arg Ala Glu Arg Asp Ser Ile Leu Ser Ser Leu Ser Cys Cys Ala
        355                 360                 365
```

-continued

Glu Ala Met Val Ser Thr Phe Asn Ser Met Glu Gly Met Thr Cys Asn
            370                 375                 380

Lys Ala Glu Gly Gly Ile Ser Val Phe Pro Ser Val Arg Leu Pro Pro
385                 390                 395                 400

Arg Ala Ile Glu Ala Ala Glu Ala Met Asn Thr Glu Pro Asp Val Phe
                405                 410                 415

Tyr Ala Leu Arg Leu Leu Glu Ser Thr Gly Ile Val Val Pro Gly
                420                 425                 430

Ser Val Phe Gly Gln Val Pro Gly Thr Trp His Phe Arg Cys Thr Ile
            435                 440                 445

Leu Pro Gln Glu Glu Lys Thr Arg Gln Ile Ile Ser Arg Phe Asn Val
    450                 455                 460

Phe His Glu Ala Phe Met Glu Glu Phe Arg Ser
465                 470                 475

<210> SEQ ID NO 34
<211> LENGTH: 482
<212> TYPE: PRT
<213> ORGANISM: Oryza sativa

<400> SEQUENCE: 34

His Ser Pro Ser Ile Thr Ala Glu Thr Ile Asn Gln Lys Val Arg Ile
1               5                   10                  15

Phe Thr Tyr Glu Pro Cys Gly Glu Ile Val Arg His Ala Arg Arg Leu
                20                  25                  30

Glu Lys Glu Ile Tyr Glu Asn Pro Gly Ser Leu Pro Phe Gln Glu Ile
            35                  40                  45

Ile Tyr Cys Asn Leu Gly Asn Pro Gln Ala Leu Gly Gln Arg Pro Ile
        50                  55                  60

Asn Phe Phe Arg Glu Val Leu Ser Leu Cys Asp Asn Pro Ser Leu Ile
65              70                  75                  80

Asp Arg Asp Glu Ala Arg Ala Leu Phe Ser Pro Cys Ala Leu Lys Arg
                85                  90                  95

Ala Arg Lys Ile Ile Glu Ser Leu Pro Gly Arg Asp Ser Gly Ser Tyr
            100                 105                 110

Thr Ser Ser Gln Gly Val Arg Gly Leu Arg Glu Ala Val Ala Asp Gly
        115                 120                 125

Ile Ala Ala Arg Asp Gly Phe Pro Ser Lys Pro Asp Asn Ile Phe Leu
130                 135                 140

Thr Asp Gly Ala Ser Ser Ala Ile Asn Met Met Met Gln Ile Leu Ile
145                 150                 155                 160

Arg Ser His Glu Asp Gly Ile Leu Cys Pro Leu Pro Glu Tyr Pro Leu
                165                 170                 175

Tyr Ser Ala Ser Ile Ile Leu His Gly Gly Thr Met Val Pro Tyr Asn
            180                 185                 190

Leu Thr Glu Asp Ser Ile Trp Gly Leu Glu Ile Phe Glu Val Lys Arg
        195                 200                 205

Cys Leu Glu Asp Ala Arg Ala Ser Gly Leu Thr Ile Arg Ala Met Val
210                 215                 220

Val Ile Asn Pro Gly Asn Pro Thr Gly Gln Val Leu Ser Ile Thr Asn
225                 230                 235                 240

Gln Glu Glu Ile Val Glu Phe Cys Arg Lys Gly Leu Val Ile Leu
                245                 250                 255

Ala Asp Glu Val Tyr Gln Glu Asn Val Tyr Thr Glu Asn Lys Arg Phe
            260                 265                 270

```
Asn Ser Phe Lys Lys Val Ala Arg Ser Leu Gly Tyr Asp His His Asp
        275                 280                 285

Leu Ser Ile Val Ser Phe His Ser Val Ser Met Gly Tyr Tyr Gly Glu
290                 295                 300

Cys Gly Arg Arg Gly Gly Tyr Met Glu Ile Cys Gly Phe Gly Asp Asp
305                 310                 315                 320

Val Ile Asp Glu Met Tyr Lys Leu Ala Ser Leu Thr Ile Cys Pro Asn
            325                 330                 335

Ile Ala Gly Gln Ile Leu Ile Ser Leu Val Met Asp Pro Pro Lys Leu
            340                 345                 350

Gly Asp Glu Ala Phe Glu Ile Phe Met Val Glu Lys Glu Thr Tyr
        355                 360                 365

Ser Ser Leu Leu Lys Arg Ala Lys Ala Leu Gln Lys Ala Phe Asn Gly
        370                 375                 380

Leu Glu Gly Val Ser Cys Asn Lys Phe Glu Gly Ala Met Tyr Leu Phe
385                 390                 395                 400

Pro Arg Leu Arg Leu Pro Gln Ala Ala Ile Lys Ala Ala Gln Leu Glu
                405                 410                 415

Gly Val Ser Pro Asp Val Phe Tyr Ala His Arg Leu Leu Asp Ala Thr
            420                 425                 430

Gly Ile Ala Val Val Pro Gly Ser Gly Phe His Pro Val Ser Gly Thr
            435                 440                 445

Ser His Ile Arg Cys Thr Ile Leu Pro Gly Glu Glu Thr Ile Thr Ala
    450                 455                 460

Met Val Pro Ser Leu Gln Ala Phe His Glu Ala Phe Met Asp Glu Phe
465                 470                 475                 480

Arg Gly

<210> SEQ ID NO 35
<211> LENGTH: 482
<212> TYPE: PRT
<213> ORGANISM: Zea mays

<400> SEQUENCE: 35

Met Ala Ala Ser Val Thr Val Glu Asn Leu Asn Pro Lys Val Leu Lys
1               5                   10                  15

Cys Glu Tyr Ala Val Arg Gly Glu Ile Val Ile His Ala Gln Arg Arg
            20                  25                  30

Gln Gln Gln Leu Gln Thr Gln Pro Gly Ser Leu Pro Phe Asp Glu Ile
        35                  40                  45

Leu Tyr Cys Asn Ile Gly Asn Pro Gln Ser Leu Gly Gln Gln Pro Val
50                  55                  60

Thr Phe Phe Arg Glu Val Leu Ala Leu Cys Asp His Pro Cys Leu Leu
65                  70                  75                  80

Glu Lys Glu Glu Thr Lys Ser Leu Phe Ser Ala Asp Ala Ile Ser Arg
                85                  90                  95

Ala Lys Gln Ile Leu Ala Thr Ile Pro Gly Arg Ala Thr Gly Ala Tyr
            100                 105                 110

Ser His Ser Gln Gly Ile Lys Gly Leu Arg Asp Ala Ile Ala Ala Gly
        115                 120                 125

Ile Met Ser Arg Asp Gly Phe Pro Ala Asn Ala Asp Asp Ile Phe Ile
    130                 135                 140

Thr Asp Gly Ala Ser Pro Gly Val His Met Met Met Gln Leu Leu Ile
145                 150                 155                 160

Arg Asn Glu Lys Asp Gly Ile Leu Cys Pro Ile Pro Gln Tyr Pro Leu
```

```
                            165                 170                 175
Tyr Ser Ala Ser Ile Ala Leu His Gly Gly Thr Leu Val Pro Tyr Tyr
            180                 185                 190

Leu Asn Glu Lys Asn Gly Trp Gly Leu Glu Ile Ser Asp Phe Lys Thr
        195                 200                 205

Arg Leu Glu Asp Val Arg Ser Lys Gly Ile Asp Val Arg Ala Leu Val
    210                 215                 220

Val Ile Asn Pro Gly Asn Pro Thr Gly Gln Val Leu Ala Glu Asp Asn
225                 230                 235                 240

Gln Tyr Asp Ile Val Lys Phe Cys Lys Asn Glu Gly Leu Val Leu Leu
                245                 250                 255

Ala Asp Glu Val Tyr Gln Glu Asn Ile Tyr Val Asp Asn Lys Lys Phe
            260                 265                 270

Asn Ser Phe Lys Lys Ile Val Arg Ser Met Gly Tyr Gly Glu Asp Asp
        275                 280                 285

Leu Pro Leu Val Ser Leu Gln Ser Val Ser Lys Gly Tyr Tyr Gly Glu
    290                 295                 300

Cys Gly Lys Arg Gly Gly Tyr Met Glu Ile Thr Gly Phe Ser Ala Pro
305                 310                 315                 320

Val Arg Glu Gln Ile Tyr Lys Ile Ala Ser Val Asn Leu Cys Ser Asn
                325                 330                 335

Ile Thr Gly Gln Ile Leu Ala Ser Leu Val Met Asn Pro Pro Lys Ala
            340                 345                 350

Gly Asp Glu Ser Tyr Ala Ser Tyr Lys Ala Glu Lys Asp Gly Ile Leu
        355                 360                 365

Glu Ser Leu Ala Arg Arg Ala Lys Ala Leu Glu Asp Ala Phe Asn Lys
    370                 375                 380

Leu Glu Gly Phe Ser Cys Asn Lys Ala Glu Gly Ala Met Tyr Leu Phe
385                 390                 395                 400

Pro Gln Ile His Leu Pro Gln Lys Ala Ile Glu Ala Ala Lys Ala Ala
                405                 410                 415

Lys Lys Ala Pro Asp Ala Phe Tyr Ala Leu Arg Leu Leu Glu Ser Thr
            420                 425                 430

Gly Ile Val Val Pro Gly Ser Gly Phe Gly Gln Val Pro Gly Thr
        435                 440                 445

Trp His Ile Arg Cys Thr Ile Leu Pro Gln Glu Asp Lys Ile Pro Ala
    450                 455                 460

Val Ile Ser Arg Phe Arg Ala Phe His Glu Ala Phe Leu Ala Glu Tyr
465                 470                 475                 480

Arg Asp

<210> SEQ ID NO 36
<211> LENGTH: 482
<212> TYPE: PRT
<213> ORGANISM: Arabidopsis thaliana

<400> SEQUENCE: 36

Ser Ser Leu Pro Val Thr Leu Asp Thr Ile Asn Pro Lys Val Ile Lys
1               5                   10                  15

Cys Glu Tyr Ala Val Arg Gly Glu Ile Val Asn Ile Ala Gln Lys Leu
            20                  25                  30

Gln Glu Asp Leu Lys Thr Asn Lys Asp Ala Tyr Pro Phe Asp Glu Ile
        35                  40                  45

Ile Tyr Cys Asn Ile Gly Asn Pro Gln Ser Leu Gly Gln Gln Pro Ile
    50                  55                  60
```

```
Thr Phe Phe Arg Glu Val Leu Ala Leu Cys Ser Tyr Thr Ala Leu Leu
 65                  70                  75                  80

Asp Glu Ser Ala Thr His Gly Leu Phe Ser Ser Asp Ser Ile Glu Arg
                 85                  90                  95

Ala Trp Lys Ile Leu Asp Gln Ile Pro Gly Arg Ala Thr Gly Ala Tyr
            100                 105                 110

Ser His Ser Gln Gly Ile Lys Gly Leu Arg Asp Ala Ile Ala Asp Gly
        115                 120                 125

Ile Glu Ala Arg Asp Gly Phe Pro Ala Asp Pro Asn Asp Ile Phe Met
    130                 135                 140

Thr Asp Gly Ala Ser Pro Gly Val His Met Met Gln Leu Leu Ile
145                 150                 155                 160

Thr Ser Glu Lys Asp Gly Ile Leu Cys Pro Ile Pro Gln Tyr Pro Leu
                165                 170                 175

Tyr Ser Ala Ser Ile Ala Leu His Gly Gly Thr Leu Val Pro Tyr Tyr
            180                 185                 190

Leu Asp Glu Ala Ser Gly Trp Gly Leu Glu Ile Ser Glu Leu Lys Lys
        195                 200                 205

Gln Leu Glu Asp Ala Arg Ser Lys Gly Ile Thr Val Arg Ala Leu Ala
    210                 215                 220

Val Ile Asn Pro Gly Asn Pro Thr Gly Gln Val Leu Ser Glu Glu Asn
225                 230                 235                 240

Gln Arg Asp Val Val Lys Phe Cys Lys Gln Glu Gly Leu Val Leu Leu
                245                 250                 255

Ala Asp Glu Val Tyr Gln Glu Asn Val Tyr Val Pro Asp Lys Lys Phe
            260                 265                 270

His Ser Phe Lys Lys Val Ala Arg Ser Met Gly Tyr Gly Glu Lys Asp
        275                 280                 285

Leu Ala Leu Val Ser Phe Gln Ser Val Ser Lys Gly Tyr Tyr Gly Glu
    290                 295                 300

Cys Gly Lys Arg Gly Gly Tyr Met Glu Val Thr Gly Phe Thr Ser Asp
305                 310                 315                 320

Val Arg Glu Gln Ile Tyr Lys Met Ala Ser Val Asn Leu Cys Ser Asn
                325                 330                 335

Ile Ser Gly Gln Ile Leu Ala Ser Leu Ile Met Ser Pro Pro Lys Pro
            340                 345                 350

Gly Asp Asp Ser Tyr Glu Ser Tyr Ile Ala Glu Lys Asp Gly Ile Leu
        355                 360                 365

Ser Ser Leu Ala Arg Arg Ala Lys Thr Leu Glu Glu Ala Leu Asn Lys
    370                 375                 380

Leu Glu Gly Val Thr Cys Asn Arg Ala Glu Gly Ala Met Tyr Leu Phe
385                 390                 395                 400

Pro Cys Leu His Leu Pro Gln Lys Ala Ile Ala Ala Glu Ala
                405                 410                 415

Lys Thr Ala Pro Asp Asn Phe Tyr Cys Lys Arg Leu Leu Lys Ala Thr
            420                 425                 430

Gly Ile Val Val Val Pro Gly Ser Gly Phe Arg Gln Val Pro Gly Thr
        435                 440                 445

Trp His Phe Arg Cys Thr Ile Leu Pro Gln Glu Asp Lys Ile Pro Ala
    450                 455                 460

Ile Val Asp Arg Leu Thr Ala Phe His Gln Ser Phe Met Asp Glu Phe
465                 470                 475                 480

Arg Asp
```

<210> SEQ ID NO 37
<211> LENGTH: 482
<212> TYPE: PRT
<213> ORGANISM: Arabidopsis thaliana

<400> SEQUENCE: 37

```
Ser Ser Leu Pro Val Thr Leu Asp Ser Ile Asn Pro Lys Val Leu Lys
  1               5                  10                  15

Cys Glu Tyr Ala Val Arg Gly Glu Ile Val Asn Ile Ala Gln Lys Leu
             20                  25                  30

Gln Glu Asp Leu Lys Thr Asn Lys Asp Ala Tyr Pro Phe Asp Glu Ile
         35                  40                  45

Ile Tyr Cys Asn Ile Gly Asn Pro Gln Ser Leu Gly Gln Leu Pro Ile
     50                  55                  60

Lys Phe Phe Arg Glu Val Leu Ala Leu Cys Asp His Ala Ser Leu Leu
 65                  70                  75                  80

Asp Glu Ser Glu Thr His Gly Leu Phe Ser Thr Asp Ser Ile Asp Arg
                 85                  90                  95

Ala Trp Arg Ile Leu Asp His Ile Pro Gly Arg Ala Thr Gly Ala Tyr
            100                 105                 110

Ser His Ser Gln Gly Ile Lys Gly Leu Arg Asp Val Ile Ala Ala Gly
        115                 120                 125

Ile Glu Ala Arg Asp Gly Phe Pro Ala Asp Pro Asn Asp Ile Phe Leu
    130                 135                 140

Thr Asp Gly Ala Ser Pro Ala Val His Met Met Met Gln Leu Leu Leu
145                 150                 155                 160

Ser Ser Glu Lys Asp Gly Ile Leu Ser Pro Ile Pro Gln Tyr Pro Leu
                165                 170                 175

Tyr Ser Ala Ser Ile Ala Leu His Gly Gly Ser Leu Val Pro Tyr Tyr
            180                 185                 190

Leu Asp Glu Ala Thr Gly Trp Gly Leu Glu Ile Ser Asp Leu Lys Lys
        195                 200                 205

Gln Leu Glu Glu Ala Arg Ser Lys Gly Ile Ser Val Arg Ala Leu Val
    210                 215                 220

Val Ile Asn Pro Gly Asn Pro Thr Gly Gln Val Leu Ala Glu Glu Asn
225                 230                 235                 240

Gln Arg Asp Ile Val Asn Phe Cys Lys Gln Glu Gly Leu Val Leu Leu
                245                 250                 255

Ala Asp Glu Val Tyr Gln Glu Asn Val Tyr Val Pro Asp Lys Lys Phe
            260                 265                 270

His Ser Phe Lys Lys Val Ala Arg Ser Leu Gly Tyr Gly Glu Lys Asp
        275                 280                 285

Ile Ser Leu Val Ser Tyr Gln Ser Val Ser Lys Gly Tyr Tyr Gly Glu
    290                 295                 300

Cys Gly Lys Arg Gly Gly Tyr Met Glu Val Thr Gly Phe Thr Ser Asp
305                 310                 315                 320

Val Arg Glu Gln Ile Tyr Lys Met Ala Ser Val Asn Leu Cys Ser Asn
                325                 330                 335

Ile Ser Gly Gln Ile Leu Ala Ser Leu Val Met Ser Pro Pro Lys Pro
            340                 345                 350

Gly Asp Asp Ser Tyr Asp Ser Tyr Met Ala Glu Arg Asp Gly Ile Leu
        355                 360                 365

Ser Ser Met Ala Lys Arg Ala Lys Thr Leu Glu Asp Ala Leu Asn Ser
    370                 375                 380
```

```
Leu Glu Gly Val Thr Cys Asn Arg Ala Glu Gly Ala Met Tyr Leu Phe
385                 390                 395                 400

Pro Arg Ile Asn Leu Pro Gln Lys Ala Ile Glu Ala Ala Glu Ala Glu
            405                 410                 415

Lys Thr Ala Pro Asp Ala Phe Tyr Cys Lys Arg Leu Leu Asn Ala Thr
            420                 425                 430

Gly Val Val Val Pro Gly Ser Gly Phe Gly Gln Val Pro Gly Thr
            435                 440                 445

Trp His Phe Arg Cys Thr Ile Leu Pro Gln Glu Asp Lys Ile Pro Ala
    450                 455                 460

Ile Val Asn Arg Leu Thr Glu Phe His Lys Ser Phe Met Asp Glu Phe
465                 470                 475                 480

Arg Asn
```

<210> SEQ ID NO 38
<211> LENGTH: 473
<212> TYPE: PRT
<213> ORGANISM: Arabidopsis thaliana

<400> SEQUENCE: 38

```
Ala Leu Lys Ala Leu Asp Tyr Asp Thr Leu Asn Glu Asn Val Lys Lys
1               5                   10                  15

Cys Gln Tyr Ala Val Arg Gly Glu Leu Tyr Leu Arg Ala Ser Glu Leu
            20                  25                  30

Gln Lys Glu Gly Lys Lys Ile Ile Phe Thr Asn Val Gly Asn Pro His
        35                  40                  45

Ala Leu Gly Gln Lys Pro Leu Thr Phe Pro Arg Gln Val Val Ala Leu
    50                  55                  60

Cys Gln Ala Pro Phe Leu Leu Asp Asp Pro Asn Val Gly Met Leu Phe
65                  70                  75                  80

Pro Ala Asp Ala Ile Ala Arg Ala Lys His Tyr Leu Ser Leu Thr Ser
                85                  90                  95

Gly Gly Leu Gly Ala Tyr Ser Asp Ser Arg Gly Leu Pro Gly Val Arg
            100                 105                 110

Lys Glu Val Ala Glu Phe Ile Gln Arg Arg Asp Gly Tyr Pro Ser Asn
        115                 120                 125

Pro Glu Leu Ile Phe Leu Thr Asp Gly Ala Ser Lys Gly Val Met Gln
    130                 135                 140

Ile Leu Asn Cys Val Ile Arg Gly Asn Gly Asp Gly Ile Leu Val Pro
145                 150                 155                 160

Val Pro Gln Tyr Pro Leu Tyr Ser Ala Thr Ile Ser Leu Leu Gly Gly
                165                 170                 175

Thr Leu Val Pro Tyr Tyr Leu Asp Glu Ser Glu Asn Trp Gly Leu Asp
            180                 185                 190

Val Ala Asn Leu Arg Gln Ser Val Ala Gln Ala Arg Ser Gln Gly Ile
        195                 200                 205

Thr Val Arg Ala Met Val Ile Ile Asn Pro Gly Asn Pro Thr Gly Gln
    210                 215                 220

Cys Leu Ser Glu Ala Asn Ile Arg Glu Ile Leu Lys Phe Cys Tyr Asn
225                 230                 235                 240

Glu Lys Leu Val Leu Leu Gly Asp Glu Val Tyr Gln Gln Asn Ile Tyr
                245                 250                 255

Gln Asp Glu Arg Pro Phe Ile Ser Ser Lys Lys Val Leu Met Glu Met
            260                 265                 270
```

```
Gly Ser Pro Phe Ser Lys Glu Val Gln Leu Val Ser Phe His Thr Val
        275                 280                 285

Ser Lys Gly Tyr Trp Gly Glu Cys Gly Gln Arg Gly Tyr Phe Glu
290                 295                 300

Met Thr Asn Leu Pro Pro Arg Val Val Glu Ile Tyr Lys Val Ala
305                 310                 315                 320

Ser Ile Ala Leu Ser Pro Asn Val Ser Ala Gln Ile Phe Met Gly Leu
                325                 330                 335

Met Val Asn Pro Pro Lys Pro Gly Asp Ile Ser Tyr Asp Gln Phe Ala
                340                 345                 350

Arg Glu Ser Lys Gly Ile Leu Glu Ser Leu Arg Arg Arg Ala Arg Leu
                355                 360                 365

Met Thr Asp Gly Phe Asn Ser Cys Lys Asn Val Val Cys Asn Phe Thr
370                 375                 380

Glu Gly Ala Met Tyr Ser Phe Pro Gln Ile Arg Leu Pro Thr Gly Ala
385                 390                 395                 400

Leu Gln Ala Ala Lys Gln Ala Gly Lys Val Pro Asp Val Phe Tyr Cys
                405                 410                 415

Leu Lys Leu Leu Glu Ala Thr Gly Ile Ser Thr Val Pro Gly Ser Gly
                420                 425                 430

Phe Gly Gln Lys Glu Gly Val Phe His Leu Arg Thr Thr Ile Leu Pro
                435                 440                 445

Ala Glu Asp Glu Met Pro Glu Ile Met Asp Ser Phe Lys Lys Phe Asn
450                 455                 460

Asp Glu Phe Met Thr Gln Tyr Asp Asn
465                 470

<210> SEQ ID NO 39
<211> LENGTH: 473
<212> TYPE: PRT
<213> ORGANISM: Arabidopsis thaliana

<400> SEQUENCE: 39

Ser Leu Lys Ala Leu Asp Tyr Glu Ser Leu Asn Glu Asn Val Lys Asn
1               5                   10                  15

Cys Gln Tyr Ala Val Arg Gly Glu Leu Tyr Leu Arg Ala Ser Glu Leu
                20                  25                  30

Gln Lys Glu Gly Lys Lys Ile Ile Phe Thr Asn Val Gly Asn Pro His
                35                  40                  45

Ala Leu Gly Gln Lys Pro Leu Thr Phe Pro Arg Gln Val Val Ser Leu
                50                  55                  60

Cys Gln Ala Pro Phe Leu Leu Asp Asp Pro Asn Val Gly Met Ile Phe
65                  70                  75                  80

Pro Ala Asp Ala Ile Ala Arg Ala Lys His Tyr Leu Ser Leu Thr Ser
                85                  90                  95

Gly Gly Leu Gly Ala Tyr Ser Ser Ser Arg Gly Leu Pro Gly Val Arg
                100                 105                 110

Lys Glu Val Ala Glu Phe Ile Glu Arg Arg Asp Gly Tyr Pro Ser Asp
                115                 120                 125

Pro Glu Leu Ile Phe Leu Thr Asp Gly Ala Ser Lys Gly Val Met Gln
                130                 135                 140

Ile Leu Asn Cys Val Ile Arg Gly Gln Lys Asp Gly Ile Leu Val Pro
145                 150                 155                 160

Val Pro Gln Tyr Pro Leu Tyr Ser Ala Thr Ile Ser Leu Leu Gly Gly
                165                 170                 175
```

```
Thr Leu Val Pro Tyr Tyr Leu Glu Glu Ser Glu Asn Trp Gly Leu Asp
            180                 185                 190

Val Asn Asn Leu Arg Gln Ser Val Ala Gln Ala Arg Ser Gln Gly Ile
        195                 200                 205

Thr Val Arg Ala Met Val Ile Ile Asn Pro Gly Asn Pro Thr Gly Gln
    210                 215                 220

Cys Leu Ser Glu Ala Asn Ile Arg Glu Ile Leu Arg Phe Cys Cys Asp
225                 230                 235                 240

Glu Arg Leu Val Leu Leu Gly Asp Glu Val Tyr Gln Gln Asn Ile Tyr
                245                 250                 255

Gln Asp Glu Arg Pro Phe Ile Ser Lys Lys Val Leu Met Asp Met
                260                 265                 270

Gly Ala Pro Ile Ser Lys Glu Val Gln Leu Ile Ser Phe His Thr Val
            275                 280                 285

Ser Lys Gly Tyr Trp Gly Glu Cys Gly Gln Arg Gly Gly Tyr Phe Glu
        290                 295                 300

Met Thr Asn Ile Pro Pro Arg Thr Val Glu Glu Ile Tyr Lys Val Ala
305                 310                 315                 320

Ser Ile Ala Leu Ser Pro Asn Val Ser Ala Gln Ile Phe Met Gly Leu
                325                 330                 335

Met Val Ser Pro Pro Lys Pro Gly Asp Ile Ser Tyr Asp Gln Phe Val
            340                 345                 350

Arg Glu Ser Lys Gly Ile Leu Glu Ser Leu Arg Arg Arg Ala Arg Met
        355                 360                 365

Met Thr Asp Gly Phe Asn Ser Cys Lys Asn Val Val Cys Asn Phe Thr
    370                 375                 380

Glu Gly Ala Met Tyr Ser Phe Pro Gln Ile Lys Leu Pro Ser Lys Ala
385                 390                 395                 400

Ile Gln Ala Ala Lys Gln Ala Gly Lys Val Pro Asp Val Phe Tyr Cys
                405                 410                 415

Leu Lys Leu Leu Glu Ala Thr Gly Ile Ser Thr Val Pro Gly Ser Gly
            420                 425                 430

Phe Gly Gln Lys Glu Gly Val Phe His Leu Arg Thr Thr Ile Leu Pro
        435                 440                 445

Ala Glu Glu Glu Met Pro Glu Ile Met Asp Ser Phe Lys Lys Phe Asn
    450                 455                 460

Asp Glu Phe Met Ser Gln Tyr Ala Asp
465                 470
```

<210> SEQ ID NO 40
<211> LENGTH: 481
<212> TYPE: PRT
<213> ORGANISM: Capsicum

<400> SEQUENCE: 40

```
Met Asp Ser Ile Thr Ile Asp Thr Ile Asn Pro Lys Val Leu Lys Cys
1               5                   10                  15

Glu Tyr Ala Val Arg Gly Glu Ile Val Thr Ile Ala Gln Lys Leu Gln
                20                  25                  30

Gln Asp Leu Lys Asp Asn Pro Gly Ser His Pro Phe Asp Glu Ile Leu
            35                  40                  45

Tyr Cys Asn Ile Gly Asn Pro Gln Ser Leu Ala Gln Gln Pro Ile Thr
        50                  55                  60

Phe Phe Arg Glu Val Leu Ala Leu Cys Asp His Pro Ser Ile Leu Asp
65                  70                  75                  80
```

```
Lys Ser Glu Thr Gln Gly Leu Phe Ser Ala Asp Ala Ile Glu Arg Ala
             85                  90                  95

Phe Gln Ile Leu Asp Gln Ile Pro Gly Arg Ala Thr Gly Ala Tyr Ser
            100                 105                 110

His Ser Gln Gly Ile Lys Gly Leu Arg Asp Thr Ile Ala Ser Gly Ile
        115                 120                 125

Glu Ala Arg Asp Gly Phe Pro Ala Asp Pro Asn Asp Leu Phe Leu Thr
    130                 135                 140

Asp Gly Ala Ser Pro Ala Val His Met Met Met Gln Leu Leu Ile Arg
145                 150                 155                 160

Ser Gln Asn Asp Gly Ile Leu Cys Pro Ile Pro Gln Tyr Pro Leu Tyr
                165                 170                 175

Ser Ala Ser Ile Ala Leu His Gly Gly Thr Leu Val Pro Tyr Tyr Leu
            180                 185                 190

Asp Glu Gln Thr Gly Trp Gly Leu Glu Ile Ser Glu Leu Glu His Gln
        195                 200                 205

Leu Asn Thr Ala Lys Ser Asn Gly Ile Asp Val Arg Ala Leu Val Val
    210                 215                 220

Ile Asn Pro Gly Asn Pro Thr Gly Gln Val Leu Gly Glu Ala Asn Gln
225                 230                 235                 240

Arg Glu Ile Val Glu Phe Cys Lys Lys Glu Gly Leu Val Leu Leu Ala
                245                 250                 255

Asp Glu Val Tyr Gln Glu Asn Val Tyr Val Pro Asp Lys Lys Phe His
            260                 265                 270

Ser Phe Lys Lys Ile Thr Arg Ser Met Gly Tyr Gly Lys Glu Asp Ile
        275                 280                 285

Ser Leu Val Ser Phe Gln Ser Val Ser Lys Gly Phe Tyr Gly Glu Cys
    290                 295                 300

Gly Lys Arg Gly Gly Tyr Met Glu Ile Thr Gly Phe Ser Pro Glu Val
305                 310                 315                 320

Arg Glu Gln Ile Tyr Lys Leu Ala Ser Val Asn Leu Cys Ser Asn Ile
                325                 330                 335

Ser Gly Gln Ile Leu Ala Ser Leu Val Met Ser Pro Pro Lys Val Gly
            340                 345                 350

Asp Glu Ser Tyr Glu Ser Phe Ser Ala Glu Lys Glu Ala Val Leu Ser
        355                 360                 365

Ser Leu Ala Arg Arg Ala Gln Ala Leu Gln Asp Ala Leu Asn Ser Leu
    370                 375                 380

Glu Gly Val Thr Cys Asn Arg Ala Glu Gly Ala Met Tyr Leu Phe Pro
385                 390                 395                 400

Arg Ile Asn Leu Pro Asp Lys Ala Ile Lys Ala Ala Glu Val Ala Lys
                405                 410                 415

Thr Ala Pro Asp Ala Phe Tyr Ala Lys Leu Leu Leu Asn Ala Thr Gly
            420                 425                 430

Ile Val Val Val Pro Gly Ser Gly Phe Arg Gln Val Pro Gly Thr Trp
        435                 440                 445

His Phe Arg Cys Thr Ile Leu Pro Gln Glu Glu Lys Ile Pro Ala Ile
    450                 455                 460

Val Ser Arg Leu Thr Glu Phe His Lys Lys Phe Met Asp Glu Phe Cys
465                 470                 475                 480

Gly

<210> SEQ ID NO 41
<211> LENGTH: 472
```

<212> TYPE: PRT
<213> ORGANISM: Chlamydomonas

<400> SEQUENCE: 41

```
Glu Gly Lys Val Leu His Pro His Leu Leu Asn Glu Asn Val Val Lys
1               5                   10                  15

Thr Gln Tyr Ala Val Arg Gly Glu Leu Tyr Leu Arg Ala Glu Gln Leu
            20                  25                  30

Arg Lys Glu Gly Lys Glu Ile Ile Phe Thr Asn Val Gly Asn Pro His
        35                  40                  45

Ala Leu Gly Ala Lys Pro Leu Thr Phe Thr Arg Gln Val Leu Ala Leu
50                  55                  60

Cys Ala Ala Pro Phe Leu Leu Asp His Pro Lys Val Glu Asp Met Phe
65                  70                  75                  80

Pro Ala Asp Ala Ile Ala Arg Ala Lys Lys Ile Leu Ala Ser Phe Lys
                85                  90                  95

Gly Gly Val Gly Ala Tyr Thr Asp Ser Arg Gly Asn Pro Leu Val Arg
            100                 105                 110

Glu Glu Val Ala Arg Phe Ile Glu Lys Arg Asp Gly Val Pro Ser Asn
        115                 120                 125

Pro Asp His Ile Phe Leu Thr Asp Gly Ala Ser Val Ala Val Arg Leu
130                 135                 140

Cys Leu Asn Ala Met Ile Arg His Asp Arg Asp Ser Val Leu Val Pro
145                 150                 155                 160

Ile Pro Gln Tyr Pro Leu Tyr Ser Ala Ser Ile Arg Leu Tyr Gly Gly
                165                 170                 175

Thr Leu Val Gly Tyr Phe Leu Asp Glu Arg Arg Gly Trp Gly Leu Ser
            180                 185                 190

Val Glu Glu Leu Gln Arg Ala Leu Gln Glu Ser Arg Glu Glu Gly Lys
        195                 200                 205

Leu Val Arg Gly Leu Val Phe Ile Asn Pro Gly Asn Pro Thr Gly Gln
210                 215                 220

Cys Leu Ser Lys Glu Asn Leu Gln Glu Leu Ile Lys Leu Ala Tyr Gln
225                 230                 235                 240

Glu Lys Ile Val Leu Met Ala Asp Glu Val Tyr Gln Glu Asn Val Tyr
                245                 250                 255

Gln Asp Glu Arg Pro Phe Val Ser Ala Lys Lys Val Met Trp Glu Met
            260                 265                 270

Gly Glu Pro Tyr Arg Ser His Val Glu Leu Leu Ser Phe His Thr Val
        275                 280                 285

Ser Lys Gly Thr Ala Gly Glu Cys Gly Leu Arg Gly Gly Tyr Val Glu
290                 295                 300

Met Thr Asn Ile His Pro Gly Ala Ile Glu Glu Val Tyr Lys Cys Ala
305                 310                 315                 320

Ser Ile Asn Leu Ser Pro Asn Thr Met Gly Gln Ile Ala Leu Ser Val
                325                 330                 335

Leu Val Asn Pro Pro Lys Pro Gly Asp Pro Ser Tyr Asp Gln Tyr Thr
            340                 345                 350

Lys Glu Lys Ala Ser Glu Leu Val Ser Leu Arg Arg Arg His Met
        355                 360                 365

Val Thr Asp Gly Phe Asn Ala Leu Asp Gly Val Thr Cys Asn Phe Thr
370                 375                 380

Glu Gly Ala Met Tyr Ser Phe Pro Gln Ile Lys Leu Pro Ala Lys Ala
385                 390                 395                 400
```

```
Leu Glu Ala Ala Lys Ala Ala Gly Lys Ala Gly Asp Val Phe Tyr Cys
                405                 410                 415

Leu Lys Leu Leu Glu Ala Thr Gly Ile Ser Thr Val Pro Gly Ser Gly
            420                 425                 430

Phe Gly Gln Glu Glu Gly Thr Phe His Leu Arg Thr Thr Ile Leu Pro
        435                 440                 445

Arg Glu Glu Val Met Thr Thr Phe Val Glu Lys Phe Asp Lys Phe His
    450                 455                 460

Lys Asp Phe Met Lys Gln Tyr Ser
465                 470

<210> SEQ ID NO 42
<211> LENGTH: 480
<212> TYPE: PRT
<213> ORGANISM: Homo sapiens

<400> SEQUENCE: 42

Arg Ala Lys Val Leu Thr Leu Asp Gly Met Asn Pro Arg Val Arg Arg
 1               5                  10                  15

Val Glu Tyr Ala Val Arg Gly Pro Ile Val Gln Arg Ala Leu Glu Leu
            20                  25                  30

Glu Gln Glu Leu Arg Gln Gly Val Lys Lys Pro Phe Thr Glu Val Ile
        35                  40                  45

Arg Ala Asn Ile Gly Asp Ala Gln Ala Met Gly Gln Arg Pro Ile Thr
    50                  55                  60

Phe Leu Arg Gln Val Leu Ala Leu Cys Val Asn Pro Asp Leu Leu Ser
65                  70                  75                  80

Ser Pro Asn Phe Pro Asp Asp Ala Lys Lys Arg Ala Glu Arg Ile Leu
                85                  90                  95

Gln Ala Cys Gly Gly His Ser Leu Gly Ala Tyr Ser Val Ser Ser Gly
            100                 105                 110

Ile Gln Leu Ile Arg Glu Asp Val Ala Arg Tyr Ile Glu Arg Arg Asp
        115                 120                 125

Gly Gly Ile Pro Ala Asp Pro Asn Asn Val Phe Leu Ser Thr Gly Ala
    130                 135                 140

Ser Asp Ala Ile Val Thr Val Leu Lys Leu Leu Val Ala Gly Glu Gly
145                 150                 155                 160

His Thr Arg Thr Gly Val Leu Ile Pro Ile Pro Gln Tyr Pro Leu Tyr
                165                 170                 175

Ser Ala Thr Leu Ala Glu Leu Gly Ala Val Gln Val Asp Tyr Tyr Leu
            180                 185                 190

Asp Glu Glu Arg Ala Trp Ala Leu Asp Val Ala Glu Leu His Arg Ala
        195                 200                 205

Leu Gly Gln Ala Arg Asp His Cys Arg Pro Arg Ala Leu Cys Val Ile
    210                 215                 220

Asn Pro Gly Asn Pro Thr Gly Gln Val Gln Thr Arg Glu Cys Ile Glu
225                 230                 235                 240

Ala Val Ile Arg Phe Ala Phe Glu Glu Arg Leu Phe Leu Leu Ala Asp
                245                 250                 255

Glu Val Tyr Gln Asp Asn Val Tyr Ala Ala Gly Ser Gln Phe His Ser
            260                 265                 270

Phe Lys Lys Val Leu Met Glu Met Gly Pro Pro Tyr Ala Gly Gln Gln
        275                 280                 285

Glu Leu Ala Ser Phe His Ser Thr Ser Lys Gly Tyr Met Gly Glu Cys
    290                 295                 300
```

-continued

```
Gly Phe Arg Gly Gly Tyr Val Glu Val Val Asn Met Asp Ala Ala Val
305                 310                 315                 320

Gln Gln Gln Met Leu Lys Leu Met Ser Val Arg Leu Cys Pro Pro Val
                325                 330                 335

Pro Gly Gln Ala Leu Leu Asp Leu Val Val Ser Pro Pro Ala Pro Thr
                340                 345                 350

Asp Pro Ser Phe Ala Gln Phe Gln Ala Glu Lys Gln Ala Val Leu Ala
                355                 360                 365

Glu Leu Ala Ala Lys Ala Lys Leu Thr Glu Gln Val Phe Asn Glu Ala
                370                 375                 380

Pro Gly Ile Ser Cys Asn Pro Val Gln Gly Ala Met Tyr Ser Phe Pro
385                 390                 395                 400

Arg Val Gln Leu Pro Pro Arg Ala Val Glu Arg Ala Gln Glu Leu Gly
                405                 410                 415

Leu Ala Pro Asp Met Phe Phe Cys Leu Arg Leu Leu Glu Glu Thr Gly
                420                 425                 430

Ile Cys Val Val Pro Gly Ser Gly Phe Gly Gln Arg Glu Gly Thr Tyr
                435                 440                 445

His Phe Arg Met Thr Ile Leu Pro Pro Leu Glu Lys Leu Arg Leu Leu
                450                 455                 460

Leu Glu Lys Leu Ser Arg Phe His Ala Lys Phe Thr Leu Glu Tyr Ser
465                 470                 475                 480

<210> SEQ ID NO 43
<211> LENGTH: 486
<212> TYPE: PRT
<213> ORGANISM: Saccharomyces cerevisiae

<400> SEQUENCE: 43

Pro Ala Glu Gln Leu Thr Leu Glu Asp Val Asn Glu Asn Val Leu Lys
1               5                   10                  15

Ala Lys Tyr Ala Val Arg Gly Ala Ile Pro Met Arg Ala Glu Glu Leu
                20                  25                  30

Lys Ala Gln Leu Glu Lys Asp Pro Gln Ser Leu Pro Phe Asp Arg Ile
                35                  40                  45

Ile Asn Ala Asn Ile Gly Asn Pro Gln Gln Leu Gln Gln Lys Pro Leu
50                  55                  60

Thr Tyr Tyr Arg Gln Val Leu Ser Leu Leu Gln Tyr Pro Glu Leu Leu
65                  70                  75                  80

Asn Gln Asn Glu Gln Gln Leu Val Asp Ser Lys Leu Phe Lys Leu Asp
                85                  90                  95

Ala Ile Lys Arg Ala Lys Ser Leu Met Glu Asp Ile Gly Gly Ser Val
                100                 105                 110

Gly Ala Tyr Ser Ser Ser Gln Gly Val Glu Gly Ile Arg Lys Ser Val
                115                 120                 125

Ala Glu Phe Ile Thr Lys Arg Asp Glu Gly Ile Ser Tyr Pro Glu
                130                 135                 140

Asp Ile Phe Leu Thr Ala Gly Ala Ser Ala Ala Val Asn Tyr Leu Leu
145                 150                 155                 160

Ser Ile Phe Cys Arg Gly Pro Glu Thr Gly Val Leu Ile Pro Ile Pro
                165                 170                 175

Gln Tyr Pro Leu Tyr Thr Ala Thr Leu Ala Leu Asn Asn Ser Gln Ala
                180                 185                 190

Leu Pro Tyr Tyr Leu Asp Glu Asn Ser Gly Trp Ser Thr Asn Pro Glu
                195                 200                 205
```

```
Glu Ile Glu Thr Val Val Lys Glu Ala Ile Gln Asn Glu Ile Lys Pro
            210                 215                 220

Thr Val Leu Val Val Ile Asn Pro Gly Asn Pro Thr Gly Ala Val Leu
225                 230                 235                 240

Ser Pro Glu Ser Ile Ala Gln Ile Phe Glu Val Ala Ala Lys Tyr Gly
                245                 250                 255

Thr Val Ile Ala Asp Glu Val Tyr Gln Glu Asn Ile Phe Pro Gly
            260                 265                 270

Thr Lys Phe His Ser Met Lys Lys Ile Leu Arg His Leu Gln Arg Glu
                275                 280                 285

His Pro Gly Lys Phe Asp Asn Val Gln Leu Ala Ser Leu His Ser Thr
            290                 295                 300

Ser Lys Gly Val Ser Gly Glu Cys Gly Gln Arg Gly Gly Tyr Met Glu
305                 310                 315                 320

Leu Thr Gly Phe Ser His Glu Met Arg Gln Val Ile Leu Lys Leu Ala
                325                 330                 335

Ser Ile Ser Leu Cys Pro Val Val Thr Gly Gln Ala Leu Val Asp Leu
                340                 345                 350

Met Val Arg Pro Pro Val Glu Gly Glu Ser Phe Glu Ser Asp Gln
            355                 360                 365

Ala Glu Arg Asn Ser Ile His Glu Lys Leu Ile Thr Arg Ala Met Thr
            370                 375                 380

Leu Tyr Glu Thr Phe Asn Ser Leu Gly Ile Glu Cys Gln Lys Pro
385                 390                 395                 400

Gln Gly Ala Met Tyr Leu Phe Pro Lys Ile Asp Leu Pro Phe Lys Ala
                405                 410                 415

Val Gln Glu Ala Arg His Leu Glu Leu Thr Pro Asp Glu Phe Tyr Cys
            420                 425                 430

Lys Lys Leu Leu Glu Ser Thr Gly Ile Cys Thr Val Pro Gly Ser Gly
                435                 440                 445

Phe Gly Gln Glu Pro Gly Thr Tyr His Leu Arg Thr Thr Phe Leu Ala
            450                 455                 460

Pro Gly Leu Glu Trp Ile Lys Lys Trp Glu Ser Phe His Lys Glu Phe
465                 470                 475                 480

Phe Asp Gln Tyr Arg Asp
                485

<210> SEQ ID NO 44
<211> LENGTH: 404
<212> TYPE: PRT
<213> ORGANISM: Escherichia coli

<400> SEQUENCE: 44

Met Ser Pro Ile Glu Lys Ser Ser Lys Leu Glu Asn Val Cys Tyr Asp
1               5                   10                  15

Ile Arg Gly Pro Val Leu Lys Glu Ala Lys Arg Leu Glu Glu Glu Gly
            20                  25                  30

Asn Lys Val Leu Lys Leu Asn Ile Gly Asn Pro Ala Pro Phe Gly Phe
        35                  40                  45

Asp Ala Asp Glu Ile Leu Val Asp Val Ile Arg Asn Leu Pro Thr Ala
    50                  55                  60

Gln Gly Tyr Cys Asp Ser Lys Gly Leu Tyr Ser Ala Arg Lys Ala Ile
65                  70                  75                  80

Met Gln His Tyr Gln Ala Arg Gly Met Arg Asp Val Thr Val Glu Asp
                85                  90                  95
```

```
Ile Tyr Ile Gly Asn Gly Val Ser Glu Leu Ile Val Gln Ala Met Gln
            100                 105                 110

Ala Leu Leu Asn Ser Gly Asp Glu Met Leu Val Pro Ala Pro Asp Tyr
        115                 120                 125

Pro Leu Trp Thr Ala Ala Val Ser Leu Ser Ser Gly Lys Ala Val His
    130                 135                 140

Tyr Leu Cys Asp Glu Ser Ser Asp Trp Phe Pro Asp Leu Asp Asp Ile
145                 150                 155                 160

Arg Ala Lys Ile Thr Pro Arg Thr Arg Gly Ile Val Ile Ile Asn Pro
                165                 170                 175

Asn Asn Pro Thr Gly Ala Val Tyr Ser Lys Glu Leu Leu Met Glu Ile
            180                 185                 190

Val Glu Ile Ala Arg Gln His Asn Leu Ile Ile Phe Ala Asp Glu Ile
        195                 200                 205

Tyr Asp Lys Ile Leu Tyr Asp Asp Ala Glu His His Ser Ile Ala Pro
    210                 215                 220

Leu Ala Pro Asp Leu Leu Thr Ile Thr Phe Asn Gly Leu Ser Lys Thr
225                 230                 235                 240

Tyr Arg Val Ala Gly Phe Arg Gln Gly Trp Met Val Leu Asn Gly Pro
                245                 250                 255

Lys Lys His Ala Lys Gly Tyr Ile Glu Gly Leu Glu Met Leu Ala Ser
            260                 265                 270

Met Arg Leu Cys Ala Asn Val Pro Ala Gln His Ala Ile Gln Thr Ala
        275                 280                 285

Leu Gly Gly Tyr Gln Ser Ile Ser Glu Phe Ile Thr Pro Gly Gly Arg
    290                 295                 300

Leu Tyr Glu Gln Arg Asn Arg Ala Trp Glu Leu Ile Asn Asp Ile Pro
305                 310                 315                 320

Gly Val Ser Cys Val Lys Pro Arg Gly Ala Leu Tyr Met Phe Pro Lys
                325                 330                 335

Ile Asp Ala Lys Arg Phe Asn Ile His Asp Asp Gln Lys Met Val Leu
            340                 345                 350

Asp Phe Leu Leu Gln Glu Lys Val Leu Leu Val Gln Gly Thr Ala Phe
        355                 360                 365

Asn Trp Pro Trp Pro Asp His Phe Arg Ile Val Thr Leu Pro Arg Val
    370                 375                 380

Asp Asp Ile Glu Leu Ser Leu Ser Lys Phe Ala Arg Phe Leu Ser Gly
385                 390                 395                 400

Tyr His Gln Leu

<210> SEQ ID NO 45
<211> LENGTH: 397
<212> TYPE: PRT
<213> ORGANISM: Thermococcus

<400> SEQUENCE: 45

Met Val Lys Ala Ser Lys Arg Ala Met Ser Ile Glu Tyr Ala Ile Arg
  1               5                  10                  15

Asp Val Val Leu Pro Ala Arg Glu Leu Glu Lys Gln Gly Ile Lys Ile
             20                  25                  30

Ile Lys Leu Asn Ile Gly Asp Pro Val Lys Phe Asp Phe Gln Pro Pro
         35                  40                  45

Glu His Met Lys Lys Ala Tyr Cys Glu Ala Ile Met Glu Gly His Asn
     50                  55                  60

Tyr Tyr Gly Asp Ser Glu Gly Asp Arg Glu Leu Arg Glu Ala Ile Val
```

-continued

```
            65                  70                  75                  80
Glu Arg Glu Lys Lys Asn Gly Val Asp Ile Thr Pro Glu Asp Val
                85                  90                  95

Gln Val Thr Ala Ala Val Thr Glu Ala Leu Gln Phe Ile Phe Gly Ala
               100                 105                 110

Leu Ile Asp Gly Gly Glu Ile Leu Ile Pro Gly Pro Ser Tyr Pro
           115                 120                 125

Pro Tyr Val Gly Leu Val Lys Phe Tyr Gly Gly Val Pro Lys Ala Tyr
           130                 135                 140

Arg Thr Val Glu Glu Gly Trp Gln Pro Asp Ile Asp Asp Met Arg
145                 150                 155                 160

Lys Lys Ile Thr Glu Lys Thr Lys Ala Ile Ala Val Ile Asn Pro Asn
               165                 170                 175

Asn Pro Thr Gly Ala Leu Tyr Glu Lys Lys Thr Leu Gln Glu Ile Ile
               180                 185                 190

Asp Leu Ala Gly Glu Tyr Asp Leu Pro Ile Ile Ser Asp Glu Ile Tyr
           195                 200                 205

Asp Leu Met Thr Tyr Glu Gly Lys His Val Ser Pro Gly Ser Leu Thr
210                 215                 220

Lys Asp Val Pro Val Ile Val Met Asn Gly Leu Ser Lys Val Tyr Phe
225                 230                 235                 240

Ala Thr Gly Trp Arg Leu Gly Tyr Met Tyr Phe Val Asp Pro Glu Asn
               245                 250                 255

Lys Leu Ala Glu Val Arg Glu Ala Ile Gly Lys Leu Ala Arg Ile Arg
               260                 265                 270

Leu Cys Pro Asn Thr Pro Ala Gln Lys Ala Ala Ile Ala Gly Leu Arg
           275                 280                 285

Gly Pro Met Asp Tyr Leu Glu Glu Tyr Met Ala Lys Leu Lys Glu Arg
290                 295                 300

Arg Asp Tyr Ile Tyr Lys Arg Leu Asn Glu Met Pro Gly Ile Ser Thr
305                 310                 315                 320

Gln Lys Pro Gln Gly Ala Phe Tyr Ile Phe Pro Lys Ile Glu Glu Gly
               325                 330                 335

Pro Trp Lys Ser Asp Lys Glu Phe Val Leu Asp Val Leu His Asn Ala
               340                 345                 350

His Val Leu Phe Val His Gly Ser Gly Phe Gly Glu Gly Glu Met
           355                 360                 365

His Phe Arg Ser Ile Phe Leu Ala Pro Val Pro Val Leu Glu Glu Ala
           370                 375                 380

Met Asp Asn Leu Glu Lys Phe Met Lys Glu Arg Leu Gly
385                 390                 395
```